(12) United States Patent
Ortega Muñoz et al.

(10) Patent No.: US 8,946,296 B2
(45) Date of Patent: Feb. 3, 2015

(54) SUBSTITUTED HETEROARYL- AND ARYL-CYCLOPROPYLAMINE ACETAMIDES AND THEIR USE

(75) Inventors: Alberto Ortega Muñoz, Barcelona (ES); Julio Castro-Palomino Laria, Barcelona (ES); Matthew Colin Thor Fyfe, Barcelona (ES)

(73) Assignee: Oryzon Genomics S.A., Barcelona (ES)

( * ) Notice: Subject to any disclaimer, the term of this patent is extended or adjusted under 35 U.S.C. 154(b) by 0 days.

(21) Appl. No.: 13/500,687

(22) PCT Filed: Apr. 19, 2010

(86) PCT No.: PCT/EP2010/055103
§ 371 (c)(1),
(2), (4) Date: Jul. 2, 2012

(87) PCT Pub. No.: WO2011/042217
PCT Pub. Date: Apr. 14, 2011

(65) Prior Publication Data
US 2012/0264823 A1    Oct. 18, 2012

(30) Foreign Application Priority Data
Oct. 9, 2009    (EP) .................................... 09172705

(51) Int. Cl.
*A61K 31/165* (2006.01)
*C07C 237/20* (2006.01)
*C07C 237/06* (2006.01)
*C07C 255/54* (2006.01)
*C07D 213/36* (2006.01)

(52) U.S. Cl.
CPC ............. *C07C 237/06* (2013.01); *C07C 255/54* (2013.01); *C07D 213/36* (2013.01); *C07C 2101/02* (2013.01)
USPC .......................................... 514/619; 564/164

(58) Field of Classification Search
None
See application file for complete search history.

(56) References Cited

U.S. PATENT DOCUMENTS

| | | | |
|---|---|---|---|
| 3,106,578 A | 10/1963 | Kaiser et al. | |
| 3,365,458 A | 1/1968 | Biel et al. | |
| 3,471,522 A | 10/1969 | Biel et al. | |
| 3,532,712 A | 10/1970 | Biel et al. | |
| 3,532,749 A | 10/1970 | Biel et al. | |
| 3,758,684 A | 9/1973 | Elion et al. | |
| 4,409,243 A | 10/1983 | Lieb | |
| 4,522,811 A | 6/1985 | Eppstein et al. | |
| 4,530,901 A | 7/1985 | Weissmann | |
| 6,043,393 A | 3/2000 | De Meijere et al. | |
| 6,211,244 B1 | 4/2001 | Van Wagenen et al. | |
| 6,337,074 B1 | 1/2002 | Marsden et al. | |
| 6,809,120 B1 | 10/2004 | Warrington et al. | |
| 7,399,825 B2 | 7/2008 | Lipps et al. | |
| 7,611,704 B2 | 11/2009 | Thorpe et al. | |
| 7,628,993 B2 | 12/2009 | Vilalta et al. | |
| 7,799,782 B2 | 9/2010 | Munson et al. | |
| 8,524,717 B2 | 9/2013 | Guibourt et al. | |
| 8,722,743 B2 | 5/2014 | Ortega Munoz et al. | |
| 2003/0008844 A1 | 1/2003 | Spero et al. | |
| 2003/0236225 A1 | 12/2003 | Protopopova et al. | |
| 2004/0019117 A1 | 1/2004 | Protopopova et al. | |
| 2004/0033986 A1 | 2/2004 | Protopopova et al. | |
| 2004/0048802 A1 | 3/2004 | Ripka et al. | |
| 2004/0132820 A1 | 7/2004 | Gosselin et al. | |
| 2004/0147741 A1 | 7/2004 | Sundermann et al. | |
| 2004/0162287 A1 | 8/2004 | Sundermann et al. | |
| 2004/0176469 A1 | 9/2004 | Thomas | |
| 2004/0229872 A1 | 11/2004 | Friderichs et al. | |
| 2004/0254158 A1 | 12/2004 | Qiao et al. | |
| 2005/0009832 A1 | 1/2005 | Sun et al. | |
| 2005/0154056 A1 | 7/2005 | Yang et al. | |
| 2006/0116370 A1 | 6/2006 | Dollinger et al. | |
| 2006/0148904 A1 | 7/2006 | Protopopova et al. | |
| 2006/0211709 A1 | 9/2006 | Buhr et al. | |

(Continued)

FOREIGN PATENT DOCUMENTS

EP    1 193 268    4/2002
EP    1 704 859    9/2006

(Continued)

OTHER PUBLICATIONS

Wermuth (Molecular Variations Based on Isosteric Replacements, The Practice of Medicinal Chemistry (Second Edition), Academic Press, London, 2003, pp. 189-214).*

(Continued)

*Primary Examiner* — Golam M M Shameem
*Assistant Examiner* — Laura Daniel
(74) *Attorney, Agent, or Firm* — Finnegan, Henderson, Farabow, Garrett & Dunner, LLP

(57) ABSTRACT

The invention relates to compounds of Formula (I): $(A')_x$-(A)-(B)—(Z)-(L)-C(=O)NH$_2$ or pharmaceutically acceptable salts or solvates thereof, wherein: (A) is heteroaryl or aryl; each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2 or 3 substituents independently chosen from halo, haloalkyl, aryl, arylalkoxy, alkyl, alkoxy, cyano, sulfonyl, sulfinyl, and carboxamide; X is 0, 1, 2, or 3; (B) is a cyclopropyl ring, wherein (A) and (Z) are covalently bonded to different carbon atoms of (B); (Z) is —NH—; and (L) is —(CH$_2$)$_m$CR$_1$,R$_2$—, wherein m is 0, 1, 2, 3, 4, 5, or 6, and wherein R$_1$ and R$_2$ are each independently hydrogen or C$_1$-C$_6$ alkyl; provided that, if (L) is —CH$_2$— or —CH(CH$_3$)—, then X is not 0. The compounds of the invention are useful in the treatment of diseases such as cancer and neurodegenerative diseases.

33 Claims, 5 Drawing Sheets

(56) References Cited

U.S. PATENT DOCUMENTS

Figure 1:
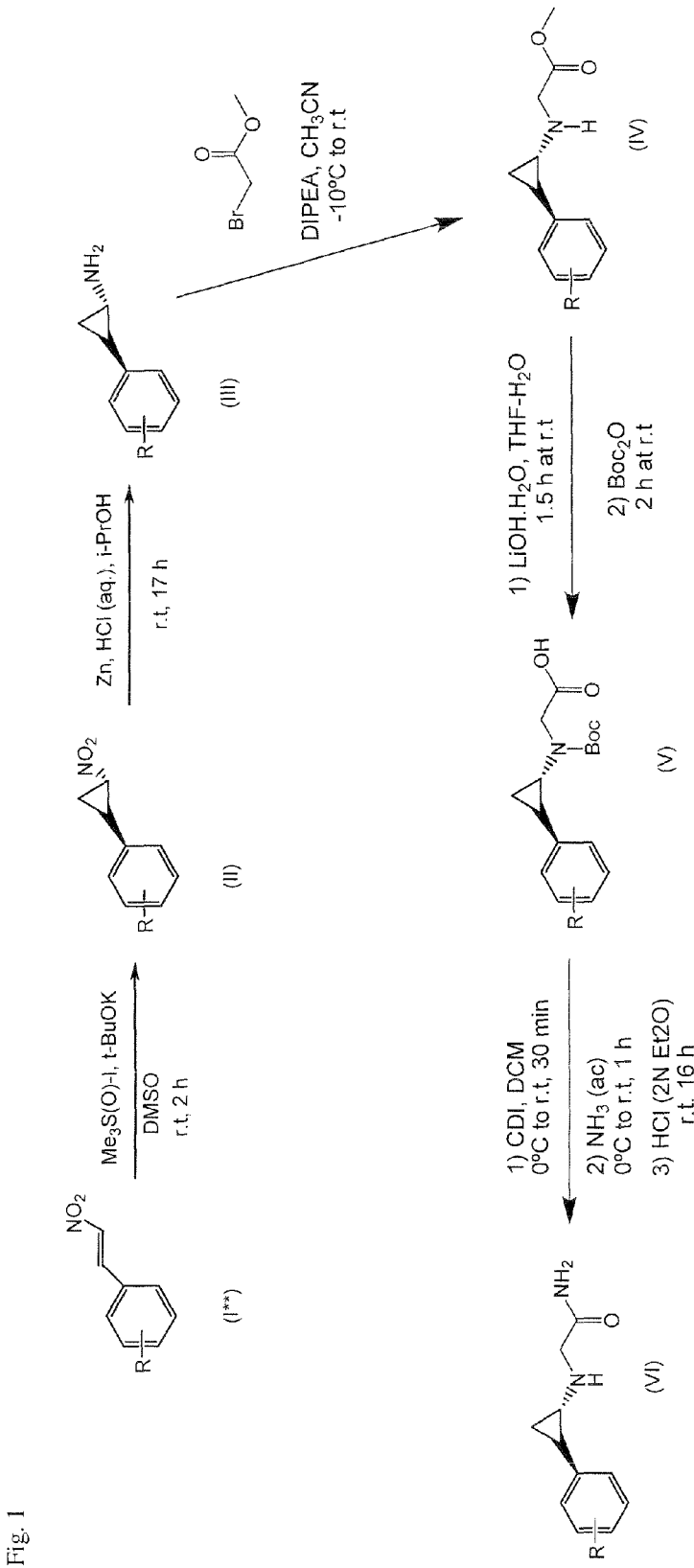

| | | | |
|---|---|---|---|
| 2006/0270673 | A1 | 11/2006 | Duggan et al. |
| 2006/0275366 | A1 | 12/2006 | Malcolm et al. |
| 2006/0287287 | A1 | 12/2006 | Gerritz et al. |
| 2007/0213338 | A1 | 9/2007 | Lebsack et al. |
| 2008/0139665 | A1 | 6/2008 | Schuele et al. |
| 2008/0242698 | A1* | 10/2008 | Flor et al. ............... 514/307 |
| 2008/0269228 | A1 | 10/2008 | Moore et al. |
| 2009/0203750 | A1 | 8/2009 | Kozikowski et al. |
| 2009/0247530 | A1 | 10/2009 | Nolte et al. |
| 2010/0016262 | A1 | 1/2010 | Mehal et al. |
| 2010/0240649 | A1 | 9/2010 | Zhang |
| 2010/0292225 | A1 | 11/2010 | Chamoin et al. |
| 2010/0324147 | A1 | 12/2010 | McCafferty et al. |
| 2012/0202810 | A1 | 8/2012 | Nolte et al. |
| 2013/0197095 | A1 | 8/2013 | Nolte et al. |

FOREIGN PATENT DOCUMENTS

| | | |
|---|---|---|
| EP | 1 741 708 | 1/2007 |
| EP | 2 233 495 | 9/2010 |
| GB | 1 307 341 | 2/1973 |
| JP | 2001-354563 | 12/2001 |
| SU | 230169 | 10/1968 |
| WO | WO-94/27947 | 12/1994 |
| WO | WO-96/38141 | 12/1996 |
| WO | WO-98/18459 | 5/1998 |
| WO | WO-99/05142 | 2/1999 |
| WO | WO-99/05143 | 2/1999 |
| WO | WO-99/31072 | 6/1999 |
| WO | WO-99/54440 | 10/1999 |
| WO | WO-99/67203 | 12/1999 |
| WO | WO-00/34283 | 6/2000 |
| WO | WO-01/92264 | 12/2001 |
| WO | WO-02/079152 | 10/2002 |
| WO | WO-03/087064 | 10/2003 |
| WO | WO-03/093297 | 11/2003 |
| WO | WO-03/096989 | 11/2003 |
| WO | WO-2004/020415 | 3/2004 |
| WO | WO2004/055010 A2 | 7/2004 |
| WO | WO-2004/062601 | 7/2004 |
| WO | WO-2004/065367 A1 | 8/2004 |
| WO | WO-2004/072086 | 8/2004 |
| WO | WO-2005/009941 | 2/2005 |
| WO | WO-2005/023761 | 3/2005 |
| WO | WO2005/025558 A1 | 3/2005 |
| WO | WO-2005/037843 | 4/2005 |
| WO | WO-2005/058808 | 6/2005 |
| WO | WO-2005/058883 | 6/2005 |
| WO | WO-2005/058884 | 6/2005 |
| WO | WO-2005/103003 | 11/2005 |
| WO | WO-2006/071608 | 7/2006 |
| WO | WO-2006/087206 | 8/2006 |
| WO | WO-2007/000248 | 1/2007 |
| WO | WO-2007/005896 | 1/2007 |
| WO | WO-2007/015824 A2 | 2/2007 |
| WO | WO-2007/021839 | 2/2007 |
| WO | WO-2007/025144 | 3/2007 |
| WO | WO-2007/025709 | 3/2007 |
| WO | WO-2007/106016 | 9/2007 |
| WO | WO-2007/134799 | 11/2007 |
| WO | WO-2008/033466 | 3/2008 |
| WO | WO-2008/116156 | 9/2008 |
| WO | WO-2008/127734 | 10/2008 |
| WO | WO-2009/001132 | 12/2008 |
| WO | WO-2009/023179 | 2/2009 |
| WO | WO-2009/039134 | 3/2009 |
| WO | WO-2009/052078 | 4/2009 |
| WO | WO-2009/097278 | 8/2009 |
| WO | WO-2009/109991 | 9/2009 |
| WO | WO-2009/117515 | 9/2009 |
| WO | WO 2009/117515 A2 | 9/2009 |
| WO | WO-2009/145856 | 12/2009 |
| WO | WO-2009/153197 | 12/2009 |
| WO | WO-2010/011845 | 1/2010 |
| WO | WO-2010/014921 | 2/2010 |
| WO | WO-2010/030592 | 3/2010 |
| WO | WO-2010/043721 | 4/2010 |
| WO | WO2010/084160 | 7/2010 |
| WO | WO-2010/085749 | 7/2010 |
| WO | WO-2010/099527 | 9/2010 |
| WO | WO-2010/139784 | 12/2010 |
| WO | WO-2010/143582 | 12/2010 |
| WO | WO-2011/022489 | 2/2011 |
| WO | WO-2011/031934 | 3/2011 |
| WO | WO-2011/035941 | 3/2011 |
| WO | WO-2011/042217 | 4/2011 |
| WO | WO-2011/057262 | 5/2011 |
| WO | WO-2011/106105 | 9/2011 |
| WO | WO-2011/106106 | 9/2011 |
| WO | WO-2011/113005 | 9/2011 |
| WO | WO-2011/131576 | 10/2011 |
| WO | WO-2011/131697 | 10/2011 |
| WO | WO-2011/132083 | 10/2011 |
| WO | WO-2012/001531 | 1/2012 |
| WO | WO-2012/013727 | 2/2012 |
| WO | WO-2012/013728 | 2/2012 |
| WO | WO-2012/034116 | 3/2012 |
| WO | WO-2012/042042 | 4/2012 |
| WO | WO-2012/045883 | 4/2012 |
| WO | WO-2012/072713 | 6/2012 |
| WO | WO-2012/107498 | 8/2012 |
| WO | WO-2012/107499 | 8/2012 |
| WO | WO-2012/135113 | 10/2012 |
| WO | WO-2012/156531 | 11/2012 |
| WO | WO-2012/156537 | 11/2012 |
| WO | WO-2013/057320 | 4/2013 |
| WO | WO-2013/057322 | 4/2013 |

OTHER PUBLICATIONS

Shi, Yang. Nature Reviews Genetics, 8, (2007) 829-833.*
. MedicineNet.com <http://www.medterms.com, 2004>.*
Forneris, Federico. Trends in Biochemical Sciences 33(4), 2008, 181-189.*
Youdim, Moussa. Mechanisms of Ageing and Development 126, 2005, 317-326.*
International Search Report received in the corresponding international Patent Application No. PCT/EP2010/055103, dated Mar. 3, 2011.
Gooden, et al., "Facile synthesis of substituted trans-2-arylcyclopropylamine inhibitors of the human histone demethylase LSD1 and monoamine oxidases A and B", Bioorganic & Medicinal Chemistry Letters, vol. 18, 2008, pp. 3047-3051.
Zirkle, et al., "2-Substituted Cyclopropylamines. II. Effect of Structure upon Monoamine Oxidase-Inhibitory Activity as Measured in Vivo by Protentiation of Tryptamine Convulsions", Journal of Medicinal and Pharmaceutical Chemistry, vol. 5, 1962, pp. 1265-1284.
Ahmed et al., "Ticagrelor: A New Reversible Oral Antiplatelet Agent," International Research Journal of Pharmacy, 1(1):62-69 (2010).
Arya et al., "Synthesis of 5H-Dibenzo[a,d]cycloheptene Derivatives With Diverse Biological Activities," Indian Journal of Chemistry B, 16B:220-225 (1978).
Bar-Am et al., "Regulation of Bcl-2 Family Proteins, Neurotrophic Factors, and APP Processing in the Neurorescue Activity of Propargylamine," Federation of American Societies for Experimental Biology Journal, 19(13):1899-1901 (2005).
Barlesi et al., "Global Histone Modifications Predict Prognosis of Resected Non Small-Cell Lung Cancer," Journal of Clinical Oncology, 25(28):4358-4364 (2007).
Benelkebir et al., "Enantioselective Synthesis of Tranylcypromine Analogues as Lysine Demethylase (LSD1) Inhibitors," Bioorganic & Medicinal Chemistry, 19(12):3709-3716 (2011).
Biljak et al.,"Platelet Count, Mean Platelet Volume and Smoking Status in Stable Chronic Obstructive Pulmonary Disease," Platelets, 22(6):466-70 (2011).
Binda et al., "Biochemical, Structural, and Biological Evaluation of Tranylcypromine Derivatives as Inhibitors of Histone Demethylases LSD1 and LSD2," Journal of the American Chemical Society, 132(19):6827-6833 (2010).

(56) References Cited

OTHER PUBLICATIONS

Bisi et al., "Multidrug Resistance Reverting Activity and Antitumor Profile of New Phenothiazine Derivatives," Bioorganic & Medicinal Chemistry, 16(13):6474-6482 (2008).
Boilard et al., "Platelets Amplify Inflammation in Arthritis Via Collagen-Dependent Microparticle Production," Science, 327(5965):580-583 (2010).
Bolesov et al., "Cyclopropanes and Cyclobutanes LXIX," Zhurnal Organicheskoi Khimii (English Translation), 10(10):2122-2128 (1974).
Brand et al., "Targeted Gene Expression as a Means of Altering Cell Fates and Generating Dominant Phenotypes," Development, 118:401-415 (1993).
Brydon et al., "Platelets, Coronary Heart Disease and Stress," Brain, Behavior and Immunity, 20(2):113-119 (2006).
Burakova et al., "N- and O-Alkylation of 3-Indolylcyclopropylacetic Acid Derivatives," Russian Chemical Bulletin, 51(10):1829-1840 (2002).
Burk et al., "Cognitive Deficits in Spinocerebellar Ataxia 2," Brain, 122:769-777 (1999).
Cakmak et al., "Platelets: Indicator of Inflammation in COPD," International Journal of Medicine and Medical Sciences, 1(5):227-229 (2009).
Calogero et al., "Inhibition of Cell Growth by EGR-1 in Human Primary Cultures From Malignant Glioma," Cancer Cell International, 4, (2004).
Casero et al., "Recent Advances in the Development of Polyamine Analogues as Antitumor Agents," Journal of Medicinal Chemistry, 52(15):4551-4573 (2009).
Chen et al., "Association of Insulin Resistance and Hematologic Parameters: Study of a Middle-Aged and Elderly Chinese Population in Taiwan," Journal of the Chinese Medical Association, 69(6):248-253 (2006).
Chimenti et al. "Synthesis, Stereochemical Identification, and Selective Inhibitory Activity Against Human Monoamine Oxidase-B of 2-Methylcyclohexylidene-(4-Arylthiazol-2-yl)hydrazones," Journal of Medicinal Chemistry, 51 (16):4874-4880 (2008).
Choi et al. "Histone Demethylase LSD1 is Required to Induce Skeletal Muscle Differentiation by Regulating Myogenic Factors," Biochemical and Biophysical Research Communications, 401(3):327-332 (2010).
Choo et al., "Genetic Organization and Diversity of the Hepatitis C Virus," Proceedings of the National Academy of Sciences, 88:2451-2455 (1991).
Culhane et al., "A Mechanism-Based Inactivator for Histone Demethylase LSD1," Journal of the American Chemical Society, 128(14):4536-4537 (2006).
Culhane et al., "Comparative Analysis of Small Molecules and Histone Substrate Analogues as LSD1 Lysine Demethylase Inhibitors," Journal of the American Chemical Society, 132(9):3164-3176 (2010).
Danese et al., "Platelets in Inflammatory Bowel Disease: Clinical, Pathogenic and Therapeutic Implications," American Journal of Gastroenterology, 99(5):938-945 (2004).
Di Stefano et al., "Mutation of Drosophila LSD1 Disrupts H3-K4 Methylation, Resulting in Tissue-Specific Defects During Development," Current Biology, 17:808-812 (2007).
East et al., "An Orally Bioavailable Positive Allosteric Modulator of the mGlu4 Receptor With Efficacy in an Animal Model of Motor Dysfunction," Bioorganic & Medicinal Chemistry Letters, 20:4901-4905 (2010).
Ellis et al., "Expression of Drosophila Glass Protein and Evidence for Negative Regulation of Its Activity in Non-Neuronal Cells by Another DNA-Binding Protein," Development, 119:855-865 (1993).
Elsheikh et al. "Global Histone Modifications in Breast Cancer Correlate With Tumor Phenotypes, Prognostic Factors and Patient Outcome," Cancer Research, 69:3802-3809 (2009).
Erazo et al., "Varicella-Zoster Virus Open Reading Frame 66 Protein Kinase is Required for Efficient Viral Growth in Primary Human Corneal Stromal Fibroblast Cells," Journal of Virology, 82(15):7653-7665 (2008).
Faler et al., "The Kulinkovich Reaction in the Synthesis of Constrained N,N-Dialkyl Neurotransmitter Analogues," Organic Letters, 9(10):1987-1990 (2007).
Ferlay et al., "Estimates of the Cancer Incidence and Mortality in Europe in 2006," Annals of Oncology , 18(3):581-592 (2007).
Ferraro et al., "EGR1 Predicts PTEN and Survival in Patients With Non-Small-Cell Lung Cancer," Journal of Clinical Oncology, 23(9):1921-1926 (2005).
Fischer et al., "Recovery of Learning and Memory is Associated With Chromatin Remodelling," Nature, 447:178-182 (2007).
Forneris et al., "LSD1: Oxidative Chemistry for Multifaceted Functions in Chromatin Regulation," Trends in Biochemical Sciences , 33(4):181-189 (2008).
Gawaz et al., "Platelets in Inflammation and Atherogenesis," The Journal of Clinical Investigation, 115(12):3378-3384 (2005).
Han et al. "Modulation of Breast Cancer Resistance Protein (BCRP/ABCG2) by Non-Basic Chalcone Analogues," European Journal of Pharmaceutical Science, 35:30-41 (2008).
Han et al., "Antidepressants Reveal Differential Effect Against 1-Methyl-4-Phenylpyridinium Toxicity in Differentiated PC12 Cells," European Journal of Pharmacology, 604 (1-3):36-44 (2009) (doi:10.1016/j.ejphar.2008.12.025).
Hayami et al., "Overexpression of LSD1 Contributes to Human Carcinogenesis Through Chromatin Regulation in Various Cancers," International Journal of Cancer, 128(3):574-86, (2011) PMID 20333681.
Hruschka et al., "Fluorinated Pphenylcyclopropylamines. Part 5: Effect of Electron-Withdrawing or -Donating Aryl Substituents on the Inhibition of Monoamine Oxidases A and B by 2-Aryl-2-Fluoro-cyclopropylamines," Bioorganic & Medicinal Chemistry, 16(15):7148-7166 (2008).
Huang et al., "Novel Oligoamine Analogues Inhibit Lysine-Specific Demethylase 1 (LSD1) and Induce Re-Expression of Epigeneticall Silenced Genes," Clinical Cancer Research, 15(23):7217-7228 (2009).
Huang et al., "p53 is Regulated by the Lysine Demethylase LSD1," Nature, 449:105-108 (2007).
Huang et al.,"Inhibition of Lysine-Specific Demethylase 1 by Polyamine Analogues Results in Reexpression of Aberrantly Silenced Genes," Proceedings of the National Academy of Sciences, 104(19):8023-8028 (2007).
Jackson et al., "Polyglutamine-Expanded Human Huntingtin Transgenes Induce Degeneration of Drosophila Photoreceptor Neurons," Neuron, 21:633-642 (1998).
Kahl et al., "Androgen Receptor Coactivators Lysine-Specific Histone Demethylase 1 and Four and a Half LIM Domain Protein 2 Predict Risk of Prostate Cancer Recurrence," Cancer Research, 66 (23):11341-11347 (2006).
Kaiser et al.., 2-Substituted Cyclopropylamines, Journal of Medicinal Chemistry, American Chemical Society, 5(6):1243-1284 (1962).
Kiefmann et al., "Red Blood Cells Induce Hypoxic Lung Inflammation," Blood, 111(10):5205-5214 (2008).
Kornerup et al., "The Role of Platelets in the Pathophysiology of Asthma," Platelets, 18(5):319-328 (2007).
Krieger et al., "Enhancement of Hepatitis C Virus RNA Replication by Cell Culture-Adaptive Mutations," Journal of Virology, 75(10):4614-4624 (2001).
Lan et al. "Mechanisms Involved in the Regulation of Histone Lysine Demethylases," Current Opinion in Cell Biology, 20:316-325 (2008).
Lee et al., "Combinatorial Lead Optimization of [1,2]-Diamines Based on Ethambutol as Potential Antituberculosis Preclinical Candidates," Journal of Combinatorial Chemistry, 5(2):172-187 (2003).
Lee et al., "Histone H3 Lysine 4 Demethylation is a Target of Nonselective Antidepressive Medications," Chemical Biology, 13:563-567 (2006).
Li et al., "Association Between Inflammatory Mediators and Angiographic Morphologic Features Indicating Thrombus Formation in Patients With Acute Myocar Dial Infarction", Chinese Medical Journal, 122(15):1738-42 (2009).

(56) References Cited

OTHER PUBLICATIONS

Liang et al., "Inhibition of the Histone Demethylase LSD1 Blocks Alpha-Herpesvirus Lytic Replication and Reactivation From Latency," Nature Medicine, 15(11):1312-1317 (2009).
Lim et al., "Lysine-Specific Demethylase 1 (LSD1) is Highly Expressed in ER-Negative Breast Cancers and a Biomarker Predicting Aggressive Biology," Carcinogenesis, 31(3):512-20 (2010) epub Dec. 2009, PMID 20042638.
Lucerna et al., "Sustained Expression of Early Growth Response Protein-1 Blocks Angiogenesis and Tumor Growth," Cancer Research, 66:6708-6713 (2006).
Lupu Roxana, "Up-To-Date in the Hematological Malignancies Treatment," Maedica, 1(1):63-65 (2006).
Maclay et al., "Increased Platelet Activation in Patients With Stable and Acute Exacerbation of COPD," Thorax, 66:769-774 (2011).
Mannaioni et al., "Platelets and Inflammation: Role of Platelet-Derived Growth Factor, Adhesion Molecules and Histamine," Inflammation Research, 46(1):4-18 (1997).
McNicol et al., "Beyond Hemostasis: The Role of Platelets in Inflammation, Malignancy and Infection," Cardiovascular & Haematological Disorders-Drug Targets, 8:99-117 (2008).
Meanwell, "Synopsis of Some Recent Tactical Application of Bioisosteres in Drug Design," 2011, Journal of Medicinal Chemistry, 54(8):2529-2591, PMID 21413808 (2011).
Metzger et al., "LSD1 Demethylates Repressive Histone Marks to Promote AndrogenRreceptor-Dependent Transcription," Nature, 437:436-439 (2005).
Mimasu et al. "Crystal Structure of Histone Demethylase LSD1 and Tranylcypromine at 2.25 Å," Biochemical and Biophysical Research Communications, 366:15-22 (2008).
Mimasu et al., "Structurally Designed Trans-2-Phenylcyclopropylamine Derivatives Potently Inhibit Histone Demethylase LSD1/KDM1," Biochemistry, 49(30):6494-6503 (2010).
Moritani et al., "Activation of Platelets in Bronchial Asthma," Chest, 113:452-458 (1998).
Neelamegan et al., "Brain-Penetrant LSD1 Inhibitors Can Block Memory Consolidation," ACS Chemical Neuroscience, 3(2):120-128 (2012).
Ogasawara et al., "Synthesis and Biological Activity of Optically Active NCL-1, a Lysine-Specific Demethylase 1 Selective Inhibitor," Bioorganic & Medicinal Chemistry, doi:10.1016/j.bmc.2010.12.024 (2011).
O'Sullivan et al., "The Inflammatory Role of Platelets in Cystic Fibrosis," American Journal of Respiratory and Critical Care Medicine, 173:483-90 (2006).
Pannala et al. "Synthesis and Structure—Activity Relationship of 4-(2-Aryl-Cyclopropylamino)-Quinoline-3-Carbonitriles as EGFR Tyrosine Kinase Inhibitors," Bioorganic & Medicinal Chemistry Letters, 17 (21):5978-5082 (2007).
Pitchford et al., "Platelet P-Selectin is Required for Pulmonary Eosinophil and Lymphocyte Recruitment in a Murine Model of Allergic Inflammation," Blood, 105:2074-2081 (2005).
Pollock et al., "Lysine-Specific Histone Demethylase 1 Inhibitors Control Breast Cancer Proliferation in ERalpha-Dependent and -Independent Manners," ACS Chemical Biology, 7:1221-1231 (2012).
Ravina et al., "The Relationship Between CAG Repeat Length and Clinical Progression in Huntington's Disease," Movement Disorders, 23(9):1223-7 (2008).
Reddy et al., "Role of Lysine-Specific Demethylase 1 in the Proinflammatory Phenotype of Vascular Smooth Muscle Cells of Diabetic Mice," Circulation Research, 103:615-23 (2008).
Riley et al., "Absolute Configuration of (+)- and (−)-Trans-2-Phenylcyclopropylamine Hydrochloride," Journal of Medicinal Chemistry, 15(11):1187-1188 (1972).
Rinder et al., "Correlation of Thrombosis With Increased Platelet Turnover in Thrombocytosis," Blood, 91(4):1288-1294 (1998).
Schmidt et al., "Trans-2-Phenylcyclopropylamine is a Mechanism-Based Inactivator of the Histone Demethylase LSD1," Biochemistry, 46(14):4408-4416 (2007).
Schulte et al., "Lysine-Specific Demethylase 1 is Strongly Expressed in Poorly Differentiated Neuroblastoma: Implications for Therapy," Cancer Research, 69(5):2065-2071 (2009).
Scoumanne et al. "Protein Methylation: A New Mechanism of p53 Tumor Suppressor Regulation," Histology and Histopathology, 23:1143-1149 (2008).
Scoumanne et al., "The Lysine-Specific Demethylase 1 is Required for Cell Proliferation in Both p53-Dependent and -Independent Manners," Journal of Biological Chemistry, 282(21):15471-15475 (2007).
Seligson et al., "Global Histone Modification Patterns Predict Risk of Prostate Cancer Recurrence," Nature, 435:1262-1266 (2005).
Seligson et al.,"Global Levels of Histone Modifications Predict Prognosis in Different Cancers," American Journal of Pathology, 174:1619-28 (2009).
Sharma et al., "(Bis)urea and (bis)thiourea Inhibitors of Lysine-Specific Demethylase 1 as Epigenetic Modulators," Journal of Medicinal Chemistry, 53(14):5197-5212, PMID 20568780 (2010).
Shi et al.,"Histone Demethylation Mediated by the Nuclear Amine Oxidase Homolog LSD1," Cell, 119:941-953 (2004).
Stephens et al., "The Determination of the Absolute Configurations of Chiral Molecules Using Vibrational Circular Dichroism (VCD) Spectroscopy," Chirality, 20:643-663 (2008).
Stoffel et al., "Leukocyte Count and Risk of Thrombosis in Patients Undergoing Haematopoietic Stem Cell Transplantation or Intensive Chemotherapy," Thrombosis Haemostasis, 103(6):1228-32 (2010).
Stratmann et al., "Pathobiology and Cell Interactions of Platelets in Diabetes," Diabetes & Vascular Disease Research, 2(1):16-23 (2005).
Szewczuk et al., "Mechanistic Analysis of a Suicide Inactivator of Histone Demethylase LSD1," Biochemistry, 46:6892-6902 (2007).
Tamagawa-Mineoka et al., "Elevated Platelet Activation in Patients With Atopic Dermatitis and Psoriasis: Increased Plasma Levels of Beta-Thromboglobulin and Platelet Factor 4," Allergology International, 57:391-396 (2008).
Taylor et al.,"Roscovitine, a Cyclin-Dependent Kinase Inhibitor, Prevents Replication of Varicella-Zoster Virus," Journal of Virology, 78:2853-2862 (2004).
Thaulow et al., "Blood Platelet Count and Function are Related to Total and Cardiovascular Death in Apparently Healthy Men," Circulation, 84(2):613-617 (1991).
Ueda et al., "Identification of Cell-Active Lysine Specific Demethylase 1-Selective Inhibitors," Journal of American Chemical Society, 131(48):17536-17537 (2009).
Wagner et al., "Platelets in inflammation and thrombosis," Arteriosclerosis, Thrombosis and Vascular Biology, 23:2131-2137 (2003).
Wang et al. "Novel Histone Demethylase LSD1 Inhibitors Selectively Target Cancer Cells With Pluripotent Stem Cell Properties," Cancer Research, doi:10.1158/0008-5472.CAN-11-0896 (2011).
Wang et al. "LSD1 is a Subunit of the NuRD Complex and Targets the Metastasis Programs in Breast Cancer," Cell 138:660-672 (2009).
Wang et al., "The Lysine Demethylase LSD1 (KDM1) is Required for Maintenance of Global DNA Methylation," Nature Genetics, 41(1):125-129 (2009).
Weinreb et al., "Novel Neuroprotective Mechanism of Action of Rasagiline is Associated With Its Propargyl Moiety: Interaction of Bcl-2 Family Members With PKC Pathway," Annals of the New York Academy of Sciences, 1053:348-355 (2005).
Wermuth, "Molecular Variations Based on Isosteric Replacements," The Practice of Medicinal Chemistry (2nd edition), Chpt 2, Academic Press, London, 203-237 (2003).
Westland et al. , "N-Substituted Derivatives of 2-Aminoethanethiol and 2-Hydraxinoethanethiol," Journal of Medicinal Chemistry, 11(4):824-829 (1968).
Whitlow et al.,"Recruitment of the Transcriptional Coactivator HCF-1 to Viral Immediate-Early Promoters During Initiation of Reactivation From Latency of Herpes Simplex Virus Type 1," Journal of Virology, 83(18):9591-9595, epub 0:JV1.01115-09v1 (2009).
Willoughby et al., "Platelets and Cardiovascular Disease," European Journal of Cardiovascular Nursing, 1:273-288 (2002).
XP002568777 Database Chemcats, Database Accession No. 2088922753, Order No. kbsb-0063197, Aurora Screening Library, Aug. 20, 2009.

(56) References Cited

OTHER PUBLICATIONS

Yang et al. "Structural Basis for the Inhibition of the LSD1 Histone Demethylase by the Antidepressant Trans-2-Phenylcyclopropylamine," Biochemistry, 46 (27):8058-8065 (2007).
Yang et al. "Structural Basis of Histone Demethylation by LSD1 Revealed by Suicide Inactivation," Nature Structural & Molecular Biology, 14(6):535-539 (2007).
Yoshida et al., "Fluorinated Phenylcyclopropylamines. Part 3: Inhibition of Monoamine Oxidase A and B," Bioorganic & Medicinal Chemistry, 12(10):2645-2652 (2004).
Bolesov et al., "Cyclopropanes and Cyclobutanes LXVIII," Zhurnal Organicheskoi Khimii (English Translation), 10(10)1678-1684 (1975).
M. Nabil Aboul-Enein et al, "Synthesis of some 4-substituted amino-1-methylpiperidines structurally related to antihistaminics", Pharmaceutica Acta Helvetiae, 1973, 48(3): 151-156.
J Vagner et al, "Peptidomimetics, a synthetic tool of drug discovery", Current Opinion on Chemical Biology, 2008, 12:292-296.
O. Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies. Part 2", Bioorg Med Chem Lett 2011, 21(15), 4429-4435.
J Kim et al, "Flavin chemical models for monoamine oxidase inactivation by cyclopropylamines, α-silylamines, and hydrazines", J Am Chem Soc 1995, 117, 100-105.
F. Zaragoza Dörwald, "Side reactions in organic synthesis: A Guide to successful synthesis design", Chapter 1 (Organic synthesis:General remarks), 2005, Wiley-VCH Verlag GmbH & Co KgaA, Weinheim.
CAS Registry No. RN903487-42-3, entered STN Aug. 23, 2006.
CAS Registry No. RN1251130-23-0, entered STN Nov. 3, 2010.
CAS Registry No. RN1281596-19-7, entered STN Apr. 17, 2011.
CAS Registry No. RN1281615-78-8, entered STN Apr. 17, 2011.
CAS Registry No. RN1282425-35-7, entered STN Apr. 19, 2011.
CAS Registry No. RN220351-33-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN1218057-33-0, entered STN Apr. 11, 2010.
Co-pending U.S. Appl. No. 13/066,616 (Publication No. 2011-0263604 A1), 371(c) date Apr. 18, 2011, now issued as US Patent No. 8,524,717.
Co-pending U.S. Appl. No. 13/138,413 (Publication No. 2012-0004262 A1), 371(c) date Sep. 12, 2011.
Co-pending U.S. Appl. No. 13/497,994 (Publication No. 2012-0283266 A1), 371(c) date Jul. 27, 2012.
Co-pending U.S. Appl. No. 13/580,553 (Publication No. 2013-0274267 A1), 371(c) date Jan. 4, 2013.
Co-pending U.S. Appl. No. 13/580,710 (Publication No. 2013-0095067 A1), 371(c) date Jan. 4, 2013.
Co-pending U.S. Appl. No. 13/641,916 (Publication No. 2013-0090386 A1), 371(c) date Dec. 21, 2012.
Co-pending U.S. Appl. No. 13/812,366 (Publication No. 2013-0231342 A1), 371(c) date May 13, 2013.
Co-pending U.S. Appl. No. 13/812,386 (Publication No. 2013-0197013 A1), 371(c) date Apr. 4, 2013.
Co-pending U.S. Appl. No. 13/876,485 (Publication No. 2013-0303545 A1), 371(c) date Jul. 26, 2013.
Co-pending U.S. Appl. No. 13/877,919 (Publication No. 2013-0289076 A1), 371(c) date Jul. 15, 2013.
Co-pending U.S. Appl. No. 13/983,844, 371(c) date Feb. 20, 2014.
Co-pending U.S. Appl. No. 14/1183,323, national stage entry Nov. 18, 2013.
Co-pending U.S. Appl. No. 14/118,330, national stage entry Nov. 18, 2013.
Co-pending U.S. Appl. No. 14/096,557, filed Dec. 4, 2013.
Co-pending U.S. Appl. No. 14/184,745, filed Feb. 20, 2014.
Johnson et al. CAPLUS, Document No. 157:576967, "Preparation of cyclopropylamines as LSD1 inhibitors in the treatment of cancer", 2012.
Delorme et al. HCAPLUS, Document No. 132:49802, "Preparation of 1-(N-substituted aminomethyl)-4-guanidinomethylcyclohexanes useful in pain management", 1999.
International Preliminary Report on Patentability of PCT/EP2010/055103, dated Apr. 11, 2012.
Bolesov et al, "Cyclopropanes and cyclobutanes LXVIII. N-mono and N,N-disubstituted 1-amino-2-phenylcyclopropanes",Zhurnal Organicheskoi Khimii (English Translation), 1974, 10(6), 1678-84.
Shi, "Histone lysine demethylases: emerging roles in development, physiology and disease", Nature reviews Genetics 2007, 8:829-833.
Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.
"Definition of Cancer"—MedicineNetcom Medical references for patients, http://www.medterms.com, 2005.
Co-pending U.S. Appl. No. 14/228,083, filed Mar. 27, 2014.
Co-pending U.S. Appl. No. 14/352,711, filed Apr. 18, 2014.
Co-pending U.S. Appl. No. 14/352,719, filed Apr. 18, 2014.

\* cited by examiner

SUBSTITUTED HETEROARYL- AND ARYL-CYCLOPROPYLAMINE ACETAMIDES AND THEIR USE

CROSS-REFERENCE TO RELATED PATENT APPLICATIONS

This application is the U.S. National Phase of PCT/EP2010/055103, filed Apr. 19, 2010, which claims priority to European Patent Application 09172705.7, filed Oct. 9, 2009, which is incorporated herein by reference in entirety.

FIELD OF THE INVENTION

The invention relates to compounds and their use in therapy.

BACKGROUND OF THE INVENTION

Cancer is prevalent: there were about 3.2 million cancer cases diagnosed (53% men, 47% women) and 1.7 million deaths from cancer (56% men, 44% women) in Europe (Ferlay et al. (2007) *Ann. Oncol.* 18(3):581-92). In the United States, the probability of developing invasive cancer is 38% for females and 46% for males that live to be 70 years old and older. In the US about 1.4 million new cases of cancer are expected for 2006. Although the five year survival rate for cancer is now 65%, up from about 50% in the mid-nineteen seventies, cancer is deadly. It is estimated that 565,000 people in the United States will die from cancer in 2006 (American Cancer Society, Surveillance Research, 2006). Despite tremendous advances in cancer treatment and diagnosis, cancer remains a major public health concern. Accordingly, there is a need for new therapeutics with activity in cancer.

Another health crisis is facing industrialized nations. As the population in these countries age, neurodegenerative diseases are affecting more and more people, posing a tremendous economic burden to national health systems. Alzheimer's disease is the largest neurodegenerative disease; disease modifying drugs have long been sought, but to-date, none have been identified. Other neurodegenerative conditions include Parkinson's disease, Huntington's disease, Lewy Body dementia, and which are all characterized by disease progression which robs the patients of their ability to perform normal daily activities, eventually leading to death.

One similar characteristic amongst many cancers and neurodegenerative diseases is aberrant gene expression. A number of compounds have been shown to alter gene expression, including histone deacetylase inhibitors which alter the histone acetylation profile of chromatin. Histone deacetylase inhibitors like SAHA, TSA, and many others have been shown to alter gene expression in various in vitro and in vivo animal models. Another modification that is involved in regulating gene expression is histone methylation. Histones can be subject to numerous modifications including lysine and arginine methylation. The methylation status of histone lysines has recently been shown to be important in dynamically regulating gene expression.

A group of enzymes known as histone lysine methyl transferases and histone lysine demethylases are involved histone lysine modifications. One particular human histone lysine demethylase enzyme called Lysine Specific Demethylase-1 (LSD1) was recently discovered (Shi et al. (2004) *Cell* 119: 941) to be involved in this crucial histone modification. Inactivation of LSD1 in *Drosophila* (dLSD1) strongly affects the global level of mono and dimethyl-H3-K4 methylation but not methyl-H3K9 while the levels of some other histone methylation and acetylation marks remained the same. dLSD1 inactivation resulted in elevated expression of a subset of genes, including neuronal genes in non-neuronal cells analogous to the functions of LSD1 in human cells. In *Drosophila*, dLsd1 is not an essential gene, but animal viability is strongly reduced in mutant animals in a gender specific manner (Destefano et al. (2007) *Curr Biol.* 17(9):808-12). Mouse homozygous LSD1 knock-outs were embryonic lethal.

LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds. Recent experiments with LSD1 have shown that it is involved in diverse process such as carcinogenesis (Kahl et al. (2006) *Cancer Res.* 66:1341-11347) and vascular inflammation (Reddy et al. (2008) *Circ. Res.* 103:615). It was found that a commercially available antidepressant, Parnate®, which targets monoamine oxidase (MAO), also inhibits LSD1 at clinically relevant concentrations (Lee et al. (2006) *Chem. Biol.* 13:563-567). Schmidt et al. found "$IC_{50}$ values for 2-PCPA of 20.7±2.1 µM for LSD1, 2.3±0.2 µM for MAO A, and 0.95±0.07 µM for MAO B." See Schmidt et al. (2007) *Biochemistry* 46(14)4408-4416. Thus, Parnate (2-PCPA) is a better inhibitor of MAO-A and MAO-B as compared to LSD1. Schmidt et al. note that the inhibition constants for irreversible inhibitors of LSD1 like parnate can greatly depend on assay conditions. Additionally, derivatives of Parnate also can inhibit LSD1 (Gooden et al. (2008) *Bioorg. Med. Chem. Let.* 18:3047-3051). Another class of compounds was recently disclosed to inhibit LSD1 activity: polyamines (Huang et al. (2007) PNAS 104:8023-8028). These polyamines inhibit LSD1 modestly and were shown to cause the re-expression of genes aberrantly silenced in cancer cells.

LSD1 is also involved in regulating the methylation of lysines of some proteins which are not histones, like P53 and DNMT1 which both have critical roles in cancer (Huang et al. (2007) *Nature* 449:105-108 and Wang et al. (2009) *Nature Genetics* 41(1):125-129).

Lee et al. ((2006) *Chem. Biol.* 13:563-567) reported that tranylcypromine inhibits histone H3K4 demethylation and can derepress Egr1 gene expression in some cancer lines. A body of evidence is accumulating that Egr-1 is a tumor suppressor gene in many contexts. Calogero et al. ((2004) *Cancer Cell International* 4:1) reported that Egr-1 is downregulated in brain cancers and exogenous expression of Egr-1 resulted in growth arrest and eventual cell death in primary cancer cell lines. Lucerna et al. ((2006) *Cancer Research* 66, 6708-6713) showed that sustained expression of Egr-1 causes antiangiogeneic effects and inhibits tumor growth in some models. Ferraro et al. ((2005) *J Clin Oncol.* March 20; 23(9):1921-6) reported that Egr-1 is downregulated in lung cancer patients with a higher risk of recurrence and may be more resistant to to therapy. Scoumanne et al. ((2007) *J Biol Chem.* May 25; 282(21):15471-5) observed that LSD1 is required for cell proliferation. They found that deficiency in LSD1 leads to a partial cell cycle arrest in G2/M and sensitizes cells to growth suppression induced by DNA damage. Kahl et al. ((2006) *Cancer Res.* 66(23):11341-7) found that LSD1 expression is correlated with prostate cancer aggressiveness. Metzger et al. ((2005) *Nature* 15; 437(7057):436-9) reported that LSD1 modulation by siRNA and pargyline regulates androgen receptor (AR) and may have therapeutic potential in cancers where AR plays a role, like prostate, testis, and brain cancers. Thus, a body of evidence has implicated LSD1 in a number of cancers, which suggests that LSD1 is a therapeutic target for cancer.

The phenylcyclopropylamines have been the subject of many studies designed to elucidate a SAR for MAO inhibition. Kaiser et al. ((1962) *J. Med. Chem.* 5:1243-1265); Zirkle et al. ((1962) *J. Med. Chem.* 1265-1284; U.S. Pat. Nos. 3,365, 458; 3,471,522; 3,532,749) have disclosed the synthesis and activity of a number of phenylcyclopropylamine related compounds. Zirkle et al. ((1962) *J. Med. Chem.* 1265-1284) reported that mono- and disubstitution of the amino group of trans-2-phenylcyclopropylamine with methyl decreases the activity only slightly whereas monosubstitution with larger groups like alkyl and araalkyl groups results in considerable loss of activity in the tryptamine potentiation assay for MAO activity. Studies have also been conducted with phenylcyclopropylamine related compounds to determine selectivity for MAO-A versus MAO-B since MAO-A inhibitors can cause dangerous side-effects (see e.g., Yoshida et al. (2004) *Bioorg. Med Chem.* 12(10):2645-2652; Hruschka et al. (2008) *Biorg Med Chem.* (16):7148-7166; Folks et al. (1983) *J. Clin. Psychopharmacol.* (3)249; and Youdim et al. (1983) *Mod. Probl. Pharmacopsychiatry* (19):63). Other phenylcyclopropylamine type compounds are disclosed in Bolesov et al. ((1974) *Zhurnal Organicheskoi Khimii* 10:8 1661-1669), Russian Patent No. 230169 (19681030), and WO 2009/117515. Gooden et al. ((2008) *Bioorg. Med. Chem. Let.* 18:3047-3051) describe the synthesis of phenylcyclopropylamines derivatives and analogs as well as their activity against MAO-A, MAO-B, and LSD1.

MAO inhibitors are clinically approved for treating depression and the neurodegenerative disease Parkinson's disease. Some studies report neuroprotective effects for MAO-B inhibitors. Rasagiline (N-propargyl-1R-aminoindan) is a highly potent, irreversible monoamine oxidase (MAO)-B was shown to have neuroprotective properties in various models. Studies have indicated that Rasagiline and other propargyl containing MAO-B inhibitors effect mitochondrial permeability, cytochrome c release, caspase activation, and additionally increase the levels of important neurotrophic factors like BDNF (Bar-Am et al. FASEB J. 2005 November; 19(13): 1899-901; Weinreb et al. Ann NY Acad Sci. 2005 August; 1053:348-55; Weinreb et al. J Neural Transm Suppl. 2006; (70):457-65). Han et al. (2009) Eur J Pharmacol. 604(1-3): 36-44 show that tranylcypromine attenuated the MPP(+)-induced cell death that may be associated with mitochondrial membrane permeability change and oxidative stress. Thus, MAO-B inhibitors are being investigated for their neuroprotective properties in neurodegenerative diseases like Alzheimer's disease, dementia, Lewy Body diseases, and motor neuron diseases such as ALS.

Interestingly, recovering of learning and memory is associated with changes in histone marks. Fischer et al. (2007) Nature 447, 178-182 show that learning and memory is associated with increases in H3K4me2 levels. LSD1, which is involved in regulating H3K4 methylation levels, has been shown to be part of the REST/CoREST complex involved in regulation of gene expression. Imbalances and/or alterations to the complex and/or members of the complex have been associated with numerous neurogenerative conditions like Huntington Disease, Parkinson's Disease, and Alzheimer's disease. Furthermore, several HDAC isoforms are part of the REST/CoREST complex. Interestingly, HDAC inibitors have been shown to have neuroprotective effects in many model systems.

In view of the lack of adequate treatments for conditions such as neurodegenerative disorders like Alzheimer's disease, Parkinson's disease, Lewy Body Dementia, Hunting-ton's disease, Dementia, and Frontal Temporal Dementia there is a desperate need for new drugs and drugs that work by inhibiting novel targets. Additionally, new methods and compounds are needed for treating cancer.

BRIEF SUMMARY OF THE INVENTION

The present invention relates to the identification of compounds and their use in treating and/or preventing diseases. The present invention provides a compound of Formula (I) or a pharmaceutically acceptable salt or solvate thereof, pharmaceutical compositions comprising a compound of Formula (I) or a pharmaceutically acceptable salt or solvate thereof, and a pharmaceutically acceptable carrier, and their uses for treating diseases. One use of the compound of Formula (I) is for treating neurodegenerative disorders. Another use for the compound of Formula (I) is to inhibit LSD1. Additionally it has been found that the compounds of the invention selectively inhibit MAO-B as compared to MAO-A. Compounds of Formula (I) have monoamine oxidase B inhibition activity and therefore can be used to treat diseases like Parkinson's disease as well as other neurodegenerative conditions, and depression. Compounds of Formula (I) have LSD1 inhibition activity and therefore can be used to treat diseases like cancer.

In one aspect, the invention provides a compound of Formula (I) or a pharmaceutically acceptable salt or solvate thereof:

$(A')_X$-(A)-(B)—(Z)-(L)-C(=O)NH$_2$  (I)

wherein:
(A) is heteroaryl or aryl;
each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2 or 3 substituents independently chosen from halo, haloalkyl, aryl, arylalkoxy, alkyl, alkoxy, cyano, sulfonyl, sulfinyl, and carboxamide;
X is 0, 1, 2, or 3;
(B) is a cyclopropyl ring, wherein (A) and (Z) are covalently bonded to different carbon atoms of (B);
(Z) is —NH—; and
(L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl;
provided that, if (L) is —CH$_2$— or —CH(CH$_3$)—, then X is not 0.

In a preferred embodiment of this aspect, the compound of Formula (I) is a compound of Formula (II). Accordingly, the invention provides a compound of Formula (II) or a pharmaceutically acceptable salt or solvate thereof:

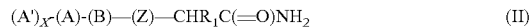

$(A')_X$-(A)-(B)—(Z)—CHR$_1$C(=O)NH$_2$  (II)

wherein:
(A) is heteroaryl or aryl covalently bonded to (B) and to (A'), if present;
Each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to a hydrogen atom, and to —CHR$_1$C(=O) NH$_2$; and R$_1$ is a hydrogen atom or a C$_1$-C$_6$ alkyl group;
provided that, if R$_1$ is hydrogen or methyl, then X is not 0.

In a further preferred embodiment of this aspect, the invention provides a compound of Formula (II) or a pharmaceutically acceptable salt or solvate thereof:

(II)

wherein:
(A) is heteroaryl or aryl covalently bonded to (B) and to (A'), if present;
Each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(=O) NH$_2$; and R$_1$ is a hydrogen atom or a C$_1$-C$_6$ alkyl group.

In a second aspect, the invention provides a pharmaceutical composition comprising a compound of Formula (I) or a pharmaceutically acceptable salt or solvate thereof as defined above (or a compound of Formula (II) or a pharmaceutically acceptable salt or solvate thereof as defined above) and a pharmaceutically acceptable carrier.

In a third aspect, the invention provides a method of treating and/or preventing a disease or condition comprising administering, to a subject/patient (preferably, a human) in need of treatment or prevention, a therapeutically effective amount of a composition comprising a compound of Formula (I) or a pharmaceutically acceptable salt or solvate thereof and a pharmaceutically acceptable carrier (or, accordingly, a composition comprising a compound of Formula (II) or a pharmaceutically acceptable salt or solvate thereof and a pharmaceutically acceptable carrier). This aspect can be formulated as a compound of Formula (I) for use as a medicament (or accordingly, a compound of Formula (II) for use as a medicament).

In a fourth aspect, the invention provides a method of inhibiting LSD1 and/or MAO-B activity comprising administering, to a subject/patient (preferably, a human) in need of treatment, an amount of a composition comprising a compound of Formula (I) or a pharmaceutically acceptable salt or solvate thereof and a pharmaceutically acceptable carrier (or, accordingly, a composition comprising a compound of Formula (II) or a pharmaceutically acceptable salt or solvate thereof and a pharmaceutically acceptable carrier), in an amount sufficient to inhibit LSD1 and MAO-B activity. This aspect can be formulated as a compound of Formula (I) or a pharmaceutically acceptable salt or solvate thereof (or, accordingly, a compound of Formula (II) or a pharmaceutically acceptable salt or solvate thereof) as an inhibitor of LSD1 and/or MAO-B activity. This aspect can also be formulated as a compound of Formula (I) or a pharmaceutically acceptable salt or solvate thereof (or accordingly, a compound of Formula (II) or a pharmaceutically acceptable salt or solvate thereof) for use in the treatment and/or prevention of a neurodegenerative disease, depression and/or cancer. Preferably, the neurodegenerative disease is chosen from Parkinson's disease, Alzheimer's disease, Dementia with Lewy Bodies, Frontotemporal Dementia, Vascular Dementia, and Huntington disease. Preferably, the cancer is chosen from prostate, breast, colorectal, lung, brain, testicular, kidney and blood cancer.

In a fifth aspect, the invention provides a method of inhibiting monoamine oxidase B activity comprising administering, to a subject/patient (preferably, a human) in need of treatment, an amount of a pharmaceutical composition comprising a compound of Formula (I) or a pharmaceutically acceptable salt or solvate thereof, and a pharmaceutically acceptable carrier (or, accordingly, a pharmaceutical composition comprising a compound of Formula (II) or a pharmaceutically acceptable salt or solvate thereof, and a pharmaceutically acceptable carrier) sufficient to inhibit monoamine oxidase B activity. This aspect can be formulated as a compound of Formula (I) or a pharmaceutically acceptable salt or solvate thereof (or, accordingly, a compound of Formula (II) or a pharmaceutically acceptable salt or solvate thereof) for use in treating and/or preventing a neurodegenerative disease and/or depression. Preferably, the neurodegenerative disease is chosen from Parkinson's disease, Alzheimer's disease, Dementia with Lewy Bodies, Frontotemporal Dementia, Vascular Dementia, and Huntington disease.

In a sixth aspect, the invention provides a method of treating and/or preventing a neurodegenerative disease or disorder comprising administering, to a subject/patient (preferably, a human) in need of treatment or prevention, a therapeutically effective amount of a pharmaceutical composition comprising a compound of Formula (I) or a pharmaceutically acceptable salt or solvate thereof, and a pharmaceutically acceptable carrier (or, accordingly, a pharmaceutical composition comprising a compound of Formula (II) or a pharmaceutically acceptable salt or solvate thereof, and a pharmaceutically acceptable carrier). This aspect can be formulated as a compound of Formula (I) or a pharmaceutically acceptable salt or solvate thereof (or, accordingly, a compound of Formula (II) or a pharmaceutically acceptable salt or solvate thereof), for use in treating and/or preventing a neurodegenerative disorder or condition. Preferably, the neurodegenerative disorder or condition is chosen from Parkinson's disease, Alzheimer's disease, Dementia with Lewy Bodies, Frontotemporal Dementia, Vascular Dementia, and Huntington disease.

In a seventh aspect, the invention provides a method of inhibiting LSD1 activity comprising administering, to a subject/patient (preferably, a human) in need of treatment, an amount of a pharmaceutical composition comprising a compound of Formula (I) or a pharmaceutically acceptable salt or solvate thereof, and a pharmaceutically acceptable carrier (or, accordingly, a pharmaceutical composition comprising a compound of Formula (II) or a pharmaceutically acceptable salt or solvate thereof, and a pharmaceutically acceptable carrier) sufficient to inhibit LSD1 activity. This aspect can be formulated as a compound of Formula (I) for inhibiting LSD1 for treating and/or preventing cancer. This aspect can be also formulated as the use of a compound of Formula (I) for the manufacture of a medicament for the treatment and/or prevention of cancer by inhibiting LSD1. This aspect can further be formulated as a compound of Formula (I) or a pharmaceutically acceptable salt or solvate thereof (or, accordingly, a compound of Formula (II) or a pharmaceutically acceptable salt or solvate thereof) for use in the treatment and/or prevention of cancer. The invention also relates to a pharmaceutical composition comprising a compound of Formula (I) or a pharmaceutically acceptable salt or solvate thereof and a pharmaceutically acceptable carrier (or, accordingly, a pharmaceutical composition comprising a compound of Formula (II) or a pharmaceutically acceptable salt or solvate thereof and a pharmaceutically acceptable carrier) for use in the treatment and/or prevention of cancer. Furthermore, the invention encompasses a method of treating and/or preventing cancer comprising administering, to a subject/patient (preferably, a human) in need of treatment or prevention, a therapeutically effective amount of a pharmaceutical composition comprising a compound of Formula (I) or a pharmaceutically acceptable salt or solvate thereof, and a pharmaceutically acceptable carrier (or, accordingly, a compound of Formula (II) or a pharmaceutically acceptable salt or solvate thereof, and a pharmaceutically acceptable carrier). Preferably, the cancer is chosen from prostate, breast, colorectal, lung, brain, testicular, kidney and blood cancer. In one embodiment, the cancer is prostate cancer. In another embodiment, the cancer is breast cancer. In another embodiment, the cancer is colorectal cancer. In another embodiment, the cancer is lung cancer. In another embodiment, the cancer is testicular cancer. In another embodiment, the cancer is blood cancer. In another embodiment, the cancer is kidney cancer.

The invention provides a pharmaceutical composition comprising a compound of Formula (I) or a pharmaceutically acceptable salt or solvate thereof (or accordingly, a compound of Formula (II) or a pharmaceutically acceptable salt or solvate thereof), which is a selective inhibitor of LSD1 and MAO-B as compared to MAO-A, and a pharmaceutically acceptable carrier.

The inventors have found compounds of Formula (I) (and compounds of Formula (II)) unexpectedly inhibit LSD1 and/or MAO-B, and many of which are potent inhibitors of both enzymes. LSD1/MAO-B selective inhibitors have Ki values for LSD1 and MAO-B which are at least 2-fold lower than the Ki value for MAO-A. In one aspect of this embodiment, the LSD1 Ki value is at least 5-fold lower than the Ki value for MAO-A. In one aspect of this embodiment, the MAO-B Ki value is at least 5-fold lower than the Ki value for MAO-A. In one aspect of this embodiment, the LSD1 and MAO-B Ki values are at least 5-fold lower than the Ki value for MAO-A. In one aspect of this embodiment, the LSD1 Ki value is at least 10-fold lower than the Ki value for MAO-A. In one aspect of this embodiment, the MAO-B Ki value is at least 10-fold lower than the Ki value for MAO-A. In one aspect of this embodiment, the LSD1 and MAO-B Ki values are at least 10-fold lower than the Ki value for MAO-A.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The present invention relates to the identification of compounds and their use in treating and preventing diseases. The present invention provides a compound of Formula (I), pharmaceutical compositions comprising a compound of Formula (I) or a pharmaceutically acceptable salt or solvate thereof, and a pharmaceutically acceptable carrier, and their uses for treating diseases. One use of the compounds of Formula (I) is for treating neurodegenerative disease and/or depression. Many compounds of the invention inhibit monoamine oxidase B selectively as compared to monoamine oxidase A, and can therefore be used for diseases in which monoamine oxidase inhibition B is useful. For example, many of the compounds of Formula (I) are at least 5-10 fold more potent for inhibiting MAO-B as compared to MAO-A. The inventors have elucidated that substituted aryl- and heteroarylcyclopropylamine derivatives of Formula (I) and, in particular, substituted aryl- and heteroarylcyclopropylamine acetamides of Formula (II) are unexpectedly potent inhibitors of two biologically relevant targets, LSD1 and MAO-B. Furthermore, the compounds of Formula (I), as shown in the Examples, inhibit LSD1 and MAO-B to a greater extent than MAO-A. The Examples described herein show that compounds of Formula (I) have values for LSD1 inhibition under 1 micromolar (see Table 1) which makes them about at least 40-50-fold more potent than tranylcypromine for LSD1 inhibition. Some compounds of the invention are LSD1 selective inhibitors which inhibit LSD1 to greater extent than MAO-A and MAO-B.

In a first aspect, the invention provides a compound of Formula (I) or a pharmaceutically acceptable salt or solvate thereof:

$$(A')_X\text{-}(A)\text{-}(B)\text{---}(Z)\text{-}(L)\text{-}C(=O)NH_2 \quad (I)$$

(A) is heteroaryl or aryl.
Each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2 or 3 substituents independently chosen from halo, haloalkyl, aryl, arylalkoxy, alkyl, alkoxy, cyano, sulfonyl, sulfinyl, and carboxamide.
X is 0, 1, 2, or 3.
(B) is a cyclopropyl ring, wherein (A) and (Z) are covalently bonded to different carbon atoms of (B).
(Z) is —NH—.
(L) is —$(CH_2)_m CR_1 R_2$— wherein m is 0, 1, 2, 3, 4, 5, or 6 and wherein $R_1$ and $R_2$ are each independently hydrogen or $C_1$-$C_6$ alkyl. If (L) is —$CH_2$— or —$CH(CH_3)$—, then X is not 0.

In one embodiment of this first aspect, the invention provides a compound of Formula (I) or a pharmaceutically acceptable salt or solvate thereof, wherein:
(A) is aryl;
each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, sulfinyl, and carboxamide;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; and
(L) is —$(CH_2)_m CR_1 R_2$— wherein m is 0, 1, 2, 3, 4, 5, or 6 and wherein $R_1$ and $R_2$ are each independently hydrogen or $C_1$-$C_6$ alkyl; if (L) is —$CH_2$— or —$CH(CH_3)$—, then X is not 0.

In one embodiment of this first aspect, the invention provides a compound of Formula (I) or a pharmaceutically acceptable salt or solvate thereof, wherein:
(A) is phenyl;
each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, sulfinyl, and carboxamide;
X is 0, 1, 2, or 3;

(B) is a cyclopropyl ring which is covalently bonded to (A) and to (Z), wherein (A) and (Z) are covalently bonded to different carbon atoms of (B);

(Z) is —NH—; and (L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl; if (L) is —CH$_2$— or —CH(CH$_3$)—, then X is not 0.

In one embodiment of this first aspect, the invention provides a compound of Formula (I) or a pharmaceutically acceptable salt or solvate thereof, wherein:

X is 1 or 2;

(A) is heteroaryl or aryl covalently bonded to (B) and to (A'), if present;

each (A') is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, sulfinyl, and carboxamide;

(B) is a cyclopropyl ring which is covalently bonded to (A) and to (Z), wherein (A) and (Z) are covalently bonded to different carbon atoms of (B);

(Z) is —NH—; and (L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl; if (L) is —CH$_2$— or —CH(CH$_3$)—, then X is not 0.

In one embodiment of this first aspect, the invention provides a compound of Formula (I) or a pharmaceutically acceptable salt or solvate thereof, wherein:

X is 1;

(A') is chosen from aryl, arylalkoxy, arylalkyl, and aryloxy, wherein said aryl, arylalkoxy, arylalkyl, or aryloxy has 0 or 1 substituent chosen from halo, haloalkyl, and cyano;

(A) is heteroaryl or aryl covalently bonded to (B) and to (A');

(B) is a cyclopropyl ring which is covalently bonded to (A) and to (Z), wherein (A) and (Z) are covalently bonded to different carbon atoms of (B);

(Z) is —NH—; and (L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl; if (L) is —CH$_2$— or —CH(CH$_3$)—, then X is not 0.

In one embodiment of this first aspect, the invention provides a compound of Formula (I) or a pharmaceutically acceptable salt or solvate thereof, wherein:

X is 1;

(A') is chosen from phenyl, benzyl, and benzyloxy, wherein said phenyl, benzyl, or benzyloxy has 0 or 1 substituent chosen from halo, haloalkyl, and cyano;

(A) is heteroaryl or aryl covalently bonded to (B) and to (A');

(B) is a cyclopropyl ring which is covalently bonded to (A) and to (Z), wherein (A) and (Z) are covalently bonded to different carbon atoms of (B);

(Z) is —NH—; and (L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl; if (L) is —CH$_2$— or —CH(CH$_3$)—, then X is not 0.

In one embodiment of this first aspect, the invention provides a compound of Formula (I) or a pharmaceutically acceptable salt or solvate thereof, wherein:

(L) is —CR$_1$R$_2$—, wherein R$_1$ and R$_2$ are each independently hydrogen or C$_1$-C$_6$ alkyl;

(A) is heteroaryl or aryl covalently bonded to (B) and to (A'), if present;

each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, sulfinyl, and carboxamide;

X is 0, 1, 2, or 3;

(B) is a cyclopropyl ring which is covalently bonded to (A) and to (Z), wherein (A) and (Z) are covalently bonded to different carbon atoms of (B);

(Z) is —NH—;

provided that, if (L) is —CH$_2$— or —CH(CH$_3$)—, then X is not 0.

In one embodiment of this first aspect, the invention provides a compound of Formula (I) or a pharmaceutically acceptable salt or solvate thereof, wherein:

(L) is —CH$_2$—;

(A) is heteroaryl or aryl covalently bonded to (B) and to (A'), if present;

each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, sulfinyl, and carboxamide;

X is 1, 2, or 3;

(B) is a cyclopropyl ring which is covalently bonded to (A) and to (Z), wherein (A) and (Z) are covalently bonded to different carbon atoms of (B);

(Z) is —NH—.

In one embodiment of this first aspect, the invention provides a compound of Formula (I) or a pharmaceutically acceptable salt or solvate thereof, wherein:

(A) is heteroaryl covalently bonded to (B) and to (A'), if present;

each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, sulfinyl, and carboxamide;

X is 0, 1, 2, or 3;

(B) is a cyclopropyl ring which is covalently bonded to (A) and to (Z), wherein (A) and (Z) are covalently bonded to different carbon atoms of (B);

(Z) is —NH—; and (L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl; if (L) is —CH$_2$— or —CH(CH$_3$)—, then X is not 0.

In one embodiment of the first aspect, the invention provides a compound of Formula (I) or a pharmaceutically acceptable salt or solvate thereof, wherein:

(A) is heteroaryl covalently bonded to (B) and to (A'), if present, wherein said heteroaryl is chosen from pyridyl, pyrimidinyl, and thiophenyl;

each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, sulfinyl, and carboxamide;

X is 0, 1, 2, or 3;

(B) is a cyclopropyl ring which is covalently bonded to (A) and to (Z), wherein (A) and (Z) are covalently bonded to different carbon atoms of (B);

(Z) is —NH—; and (L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl; if (L) is —CH$_2$— or —CH(CH$_3$)—, then X is not 0.

In one embodiment of the first aspect, the invention provides a compound of Formula (I) wherein:

(B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B);

(A) is heteroaryl or aryl covalently bonded to (B) and to (A'), if present;

Each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, sulfinyl, and carboxamide;

X is 0, 1, 2, or 3;

(B) is a cyclopropyl ring which is covalently bonded to (A) and to (Z), wherein (A) and (Z) are covalently bonded to different carbon atoms of (B);

(Z) is —NH—; and (L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl; if (L) is —CH$_2$— or —CH(CH$_3$)—, then X is not 0.

In one embodiment of the first aspect, the invention provides a compound of Formula (I) or a pharmaceutically acceptable salt or solvate thereof, wherein:

X is 1;

(A) is phenyl;

(A') is covalently bonded to (A) in the para position in respect of the cyclopropyl ring (B), i.e., (A') is para to the cyclopropyl ring (B) substituting the (A) phenyl, and (A') is chosen from aryl, arylalkoxy, arylalkyl, heterocyclyl, aryloxy, halo, alkoxy, haloalkyl, cycloalkyl, haloalkoxy, and cyano, wherein (A') is substituted with 0, 1, 2, or 3 substituents independently chosen from halo, haloalkyl, aryl, arylalkoxy, alkyl, alkoxy, cyano, sulfonyl, sulfinyl, and carboxamide;

(B) is a cyclopropyl ring which is covalently bonded to (A) and to (Z), wherein (A) and (Z) are covalently bonded to different carbon atoms of (B);

(Z) is —NH—; and (L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl.

In one embodiment of the first aspect, the invention provides a compound of Formula (I) or a pharmaceutically acceptable salt or solvate thereof, wherein:

each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 3 substituents independently chosen from halo, haloalkyl, aryl, arylalkoxy, alkyl, alkoxy, cyano, sulfonyl, sulfinyl, and carboxamide; and X, (A), (B), (Z), and (L) have the meanings defined above in respect of the compound of Formula (I), including the above embodiments of the first aspect.

In one specific embodiment of the first aspect, the invention provides a compound of Formula (I) or a pharmaceutically acceptable salt or solvate thereof:

$$(A')_X\text{-(A)-(B)—(Z)-(L)-C(=O)NH}_2 \quad \text{(I)}$$

wherein (A'), X, (A), (B), (Z), and (L) have the meanings or preferred meanings defined in the following:

(A) is heteroaryl or aryl.

Said heteroaryl is preferably chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, and 2-oxobenzimidazolyl. More preferably, said heteroaryl is chosen from pyridyl, pyrimidinyl, and thiophenyl. Even more preferably, said heteroaryl is pyridyl. Still even more preferably, said heteroaryl is pyridin-3-yl (i.e., said heteroaryl is a pyridine group which is attached via its 3-position to the cyclopropyl ring (B)).

Said aryl is preferably chosen from phenyl, naphthalenyl, and anthracenyl. More preferably, said aryl is phenyl.

Preferably, (A) is aryl. More preferably, (A) is phenyl, naphthalenyl, or anthracenyl. Even more preferably, (A) is phenyl.

Each (A'), if present, is indepedently chosen from aryl, arylalkoxy, arylalkyl, heterocyclyl, aryloxy, halo, alkoxy, haloalkyl, cycloalkyl, haloalkoxy, and cyano; preferably, each (A'), if present, is indepedently chosen from aryl, arylalkoxy, arylalkyl, and aryloxy; more preferably, each (A'), if present, is indepedently chosen from phenyl, benzyl, and benzyloxy.

Furthermore, each (A') is substituted with 0, 1, 2 or 3 substituents (preferably, 0, 1, or 2 substituents; more preferably, 0 or 1 substituent) independently chosen from halo, haloalkyl, aryl, arylalkoxy, alkyl, alkoxy, cyano, sulfonyl, sulfinyl, and carboxamide. Preferably, said substituents are independently chosen from halo, haloalkyl, aryl, arylalkoxy, alkyl, alkoxy, cyano, sulfonyl, and sulfinyl; more preferably, said substituents are independently chosen from halo, haloalkyl, and cyano.

Preferably, each (A'), if present, is indepedently chosen from aryl, arylalkoxy, arylalkyl, and aryloxy, wherein said aryl, arylalkoxy, arylalkyl, or aryloxy has 0 or 1 substituent chosen from halo, haloalkyl, and cyano. More preferably, each (A'), if present, is indepedently chosen from phenyl, benzyl, and benzyloxy, wherein said phenyl, benzyl, or benzyloxy has 0 or 1 substituent chosen from halo, haloalkyl, and cyano.

It is preferred that (A') is covalently bonded to (A) in the para position in respect of the cyclopropyl ring (B).

X is 0, 1, 2, or 3.

Preferably, X is 1, 2, or 3. More preferably, X is 1 or 2. Even more preferably, X is 1.

(B) is a cyclopropyl ring, wherein (A) and (Z) are covalently bonded to different carbon atoms of (B).

It is preferred that (A) and (Z) are in the trans orientation with respect to the cyclopropyl ring (B).

(Z) is —NH—.

(L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl.

It is preferred that said (L) in the position alpha to the —C(=O)NH$_2$ group is substituted (corresponding to R$_1$ and R$_2$) with one or two C$_1$-C$_6$ alkyl groups, more preferably with one or two C$_1$-C$_3$ alkyl groups (i.e., it is preferred that R$_1$ and R$_2$ are each independently C$_1$-C$_6$ alkyl; more preferably, R$_1$ and R$_2$ are each independently C$_1$-C$_3$ alkyl). Accordingly, the (L) group may be, e.g., —(CH$_2$)$_2$C(C$_1$-C$_3$ alkyl)(C$_1$-C$_3$ alkyl)-, —(CH$_2$)$_3$C(C$_1$-C$_3$ alkyl)(C$_1$-C$_3$ alkyl)-, —(CH$_2$)$_3$CH(CH$_2$CH$_3$)—, —(CH$_2$)$_2$C(CH$_3$)$_2$—, —(CH$_2$)$_3$C(CH$_3$)$_2$—, —(CH$_2$)$_3$CH(CH$_3$)—, —(CH$_2$)$_2$CH(CH$_3$)—, —(CH$_2$)$_3$C(CH$_3$)$_2$—, —(CH$_2$)$_3$CH(CH$_2$CH$_3$)—, or —(CH$_2$)$_2$CH(CH$_2$CH$_3$)—. Preferably m is 0, 1, 2, or 3.

(L) may, e.g., also preferably be a linear C$_1$-C$_6$ alkylene, such as —CH$_2$—, —(CH$_2$)$_2$—, —(CH$_2$)$_3$—, —(CH$_2$)$_4$—, —(CH$_2$)$_5$—, or —(CH$_2$)$_6$—.

More preferably, (L) is —CR$_1$R$_2$—, wherein R$_1$ and R$_2$ are each independently hydrogen or C$_1$-C$_6$ alkyl. Accordingly, (L) may, e.g., be —CH$_2$—, —CH(CH$_3$)— or —C(CH$_3$)$_2$—. Even more preferably, (L) is —CHR$_1$—, wherein R$_1$ is hydrogen or C$_1$-C$_6$ alkyl (i.e., R$_2$ is hydrogen). Even more preferably, (L) is —CHR$_1$—, wherein R$_1$ is C$_1$-C$_6$ alkyl.

If (L) is —CH$_2$— or —CH(CH$_3$)—, then X is not 0.

In accordance with this specific embodiment, the invention also provides the compound of formula (I) as described and defined herein above or a pharmaceutically acceptable salt or solvate thereof for use as a medicament. Accordingly, the invention encompasses a pharmaceutical composition comprising the compound of formula (I) as described and defined herein above or a pharmaceutically acceptable salt or solvate thereof, and a pharmaceutically acceptable carrier. The invention further relates to the compound of formula (I) as described and defined herein above or a pharmaceutically acceptable salt or solvate thereof for use in treating and/or preventing cancer. Said cancer is preferably chosen from prostate cancer, breast cancer, colorectal cancer, lung cancer, brain cancer, testicular cancer, kidney cancer, and blood cancer. Moreover, the invention relates to the compound of formula (I) as described and defined herein above or a pharmaceutically acceptable salt or solvate thereof for use in treating and/or preventing a neurodegenerative disease/disorder or depression. Said neurodegenerative disease is preferably chosen from Parkinson's disease, Alzheimer's disease, dementia with Lewy bodies, frontotemporal dementia, vascular dementia, and Huntington disease.

In a further specific embodiment of the first aspect, the invention provides a compound of Formula (I) or a pharmaceutically acceptable salt or solvate thereof:

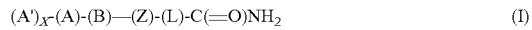

(A')$_X$-(A)-(B)—(Z)-(L)-C(=O)NH$_2$     (I)

wherein (A'), X, (A), (B), (Z), and (L) have the meanings or preferred meanings defined in the following:
(A) is heteroaryl or aryl.

Said heteroaryl is preferably chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, and 2-oxobenzimidazolyl. More preferably, said heteroaryl is chosen from pyridyl, pyrimidinyl, and thiophenyl. Even more preferably, said heteroaryl is pyridyl. Still even more preferably, said heteroaryl is pyridin-3-yl (i.e., said heteroaryl is a pyridine group which is attached via its 3-position to the cyclopropyl ring (B)).

Said aryl is preferably chosen from phenyl, naphthalenyl, and anthracenyl. More preferably, said aryl is phenyl.

Preferably, (A) is heteroaryl. More preferably, (A) is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, and 2-oxobenzimidazolyl. Even more preferably, (A) is chosen from pyridyl, pyrimidinyl, and thiophenyl. Yet even more preferably, (A) is a pyridyl group. Yet still even more preferably, (A) is a pyridyl group wherein the cyclopropyl ring (B) is at the 3 position with respect to the ring nitrogen (which is position 1) of the pyridyl group.

Each (A'), if present, is indepedently chosen from aryl, arylalkoxy, arylalkyl, heterocyclyl, aryloxy, halo, alkoxy, haloalkyl, cycloalkyl, haloalkoxy, and cyano; preferably, each (A'), if present, is indepedently chosen from aryl, arylalkoxy, arylalkyl, and aryloxy; more preferably, each (A'), if present, is indepedently chosen from phenyl, benzyl, and benzyloxy.

Furthermore, each (A') is substituted with 0, 1, 2 or 3 substituents (preferably, 0, 1, or 2 substituents; more preferably, 0 or 1 substituent) independently chosen from halo, haloalkyl, aryl, arylalkoxy, alkyl, alkoxy, cyano, sulfonyl, sulfinyl, and carboxamide. Preferably, said substituents are independently chosen from halo, haloalkyl, aryl, arylalkoxy, alkyl, alkoxy, cyano, sulfonyl, and sulfinyl; more preferably, said substituents are independently chosen from halo, haloalkyl, and cyano.

Preferably, each (A'), if present, is indepedently chosen from aryl, arylalkoxy, arylalkyl, and aryloxy, wherein said aryl, arylalkoxy, arylalkyl, or aryloxy has 0 or 1 substituent chosen from halo, haloalkyl, and cyano. More preferably, each (A'), if present, is indepedently chosen from phenyl, benzyl, and benzyloxy, wherein said phenyl, benzyl, or benzyloxy has 0 or 1 substituent chosen from halo, haloalkyl, and cyano.

It is preferred that (A') is covalently bonded to (A) in the para position in respect of the cyclopropyl ring (B).
X is 0, 1, 2, or 3.

Preferably, X is 1, 2, or 3. More preferably, X is 1 or 2. Even more preferably, X is 1.

(B) is a cyclopropyl ring, wherein (A) and (Z) are covalently bonded to different carbon atoms of (B).

It is preferred that (A) and (Z) are in the trans orientation with respect to the cyclopropyl ring (B).
(Z) is —NH—.
(L) is —(CH$_2$)$_m$CR$_1$R$_2$— wherein m is 0, 1, 2, 3, 4, 5, or 6 and wherein R$_1$ and R$_2$ are each independently hydrogen or C$_1$-C$_6$ alkyl.

It is preferred that said (L) in the position alpha to the —C(═O)NH$_2$ group is substituted (corresponding to R$_1$ and R$_2$) with one or two C$_1$-C$_6$ alkyl groups, more preferably with one or two C$_1$-C$_3$ alkyl groups (i.e., it is preferred that R$_1$ and R$_2$ are each independently C$_1$-C$_6$ alkyl; more preferably, R$_1$ and R$_2$ are each independently C$_1$-C$_3$ alkyl). Accordingly, the (L) group may be, e.g., —(CH$_2$)$_2$C(C$_1$-C$_3$ alkyl)(C$_1$-C$_3$ alkyl)-, —(CH$_2$)$_3$C(C$_1$-C$_3$ alkyl)(C$_1$-C$_3$ alkyl)-, —(CH$_2$)$_3$CH(CH$_2$CH$_3$)—, —(CH$_2$)$_2$C(CH$_3$)$_2$—, —(CH$_2$)$_3$C(CH$_3$)$_2$—, —(CH$_2$)$_3$CH(CH$_3$)—, —(CH$_2$)$_2$CH(CH$_3$)—, —(CH$_2$)$_3$C(CH$_3$)$_2$—, —(CH$_2$)$_3$CH(CH$_2$CH$_3$)—, or —(CH$_2$)$_2$CH(CH$_2$CH$_3$)—. Preferably m is 0, 1, 2, or 3.

(L) may, e.g., also preferably be a linear C$_1$-C$_6$ alkylene, such as —CH$_2$—, —(CH$_2$)$_2$—, —(CH$_2$)$_3$—, —(CH$_2$)$_4$—, —(CH$_2$)$_5$—, or —(CH$_2$)$_6$—.

More preferably, (L) is —CR$_1$R$_2$—, wherein R$_1$ and R$_2$ are each independently hydrogen or C$_1$-C$_6$ alkyl. Accordingly, (L) may, e.g., be —CH$_2$—, —CH(CH$_3$)— or —C(CH$_3$)$_2$—. Even more preferably, (L) is —CHR$_1$—, wherein R$_1$ is hydrogen or C$_1$-C$_6$ alkyl (i.e., R$_2$ is hydrogen). Even more preferably, (L) is —CHR$_1$—, wherein R$_1$ is C$_1$-C$_6$ alkyl.

If (L) is —CH$_2$— or —CH(CH$_3$)—, then X is not 0.

In accordance with this specific embodiment, the invention also provides the compound of formula (I) as described and defined herein above or a pharmaceutically acceptable salt or solvate thereof for use as a medicament. Accordingly, the invention encompasses a pharmaceutical composition comprising the compound of formula (I) as described and defined herein above or a pharmaceutically acceptable salt or solvate thereof, and a pharmaceutically acceptable carrier. The invention further relates to the compound of formula (I) as described and defined herein above or a pharmaceutically acceptable salt or solvate thereof for use in treating and/or preventing cancer. Said cancer is preferably chosen from prostate cancer, breast cancer, colorectal cancer, lung cancer, brain cancer, testicular cancer, kidney cancer, and blood cancer. Moreover, the invention relates to the compound of formula (I) as described and defined herein above or a pharmaceutically acceptable salt or solvate thereof for use in treating and/or preventing a neurodegenerative disease/disorder or depression. Said neurodegenerative disease is preferably chosen from Parkinson's disease, Alzheimer's disease, dementia with Lewy bodies, frontotemporal dementia, vascular dementia, and Huntington disease.

In one embodiment of this first aspect, the compound of Formula (I) is a compound of Formula (II).

Accordingly, the invention provides a compound of Formula (II) or a pharmaceutically acceptable salt or solvate thereof:

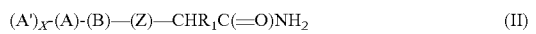

(A')$_X$-(A)-(B)—(Z)—CHR$_1$C(═O)NH$_2$     (II)

wherein:
(A) is heteroaryl or aryl covalently bonded to (B) and to (A'), if present;
Each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(═O)NH$_2$; and R$_1$ is a hydrogen or a C$_1$-C$_6$ alkyl group, provided that, if R$_1$ is hydrogen or methyl, then X is not 0. In a related aspect, the invention provides a pharmaceutical composition comprising a compound of Formula (II) as defined above or a pharmaceutically acceptable salt or solvate thereof and a pharmaceutically acceptable carrier.

In one embodiment of this first aspect, the invention provides a compound of Formula (II) or a pharmaceutically acceptable salt or solvate thereof, wherein:
(A) is aryl;
each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to a hydrogen atom, and to —CHR$_1$C(═O) NH$_2$; and
R$_1$ is a hydrogen or a C$_1$-C$_6$ alkyl group, provided that, when R$_1$ is —H or methyl, then X is not 0.

In one embodiment of this first aspect, the invention provides a compound of Formula (II) or a pharmaceutically acceptable salt or solvate thereof, wherein:
(A) is phenyl;
each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to a hydrogen atom, and to —CHR$_1$C(═O) NH$_2$; and
R$_1$ is a hydrogen or a C$_1$-C$_6$ alkyl group, provided that, when R$_1$ is —H or methyl, then X is not 0.

In one embodiment of this first aspect, the invention provides a compound of Formula (II) or a pharmaceutically acceptable salt or solvate thereof, wherein:
X is 1 or 2;
(A) is heteroaryl or aryl covalently bonded to (B) and to (A'), if present;
Each (A') is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to a hydrogen atom, and to —CHR$_1$C(═O) NH$_2$; and
R$_1$ is a hydrogen or a C$_1$-C$_6$ alkyl group.

In one embodiment of this first aspect, the invention provides a compound of Formula (II) or a pharmaceutically acceptable salt or solvate thereof, wherein:

X is 1;
(A') is chosen from aryl, arylalkoxy, arylalkyl, and aryloxy, wherein said aryl, arylalkoxy, arylalkyl, or aryloxy has 0 or 1 substituent chosen from halo, haloalkyl, and cyano;
(A) is heteroaryl or aryl covalently bonded to (B) and to (A');
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(=O)NH$_2$; and
R$_1$ is a hydrogen or a C$_1$-C$_6$ alkyl group.

In one embodiment of this first aspect, the invention provides a compound of Formula (II) or a pharmaceutically acceptable salt or solvate thereof, wherein:
X is 1;
(A') is chosen from phenyl, benzyl, and benzyloxy, wherein said phenyl, benzyl, or benzyloxy has 0 or 1 substituent chosen from halo, haloalkyl, and cyano;
(A) is heteroaryl or aryl covalently bonded to (B) and to (A');
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(=O)NH$_2$; and
R$_1$ is a hydrogen or a C$_1$-C$_6$ alkyl group.

In one embodiment of this first aspect, the invention provides a compound of Formula (II) or a pharmaceutically acceptable salt or solvate thereof, wherein:
R$_1$ is a C$_1$-C$_6$ alkyl group;
(A) is heteroaryl or aryl covalently bonded to (B) and to (A'), if present;
Each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(=O)NH$_2$, provided that when R$_1$ is methyl then X is not 0.

In one embodiment of this first aspect, the invention provides a compound of Formula (II) or a pharmaceutically acceptable salt or solvate thereof, wherein:
R$_1$ is a hydrogen;
(A) is heteroaryl or aryl covalently bonded to (B) and to (A'), if present;
each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(=O)NH$_2$; and
R$_1$ is a hydrogen.

In one embodiment of this first aspect, the invention provides a compound of Formula (II) or a pharmaceutically acceptable salt or solvate thereof, wherein:
(A) is heteroaryl covalently bonded to (B) and to (A'), if present;
each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(=O)NH$_2$; and
R$_1$ is a hydrogen or a C$_1$-C$_6$ alkyl group, provided that, when R$_1$ is —H or methyl, then X is not 0.

In one embodiment of the first aspect, the invention provides a compound of Formula (II) or a pharmaceutically acceptable salt or solvate thereof, wherein:
(A) is heteroaryl covalently bonded to (B) and to (A'), if present, wherein said heteroaryl is chosen from pyridyl, pyrimidinyl, and thiophenyl;
each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(=O)NH$_2$; and
R$_1$ is a hydrogen or a C$_1$-C$_6$ alkyl group, provided that, when R$_1$ is —H or methyl, then X is not 0.

In one embodiment of the first aspect, the invention provides a compound of Formula (II) wherein:
(B) is a cyclopropyl ring which is covalently bonded to (A) and to (Z), wherein (A) and (Z) are covalently bonded to different carbon atoms of (B), and wherein (A) and (Z) are in the trans orientation with respect to the cyclopropyl ring (B);
(A) is heteroaryl or aryl covalently bonded to (B) and to (A'), if present;
Each (A'), if present, is indepedently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(=O)NH$_2$; and
R$_1$ is a hydrogen or a C$_1$-C$_6$ alkyl group, provided that, when R$_1$ is —H or methyl, then X is not 0.

In one embodiment of the first aspect, the invention provides a compound of Formula (II) or a pharmaceutically acceptable salt or solvate thereof, wherein:

X is 1;
(A) is phenyl;
(A') is covalently bonded to (A) in the para position in respect of the cyclopropyl ring (B), i.e., (A') is para to the cyclopropyl ring (B) substituting the (A) phenyl, and (A') is chosen from aryl, arylalkoxy, arylalkyl, heterocyclyl, aryloxy, halo, alkoxy, haloalkyl, cycloalkyl, haloalkoxy, and cyano, wherein (A') is substituted with 0, 1, or 2 substituents independently chosen from halo, haloalkyl, aryl, arylalkoxy, alkyl, alkoxy, cyano, sulfonyl, and sulfinyl;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to a hydrogen atom, and to —CHR$_1$C(=O)NH$_2$; and
R$_1$ is a hydrogen or a C$_1$-C$_6$ alkyl group.

The invention further provides a compound of Formula (II) or a pharmaceutically acceptable salt or solvate thereof:

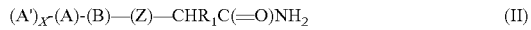

(A')$_X$-(A)-(B)—(Z)—CHR$_1$C(=O)NH$_2$      (II)

wherein:
(A) is heteroaryl or aryl covalently bonded to (B) and to (A'), if present;
Each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 1, 2, or 3;
(B) is a cyclopropyl ring which is covalently bonded to (A) and to (Z), wherein (A) and (Z) are covalently bonded to different carbon atoms of (B);
(Z) is —NH—; accordingly (Z) is a nitrogen atom covalently bonded to (B), to a hydrogen atom, and to —CHR$_1$C(=O)NH$_2$; and
R$_1$ is a C$_1$-C$_6$ alkyl group.

In a related aspect, the invention provides a pharmaceutical composition comprising a compound of Formula (II) as defined above or a pharmaceutically acceptable salt or solvate thereof and a pharmaceutically acceptable carrier. In one subembodiment, preferably R$_1$ is a methyl group. In another subembodiment, preferably R$_1$ is an ethyl group.

In one specific embodiment of the first aspect, the invention provides a compound of Formula (II) or a pharmaceutically acceptable salt or solvate thereof:

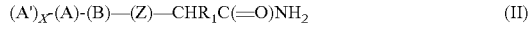

(A')$_X$-(A)-(B)—(Z)—CHR$_1$C(=O)NH$_2$      (II)

wherein (A'), X, (A), (B), (Z), and R$_1$ have the meanings or preferred meanings defined in the following:
(A) is heteroaryl or aryl.

Said heteroaryl is preferably chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, and 2-oxobenzimidazolyl. More preferably, said heteroaryl is chosen from pyridyl, pyrimidinyl, and thiophenyl. Even more preferably, said heteroaryl is pyridyl. Still even more preferably, said heteroaryl is pyridin-3-yl (i.e., said heteroaryl is a pyridine group which is attached via its 3-position to the cyclopropyl ring (B)).

Said aryl is preferably chosen from phenyl, naphthalenyl, and anthracenyl. More preferably, said aryl is phenyl.

Preferably, (A) is aryl. More preferably, (A) is phenyl, naphthalenyl, or anthracenyl. Even more preferably, (A) is phenyl.

Each (A'), if present, is indepedently chosen from aryl, arylalkoxy, arylalkyl, heterocyclyl, aryloxy, halo, alkoxy, haloalkyl, cycloalkyl, haloalkoxy, and cyano; preferably, each (A'), if present, is indepedently chosen from aryl, arylalkoxy, arylalkyl, and aryloxy; more preferably, each (A'), if present, is indepedently chosen from phenyl, benzyl, and benzyloxy.

Furthermore, each (A') is substituted with 0, 1, 2 or 3 substituents (preferably, 0, 1, or 2 substituents; more preferably, 0 or 1 substituent) independently chosen from halo, haloalkyl, aryl, arylalkoxy, alkyl, alkoxy, cyano, sulfonyl, sulfinyl, and carboxamide. Preferably, said substituents are independently chosen from halo, haloalkyl, aryl, arylalkoxy, alkyl, alkoxy, cyano, sulfonyl, and sulfinyl; more preferably, said substituents are independently chosen from halo, haloalkyl, and cyano.

Preferably, each (A'), if present, is indepedently chosen from aryl, arylalkoxy, arylalkyl, and aryloxy, wherein said aryl, arylalkoxy, arylalkyl, or aryloxy has 0 or 1 substituent chosen from halo, haloalkyl, and cyano. More preferably, each (A'), if present, is indepedently chosen from phenyl, benzyl, and benzyloxy, wherein said phenyl, benzyl, or benzyloxy has 0 or 1 substituent chosen from halo, haloalkyl, and cyano.

It is preferred that (A') is covalently bonded to (A) in the para position in respect of the cyclopropyl ring (B).
X is 0, 1, 2, or 3.

Preferably, X is 1, 2, or 3. More preferably, X is 1 or 2. Even more preferably, X is 1.
(B) is a cyclopropyl ring, wherein (A) and (Z) are covalently bonded to different carbon atoms of (B).

It is preferred that (A) and (Z) are in the trans orientation with respect to the cyclopropyl ring (B).
(Z) is —NH—.
R$_1$ is hydrogen or C$_1$-C$_6$ alkyl. Preferably, R$_1$ is hydrogen or methyl. If R$_1$ is hydrogen or methyl, then X is not 0.

In accordance with this specific embodiment, the invention also provides the compound of formula (II) as described and defined herein above or a pharmaceutically acceptable salt or solvate thereof for use as a medicament. Accordingly, the invention encompasses a pharmaceutical composition comprising the compound of formula (II) as described and defined herein above or a pharmaceutically acceptable salt or solvate thereof, and a pharmaceutically acceptable carrier. The invention further relates to the compound of formula (II) as described and defined herein above or a pharmaceutically acceptable salt or solvate thereof for use in treating and/or preventing cancer. Said cancer is preferably chosen from prostate cancer, breast cancer, colorectal cancer, lung cancer, brain cancer, testicular cancer, kidney cancer, and blood cancer. Moreover, the invention relates to the compound of formula (II) as described and defined herein above or a pharmaceutically acceptable salt or solvate thereof for use in treating and/or preventing a neurodegenerative disease/disorder or depression. Said neurodegenerative disease is preferably chosen from Parkinson's disease, Alzheimer's disease, dementia with Lewy bodies, frontotemporal dementia, vascular dementia, and Huntington disease.

In a further specific embodiment of the first aspect, the invention provides a compound of Formula (II) or a pharmaceutically acceptable salt or solvate thereof:

$$(A')_X\text{-}(A)\text{-}(B)\text{---}(Z)\text{---}CHR_1C(\!=\!O)NH_2 \quad (II)$$

wherein (A'), X, (A), (B), (Z), and $R_1$ have the meanings or preferred meanings defined in the following:
(A) is heteroaryl or aryl.

Said heteroaryl is preferably chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, and 2-oxobenzimidazolyl. More preferably, said heteroaryl is chosen from pyridyl, pyrimidinyl, and thiophenyl. Even more preferably, said heteroaryl is pyridyl. Still even more preferably, said heteroaryl is pyridin-3-yl (i.e., said heteroaryl is a pyridine group which is attached via its 3-position to the cyclopropyl ring (B)).

Said aryl is preferably chosen from phenyl, naphthalenyl, and anthracenyl. More preferably, said aryl is phenyl.

Preferably, (A) is heteroaryl. More preferably, (A) is chosen from thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl, and 2-oxobenzimidazolyl. Even more preferably, (A) is chosen from pyridyl, pyrimidinyl, and thiophenyl. Yet even more preferably, (A) is a pyridyl group. Yet still even more preferably, (A) is a pyridyl group wherein the cyclopropyl ring (B) is at the 3 position with respect to the ring nitrogen (which is position 1) of the pyridyl group.

Each (A'), if present, is indepedently chosen from aryl, arylalkoxy, arylalkyl, heterocyclyl, aryloxy, halo, alkoxy, haloalkyl, cycloalkyl, haloalkoxy, and cyano; preferably, each (A'), if present, is indepedently chosen from aryl, arylalkoxy, arylalkyl, and aryloxy; more preferably, each (A'), if present, is indepedently chosen from phenyl, benzyl, and benzyloxy.

Furthermore, each (A') is substituted with 0, 1, 2 or 3 substituents (preferably, 0, 1, or 2 substituents; more preferably, 0 or 1 substituent) independently chosen from halo, haloalkyl, aryl, arylalkoxy, alkyl, alkoxy, cyano, sulfonyl, sulfinyl, and carboxamide. Preferably, said substituents are independently chosen from halo, haloalkyl, aryl, arylalkoxy, alkyl, alkoxy, cyano, sulfonyl, and sulfinyl; more preferably, said substituents are independently chosen from halo, haloalkyl, and cyano.

Preferably, each (A'), if present, is indepedently chosen from aryl, arylalkoxy, arylalkyl, and aryloxy, wherein said aryl, arylalkoxy, arylalkyl, or aryloxy has 0 or 1 substituent chosen from halo, haloalkyl, and cyano. More preferably, each (A'), if present, is indepedently chosen from phenyl, benzyl, and benzyloxy, wherein said phenyl, benzyl, or benzyloxy has 0 or 1 substituent chosen from halo, haloalkyl, and cyano.

It is preferred that (A') is covalently bonded to (A) in the para position in respect of the cyclopropyl ring (B).
X is 0, 1, 2, or 3.

Preferably, X is 1, 2, or 3. More preferably, X is 1 or 2. Even more preferably, X is 1.
(B) is a cyclopropyl ring, wherein (A) and (Z) are covalently bonded to different carbon atoms of (B).

It is preferred that (A) and (Z) are in the trans orientation with respect to the cyclopropyl ring (B).
(Z) is —NH—.
$R_1$ is hydrogen or $C_1$-$C_6$ alkyl. Preferably, $R_1$ is hydrogen or methyl. If $R_1$ is hydrogen or methyl, then X is not 0.

In accordance with this specific embodiment, the invention also provides the compound of formula (II) as described and defined herein above or a pharmaceutically acceptable salt or solvate thereof for use as a medicament. Accordingly, the invention encompasses a pharmaceutical composition comprising the compound of formula (II) as described and defined herein above or a pharmaceutically acceptable salt or solvate thereof, and a pharmaceutically acceptable carrier. The invention further relates to the compound of formula (II) as described and defined herein above or a pharmaceutically acceptable salt or solvate thereof for use in treating and/or preventing cancer. Said cancer is preferably chosen from prostate cancer, breast cancer, colorectal cancer, lung cancer, brain cancer, testicular cancer, kidney cancer, and blood cancer. Moreover, the invention relates to the compound of formula (II) as described and defined herein above or a pharmaceutically acceptable salt or solvate thereof for use in treating and/or preventing a neurodegenerative disease/disorder or depression. Said neurodegenerative disease is preferably chosen from Parkinson's disease, Alzheimer's disease, dementia with Lewy bodies, frontotemporal dementia, vascular dementia, and Huntington disease.

In one embodiment of the first aspect, the invention provides a compound of Formula (I) or a compound of Formula (II), which compound is chosen from
2-((trans)-2-(4-(4-cyanobenzyloxy)phenyl)cyclopropylamino)acetamide,
2-((trans)-2-(4-(3-cyanobenzyloxy)phenyl)cyclopropylamino)acetamide,
2-((trans)-2-(4-(benzyloxy)phenyl)cyclopropylamino)acetamide,
2-((trans)-2-(4-(4-fluorobenzyloxy)phenyl)cyclopropylamino)acetamide,
2-((trans)-2-(4-(3-fluorobenzyloxy)phenyl)cyclopropylamino)acetamide,
2-((trans)-2-(4-(3-chlorobenzyloxy)phenyl)cyclopropylamino)acetamide,
2-((trans)-2-(4-(4-chlorobenzyloxy)phenyl)cyclopropylamino)acetamide, 2-((trans)-2-(4-(3-bromobenzyloxy)phenyl)cyclopropylamino)acetamide,
2-((trans)-2-(4-(3,5-difluorobenzyloxy)phenyl)cyclopropylamino)acetamide,
2-((trans)-2-(4-phenethoxyphenyl)cyclopropylamino)acetamide,
2-((trans)-2-(3'-(trifluoromethyl)biphenyl-4-yl)cyclopropylamino)acetamide, and
2-((trans)-2-(3'-chlorobiphenyl-4-yl)cyclopropylamino)acetamide,
or a pharmaceutically acceptable salt or solvate thereof.

In one embodiment of the first aspect, the invention provides a compound of Formula (I) or a compound of Formula (II) which compound is chosen from
2-((trans)-2-(6-(4-chlorophenyl)pyridin-3-yl)cyclopropylamino)acetamide,
(R)-2-((trans)-2-(4-(3-fluorobenzyloxy)phenyl)cyclopropylamino)propanamide,
(S)-2-((trans)-2-(4-(4-fluorobenzyloxy)phenyl)cyclopropylamino)propanamide,
(R)-2-((trans)-2-(4-(4-fluorobenzyloxy)phenyl)cyclopropylamino)propanamide,
(S)-2-((trans)-2-(4-(4-fluorobenzyloxy)phenyl)cyclopropylamino)propanamide,
(R)-2-((trans)-2-(4-(benzyloxy)phenyl)cyclopropylamino) propanamide,
(S)-2-((trans)-2-(4-(benzyloxy)phenyl)cyclopropylamino) propanamide,
2-(2-[1,1';4',1"]Terphenyl-4"-yl-cyclopropylamino)acetamide,
or a pharmaceutically acceptable salt or solvate thereof.

In one embodiment of the first aspect, the invention provides a compound of Formula (I) or a compound of Formula (II) which compound is chosen from
5'-((trans)-2-(2-amino-2-oxoethylamino)cyclopropyl)-2'-(benzyloxy)biphenyl-3-carboxamide,
5-((trans)-2-(4'-chlorobiphenyl-4-yl)cyclopropylamino)pentanamide,
3-((trans)-2-(4-(3-bromobenzyloxy)phenyl)cyclopropylamino)propanamide,
4-((trans)-2-phenylcyclopropylamino)butanamide,
5-((trans)-2-phenylcyclopropylamino)pentanamide,
or a pharmaceutically acceptable salt or solvate thereof.

In one embodiment of the first aspect, the invention provides a compound of Formula (I) which compound is chosen from
5-((trans)-2-(4'-chlorobiphenyl-4-yl)cyclopropylamino)-2-methylpentanamide,
4-((trans)-2-(4'-chlorobiphenyl-4-yl)cyclopropylamino)-2-methylbutanamide,
3-((trans)-2-(4-(3-fluorobenzyloxy)phenyl)cyclopropylamino)-2,2-dimethylpropanamide,
3-((trans)-2-(4'-chlorobiphenyl-4-yl)cyclopropylamino)propanamide,
4-((trans)-2-(4'-chlorobiphenyl-4-yl)cyclopropylamino)butanamide,
4-((trans)-2-(4-(3-bromobenzyloxy)phenyl)cyclopropylamino)butanamide,
5-((trans)-2-(4-(3-bromobenzyloxy)phenyl)cyclopropylamino)pentanamide,
5-((trans)-2-(6-(benzyloxy)biphenyl-3-yl)cyclopropylamino)pentanamide,
4-((trans)-2-(6-(benzyloxy)biphenyl-3-yl)cyclopropylamino)butanamide,
or a pharmaceutically acceptable salt or solvate thereof.

Thus, the inventors have shown that the compounds having a general Formula (I) or (II) are potent inhibitors of LSD1.

Many of the compounds of the invention are potent inhibitors of LSD1 and MAO-B as compared to MAO-A as illustrated in the examples. The general structure of compounds of Formula (II) can be depicted as below

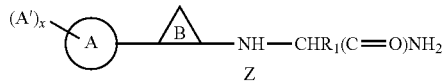

wherein:
(A) is heteroaryl or aryl covalently bonded to (B) and to (A'), if present;
Each (A'), if present, is indepedntly chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring which is covalently bonded to (A) and to (Z), wherein (A) and (Z) are covalently bonded to different carbon atoms of (B);
(Z) is —NH—; accordingly, Z is a nitrogen atom covalently bonded to (B), to a hydrogen atom, and to —CHR$_1$C(═O)NH$_2$; and
R$_1$ is a hydrogen or a C$_1$-C$_6$ alkyl group, provided that, when R$_1$ is —H or methyl, then X is not 0.

In a preferred aspect, the invention provides a compound of Formula (II) or a pharmaceutically acceptable salt thereof:

$$(A')_X\text{-}(A)\text{-}(B)\text{—}(Z)\text{—}CHR_1C(═O)NH_2 \qquad (II)$$

wherein:
(A) is heteroaryl or aryl covalently bonded to (B) and to (A');
Each (A') is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 1, 2, or 3;
(B) is a cyclopropyl ring which is covalently bonded to (A) and to (Z), wherein (A) and (Z) are covalently bonded to different carbon atoms of (B);
(Z) is —NH—; accordingly, (Z) is a nitrogen atom covalently bonded to (B), to a hydrogen atom, and to —CHR$_1$C(═O)NH$_2$; and
R$_1$ is a hydrogen atom or a C$_1$-C$_6$ alkyl group.

Another preferred subgroup of compounds of Forumla (II) is defined as follows:

$$(A')_X\text{-}(A)\text{-}(B)\text{—}(Z)\text{—}CHR_1C(═O)NH_2 \qquad (II)$$

wherein:
(A) is phenyl covalently bonded to (B) and to (A');
each (A') is indepedntly chosen from aryl, arylalkoxy, arylalkyl, heterocyclyl, and aryloxy, wherein each (A') is further substituted with 0, 1, or 2 substituents independently chosen from halo, haloalkyl, alkyl, alkoxy, cyano, sulfonyl, and sulfinyl;
X is 1, 2, or 3;
(B) is a cyclopropyl ring which is covalently bonded to (A) and to (Z), wherein (A) and (Z) are covalently bonded to different carbon atoms of (B);

(Z) is —NH—; accordingly, Z is a nitrogen atom covalently bonded to (B), to a hydrogen atom, and to —CHR$_1$C(=O)NH$_2$; and R$_1$ is a hydrogen.

In a second aspect, the invention provides a pharmaceutical composition comprising a compound as defined immediately above or a pharmaceutically acceptable salt thereof and a pharmaceutically acceptable carrier.

In a third aspect, the invention provides a method of treating and/or preventing a disease or condition comprising administering, to a subject/patient (preferably, a human) in need of treatment, a therapeutically effectively amount of a composition comprising a compound of Formula (I) or a pharmaceutically acceptable salt or solvate thereof and a pharmaceutically acceptable carrier (or, accordingly, a composition comprising a compound of Formula (II) or a pharmaceutically acceptable salt or solvate thereof and a pharmaceutically acceptable carrier). This aspect can be formulated as a compound of Formula (I) or a pharmaceutically acceptable salt or solvate thereof (or, accordingly, a compound of Formula (II) or a pharmaceutically acceptable salt or solvate thereof) for use as a medicament.

In a fourth aspect, the invention provides a method of inhibiting LSD1 and/or MAO-B activity comprising administering, to a subject/patient (preferably, a human) in need of treatment, an amount of a composition comprising a compound of Formula (I) or a pharmaceutically acceptable salt or solvate thereof and a pharmaceutically acceptable carrier (or, accordingly, a composition comprising a compound of Formula (II) or a pharmaceutically acceptable salt or solvate thereof and a pharmaceutically acceptable carrier), in an amount sufficient to inhibit LSD1 and MAO-B activity. This aspect can be formulated as a compound of Formula (I) (or, accordingly, a compound of Formula (II)) as a inhibitor of LSD1 and/or MAO-B activity. This aspect can also be formulated as a compound of Formula (I) (or, accordingly, a compound of Formula (II)) for use in the treatment and/or prevention of a neurodegenerative disease, depression and/or cancer. Preferably, the neurodegenerative disease is chosen from Parkinson's disease, Alzheimer's disease, Dementia with Lewy Bodies, Frontotemporal Dementia, Vascular Dementia, and Huntington disease. Preferably, the cancer is chosen from prostate, breast, colorectal, lung, brain, testicular, kidney and blood cancer.

In a fifth aspect, the invention provides a method of inhibiting monoamine oxidase B activity comprising administering, to a subject/patient (preferably, a human) in need of treatment, an amount of a pharmaceutical composition comprising a compound of Formula (I) or a pharmaceutically acceptable salt or solvate thereof, and a pharmaceutically acceptable carrier (or, accordingly, a composition comprising a compound of Formula (II) or a pharmaceutically acceptable salt or solvate thereof and a pharmaceutically acceptable carrier) sufficient to inhibit monoamine oxidase B activity. This aspect can be formulated as a compound of Formula (I) (or, accordingly, a compound of Formula (II)) for use in treating and/or preventing a neurodegenerative disease and/or depression. Preferably, the neurodegenerative disease is chosen from Parkinson's disease, Alzheimer's disease, Dementia with Lewy Bodies, Frontotemporal Dementia, Vascular Dementia, and Huntington disease.

In a sixth aspect, the invention provides a method of treating and/or preventing a neurodegenerative disease or disorder comprising administering, to a subject/patient (preferably, a human) in need of treatment, a therapeutically effectively amount of a pharmaceutical composition comprising a compound of Formula (I) or a pharmaceutically acceptable salt thereof, and a pharmaceutically acceptable carrier (or, accordingly, a pharmaceutical composition comprising a compound of Formula (II) or a pharmaceutically acceptable salt or solvate thereof and a pharmaceutically acceptable carrier). This aspect can be formulates as a compound of Formula (I) or a pharmaceutically acceptable salt or solvate thereof (or, accordingly, a compound of Formula (II) or a pharmaceutically acceptable salt or solvate thereof), for use in treating and/or preventing a neurodegenerative disorder or condition.

In a seventh aspect, the invention provides a method of inhibiting LSD1 activity comprising administering, to a subject/patient (preferably, a human) in need of treatment, an amount of a pharmaceutical composition comprising a compound of Formula (I) or a pharmaceutically acceptable salt or solvate thereof, and a pharmaceutically acceptable carrier (or, accordingly, a pharmaceutical composition comprising a compound of Formula (II) or a pharmaceutically acceptable salt or solvate thereof and a pharmaceutically acceptable carrier) sufficient to inhibit LSD1 activity. This aspect can be formulated as a compound of Formula (I) (or, accordingly, a compound of Formula (II) for inhibiting LSD1 for treating and/or preventing cancer. This aspect can be also formulated as a compound of Formula (I) or a pharmaceutically acceptable salt or solvate thereof (or, accordingly, a compound of Formula (II) or a pharmaceutically acceptable salt or solvate thereof) for use in the treatment and/or prevention of cancer. Preferably, the cancer is chosen from prostate, breast, colorectal, lung, brain, testicular, kidney and blood cancer. In one embodiment, the cancer is prostate cancer. In another embodiment, the cancer is breast cancer. In another embodiment, the cancer is colorectal cancer. In another embodiment, the cancer is lung cancer. In In another embodiment, the cancer is testicular cancer. In another embodiment, the cancer is blood cancer. In another embodiment, the cancer is kidney cancer.

The invention provides a pharmaceutical composition comprising a compound of Formula (I) or a pharmaceutically acceptable salt or solvate thereof (or, accordingly, a compound of Formula (II) or a pharmaceutically acceptable salt or solvate thereof), which is a selective inhibitor of LSD1 and MAO-B as compared to MAO-A, and a pharmaceutically acceptable carrier.

The invention provides a pharmaceutical composition comprising a compound of Formula (I) or a pharmaceutically acceptable salt or solvate thereof (or, accordingly, a compound of Formula (II) or a pharmaceutically acceptable salt or solvate thereof), which is a selective inhibitor of LSD1 and MAO-B, and a pharmaceutically acceptable carrier.

Thus the invention provides a method of treating or preventing a neurodegenerative disease or disorder comprising administering to a subject/patient (preferably, a human) a therapeutically effective amount of a compound of Formula (I) as defined above in any of the embodiments and aspects described above (or, accordingly, a compound of Formula (II) as defined above in any of the embodiments and aspects described above). Preferably the neurodegenerative disease or disorder is chosen from Parkinson's disease, Alzheimer's disease, Dementia with Lewy Bodies, Frontotemporal Dementia, Vascular Dementia, and Huntington disease.

The inventors have found compounds of Formula (I) (and compounds of Formula (II)) unexpectedly inhibit LSD1 and MAO-B, and are potent inhibitors of both enzymes. LSD1/MAO-B selective inhibitors have Ki values for LSD1 and MAO-B which are at least 2-fold lower than the Ki value for MAO-A. In one aspect of this embodiment, the LSD1 Ki value is at least 5-fold lower than the Ki value for MAO-A. In one aspect of this embodiment, the MAO-B Ki value is at least 5-fold lower than the Ki value for MAO-A. In one aspect of this embodiment, the LSD1 and MAO-B Ki values are at least 5-fold lower than the Ki value for MAO-A. In one aspect of this embodiment, the LSD1 Ki value is at least 10-fold lower than the Ki value for MAO-A. In one aspect of this embodiment, the MAO-B Ki value is at least 10-fold lower than the Ki value for MAO-A. In one aspect of this embodiment, the LSD1 and MAO-B Ki values are at least 10-fold lower than the Ki value for MAO-A.

It is to be understood that, if a group is defined to have 0 substituents selected from a number of substituents, then the respective group is not substituted with any substituent from this number of substituents but instead is substituted with hydrogen.

It is further to be understood that the group —(CH$_2$)$_m$CR$_1$R$_2$—, as described and defined herein, refers to either one of the following groups:

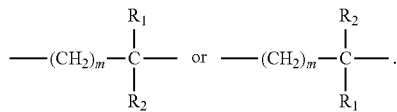

Definitions

As used herein, the term "alkyl" refers to a saturated aliphatic hydrocarbon including straight chain and/or branched chain groups having from 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms). Preferably, the "alkyl" has from 1 to 10 carbon atoms. More preferably, it is a lower alkyl having from 1 to 6 carbon atoms, and even more preferably 1 to 4 carbon atoms.

As used herein, the term "alkylene" refers to an alkanediyl group including straight chain and/or branched chain groups, i.e. to a divalent radical of an alkane, where an alkane is a saturated aliphatic hydrocarbon including straight chain and/or branched chain groups.

As used herein, the term "halo" refers to chloro, fluoro, bromo, and iodo.

As used herein, the term "hydro" refers to a hydrogen atom (—H group).

As used herein, the term "alkoxy" refers to an —O-alkyl group, wherein "alkyl" has the meaning provided above. Lower alkoxy refers to —O-lower alkyl groups, having the term "lower alkyl" the same meaning as above.

As used herein, the term "haloalkyl" refers to an alkyl group substituted with 1 to 6 halo groups. In a specific embodiment, haloalkyl is a —CX$_3$ group wherein X is a halo group. The halo groups can be independently selected. In a more specific embodiment, haloalkyl is a —CF$_3$ group.

As used herein, the term "haloalkoxy" refers to an alkoxy group substituted with 1 to 6 halo groups. In a specific embodiment, haloalkyl is a —OCX$_3$ group wherein X is a halo group. The halo groups can be independently selected. Preferably the halo is fluoro.

As used herein, the term "cyano" refers to a —C≡N group.

As used herein, the term "sulfinyl" refers to a —S(=O)R" group, with R" being a C$_1$-C$_6$ alkyl group.

As used herein, the term "sulfonyl" refers to a —S(=O)$_2$R" group, with R" as defined herein.

As used herein, the term "carbocycle", "carbocyclic" or "carbocyclyl" means a radical derived from one of the known all carbon ring or ring systems having ring or 2-4 fused rings (i.e., rings which share an adjacent pair of ring carbon atoms) which are saturated or partially unsaturated. When the "carbocycle", "carbocyclic" or "carbocyclyl" is part of a fused ring system each one of the rings forming said ring system is saturated or partially insaturated, and has 5-7 carbon atoms. Examples, without limitation, of "carbocycle", "carbocyclic" or "carbocyclyl" groups are cycloalkyls such as cyclopropane, cyclobutane, cyclopentane, cyclohexane, adamantane, cycloheptane and cycloalkenes such as cycloheptatriene, cyclopentene, and cyclohexadiene.

As used herein, the term "cycloalkyl" refers to a cyclic saturated aliphatic (i.e., non-aromatic) hydrocarbon group which does not comprise any carbon-to-carbon double bond or any carbon-to-carbon triple bond. Preferably, the cycloalkyl has 3 to 7 carbon atoms. Non-limiting examples of cycloalkyl groups are cyclopropyl, cyclobutyl, cyclopentyl, cyclohexyl or cycloheptyl.

As used herein, the term "heterocyclyl", "heterocyclyl" or heterocyclic" refers to a known saturated, partially saturated, or unsaturated 3-7 membered monocyclic ring, or known 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Non-limiting examples saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups. Example of "heterocyclyls" or "heterocyclic" rings also include, but are not limited to, morpholino, piperidyl, piperazinyl, pyrrolidinyl, thiomorpholino, homopiperazinyl, imidazolyl, imidazolidinyl, pyrazolidinyl, dioxanyl and dioxolanyl. "Heterocyclyl" can include heteroaryls when the pi-electron system of a heterocyclyl is completely conjugated (e.g., unsaturated).

As used herein, the term "aryl" is a radical derived from one of the known aromatic all carbon ring or ring systems having 2 to 4 fused rings, wherein each ring has from 5-6 carbon atoms. Examples, without limitation, of aryl groups are phenyl, naphthalenyl and anthracenyl.

As used herein, the term "aryloxy" refers to an —O-aryl, as defined herein.

As used herein, the term "heteroaryl" refers to a radical derived from one of the known aromatic rings or ring systems having from 2 to 4 fused rings, wherein at least one of the rings forming said ring system is aromatic (preferably, each one of the rings forming said ring system is aromatic), and has 5-6 members, being each member independently selected from C, CH, N, O, S, being at least one of the members of the ring or ring system an N, O, or S. Non-limiting examples of heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acrindinyl, perimidinyl, phenanthrolinyl, phenazinyl, isothiazolyl, phenothiazinyl, isoxazolyl, furazanyl, phenoxazinyl, isocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. When the heteroaryl group contains a nitrogen ring atom, such nitrogen ring atom may be in the form of an N-oxide, e.g., a pyridyl N-oxide, pyrazinyl N-oxide and pyrimidinyl N-oxide.

As used herein, the term "arylalkyl" refers to any of the $C_{1-10}$ alkyl groups substituted by any of the above-mentioned $C_{6-14}$ aryl groups as defined above. Non-limiting examples of arylalkyl group include benzyl, phenethyl, and naphthylmethyl.

As used herein, the term "arylalkoxy" refers to any of the $C_{1-10}$ alkoxy groups substituted by any of the aryl groups as defined above. Examples of arylalkoxy groups include benzyloxy and phenethyloxy.

As used herein, the term "aryloxy" refers to oxygen substituted by any of the $C_{6-14}$ aryl groups defined above.

As used herein, the term "carboxamide" refers to a group —C(=O)—NH$_2$.

As used herein, the term "preventing an increase in a symptom" refers to both not allowing a symptom to increase or worsen, as well as reducing the rate of increase in the symptom. For example, a symptom can be measured as the amount of particular disease marker, i.e., a protein. In another example the symptom can be cognitive decline. Preventing an increase, according to the definition provided herein, means that the amount of symptom (e.g., protein or cognitive decline) does not increase or that the rate at which it increases is reduced.

As used herein, the term "treating a disease or disorder" refers to a slowing of or a reversal of the progress of the disease. Treating a disease or disorder includes treating a symptom and/or reducing the symptoms of the disease.

"Treatment of a disorder or disease" implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

"Treatment of a disorder or disease" may, for example, lead to a halt in the progression of the disorder or disease (e.g., no deterioration of symptoms) or a delay in the progression of the disorder or disease (in case the halt in progression is of a transient nature only). "Treatment of a disorder or disease" may also lead to a partial response (e.g., amelioration of symptoms) or complete response (e.g., disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above).

Treatment of a disorder or disease may, inter alia, comprise curative treatment (preferably leading to a complete response and eventually to healing of the disorder or disease) and palliative treatment (including symptomatic relief).

As used herein, the term "preventing a disease or disorder" refers to a slowing of the disease or of the onset of the disease or the symptoms thereof. Preventing a disease or disorder can include stopping the onset of the disease or symptoms thereof. As used herein, the term "unit dosage form" refers to a physically discrete unit, such as a capsule or tablet suitable as a unitary dosage for a human patient. Each unit contains a predetermined quantity of a compound of Formula (I), which was discovered or believed to produce the desired pharmacokinetic profile which yields the desired therapeutic effect. The dosage unit is composed of a compound of Formula (I) in association with at least one pharmaceutically acceptable carrier, salt, excipient, or combination thereof.

For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

As used herein, the term "dose" or "dosage" refers the amount of active ingredient that an individual takes or is administered at one time. For example, a 40 mg dose of a compound of Formula (I) refers to, in the case of a twice-daily dosage regimen, a situation where the individual takes 40 mg of a compound of Formula (I) twice a day, e.g., 40 mg in the morning and 40 mg in the evening. The 40 mg of a compound of Formula (I) dose can be divided into two or more dosage units, e.g., two 20 mg dosage units of a compound of Formula (I) in tablet form or two 20 mg dosage units of a compound of Formula (I) in capsule form.

As used herein, a "pharmaceutically acceptable prodrug" is a compound that may be converted under physiological conditions or by solvolysis to the specified compound or to a pharmaceutically acceptable salt of such compound.

The present invention also encompasses pharmaceutically acceptable prodrugs of the compounds described and defined herein, in particular prodrugs of the compounds of Formula (I) or (II). Prodrugs of the compounds of Formula (I) or (II) are derivatives which have chemically or metabolically cleavable groups and become, by solvolysis or under physiological conditions, the compounds of the present invention which are pharmaceutically active in vivo. Prodrugs of compounds of Formula (I) or (II) according to the present invention may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound employed in the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester, N,N-diethylglycolamidoester or α-acetoxyethylester. When a compound employed in the present invention has a hydroxy group, an acyloxy derivative prepared by reacting the hydroxyl group with a suitable acyl-halide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)—C$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$. When a compound employed in the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

As used herein, a "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

The present invention also embraces solid forms of the compounds of Formula (I) or (II) in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

Additionally, the compounds of Formula (I) or (II) can contain asymmetric carbon atoms and can therefore exist in racemic and optically active forms. Thus, optical isomers or enantiomers, racemates, tautomers, and diastereomers are also encompassed in the compounds of Formula (I) or (II). The methods of the present invention include the use of all such isomers and mixtures thereof. Methods of separation of enantiomeric and diastereomeric mixtures are well known to one skilled in the art. Furthermore, racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization. The present invention encompasses any isolated racemic or optically active form of compounds described in Formula (I) or (II), or any mixture thereof. In one aspect, the compounds of the invention have a trans configuration around the cyclopropyl ring as in trans-phenylcyclopropylamine. In one aspect, the compounds of the invention have a cis configuration around the cyclopropyl ring as in cis-phenylcyclopropylamine. In a preferred aspect, the compounds of Formula (I) or (II) have the trans configuration.

Typically, compounds according to Formula (I) can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 µg to about 2000 mg, preferably from about 5 µg to about 1000 mg.

It should be understood that the dosage ranges set forth above are exemplary only and are not intended to limit the scope of this invention. The therapeutically effective amount for each active compound can vary with factors including but not limited to the activity of the compound used, stability of the active compound in the subject's/patient's body, the severity of the conditions to be alleviated, the total weight of the subject/patient treated, the route of administration, the ease of absorption, distribution, and excretion of the active compound by the body, the age and sensitivity of the subject/patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included.

In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and anti-oxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly (glycolic-co-L-lactic acid) may be useful. See, e.g., Phillips et al. (1984) *J. Pharmaceut. Sci.*, 73: 1718-1720.

Accordingly, the compounds of Formula (I) or (II) or the pharmaceutical compositions comprising a compound of Formula (I) or (II) and a pharmaceutically acceptable carrier may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e. g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to patient, the active compound in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the subject/patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Thus, in one embodiment the compound of the present invention, in particular the compound of Formula (I) or (II), can be used in combination with other therapeutic agents. When the compound is used in combination with a second therapeutic agent active against the same disease, the dose of each compound may differ from that when the compound is used alone. The combination of a compound of this invention with (an) other drug(s) may comprise the administration of the drug(s) with the compound of the invention. Such an administration may comprise simultaneous/concomitant administration. However, sequential/separate administration is also envisaged.

Preferably, the second therapeutic agent to be administered in combination with the compound of the present invention is an anticancer drug. The anticancer drug to be administered in combination with the compound of the invention may be: a tumor angiogenesis inhibitor (for example, a protease inhibitor, an epidermal growth factor receptor kinase inhibitor, or a vascular endothelial growth factor receptor kinase inhibitor); a cytotoxic drug (for example, an antimetabolite, such as purine and pyrimidine analogue antimetabolites); an antimitotic agent (for example, a microtubule stabilizing drug or an antimitotic alkaloid); a platinum coordination complex; an anti-tumor antibiotic; an alkylating agent (for example, a nitrogen mustard or a nitrosourea); an endocrine agent (for example, an adrenocorticosteroid, an androgen, an anti-androgen, an estrogen, an anti-estrogen, an aromatase inhibitor, a gonadotropin-releasing hormone agonist, or a somatostatin analogue); or a compound that targets an enzyme or receptor that is overexpressed and/or otherwise involved in a specific metabolic pathway that is misregulated in the tumor cell (for example, ATP and GTP phosphodiesterase inhibitors, histone deacetylase inhibitors, protein kinase inhibitors (such as serine, threonine and tyrosine kinase inhibitors (for example, Abelson protein tyrosine kinase)) and the various growth factors, their receptors and kinase inhibitors therefor (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine; aminopeptidase inhibitors; proteasome inhibitors; cyclooxygenase inhibitors (for example, cyclooxygenase-1 or cyclooxygenase-2 inhibitors); or topoisomerase inhibitors (for example, topoisomerase I inhibitors or topoisomerase II inhibitors).

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazines (such as temozolomide).

A platinum coordination complex which can be used as an anticancer drug in combination with a compound of the present invention may be, for example, cisplatin, carboplatin, nedaplatin, oxaliplatin, satraplatin, or triplatin tetranitrate.

A cytotoxic drug which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with a compound of the present invention may be, for example, a taxane (such as docetaxel, larotaxel, ortataxel, paclitaxel/taxol, or tesetaxel), a Vinca alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/aza-epothilone B).

An anti-tumor antibiotic which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from Streptomyces (such as actinomycin (including actinomycin D), bleomycin, mitomycin (including mitomycin C), or plicamycin).

A tyrosine kinase inhibitor which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, or vandetanib.

A topoisomerase-inhibitor which can be used as an anticancer drug in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

Further anticancer drugs may be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, and vorinostat.

Also biological drugs, like antibodies, antibody fragments, antibody constructs (for example, single-chain constructs), and/or modified antibodies (like CDR-grafted antibodies, humanized antibodies, "full humanized" antibodies, etc.)

directed against cancer or tumor markers/factors/cytokines involved in proliferative diseases can be employed in co-therapy approaches with the compounds of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP-A-1 071 752) and anti-TNF antibodies (see, e.g., Taylor P C. Antibody therapy for rheumatoid arthritis. Curr Opin Pharmacol. 2003. 3(3):323-328). Further antibodies, antibody fragments, antibody constructs and/or modified antibodies to be used in co-therapy approaches with the compounds of the invention can be found in Taylor P C. Curr Opin Pharmacol. 2003. 3(3):323-328; Roxana A. Maedica. 2006. 1(1):63-65.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the present compound or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

In another embodiment, the compounds of the present invention, in particular the compounds of Formula (I) or (II), are administered in combination with physical therapy, such as radiotherapy. Radiotherapy may commence before, after, or simultaneously with administration of the compounds. For example, radiotherapy may commence 1 to 10 minutes, 1 to 10 hours or 24 to 72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens. Without being bound by theory, the compounds of the present invention may be used to render cells, in particular undesired proliferative/hyperproliferative cells like cancer or tumor cells, more susceptible to such a physical therapy, e.g. radiotherapy.

Accordingly, the present invention relates to a compound of Formula (I) or (II) or a pharmaceutically acceptable salt or solvate thereof, or a pharmaceutical composition comprising any of the aforementioned entities in combination with a pharmaceutically acceptable carrier, for use in the treatment or prevention of cancer, whereby the compound or the pharmaceutical composition is to be administered in combination with an anti-proliferative drug, an anticancer drug, a cytostatic drug, a cytotoxic drug and/or radiotherapy.

In the context of the present invention, the "subject" or "patient", such as the subject/patient in need of treatment or prevention, may be an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e. g. gorilla, chimpanzee, orangutang, gibbon), or a human. The meaning of the terms "animal", "mammal", etc. is well known in the art and can, for example, be deduced from. Wehner and Gehring (1995; Thieme Verlag). In the context of this invention, it is particularly envisaged that animals are to be treated which are economically, agronomically or scientifically important. Scientifically important organisms include, but are not limited to, mice, rats, and rabbits. Non-limiting examples of agronomically important animals are sheep, cattle and pig, while, for example, cats and dogs may be considered as economically important animals. Preferably, the subject/patient is a mammal. More preferably, the subject/patient is a human.

General Synthetic Route Description

Figure 2:
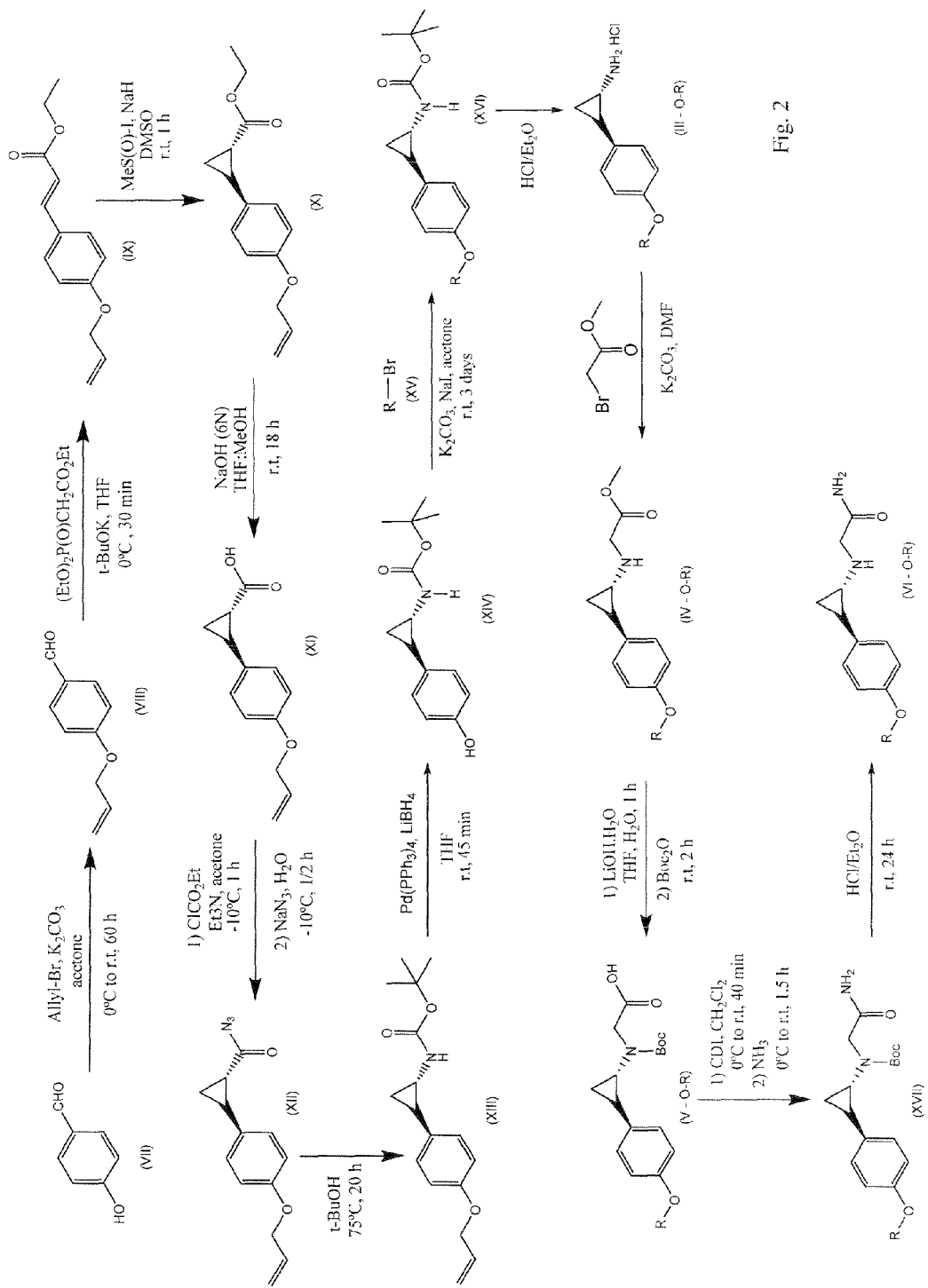
Figure 3:
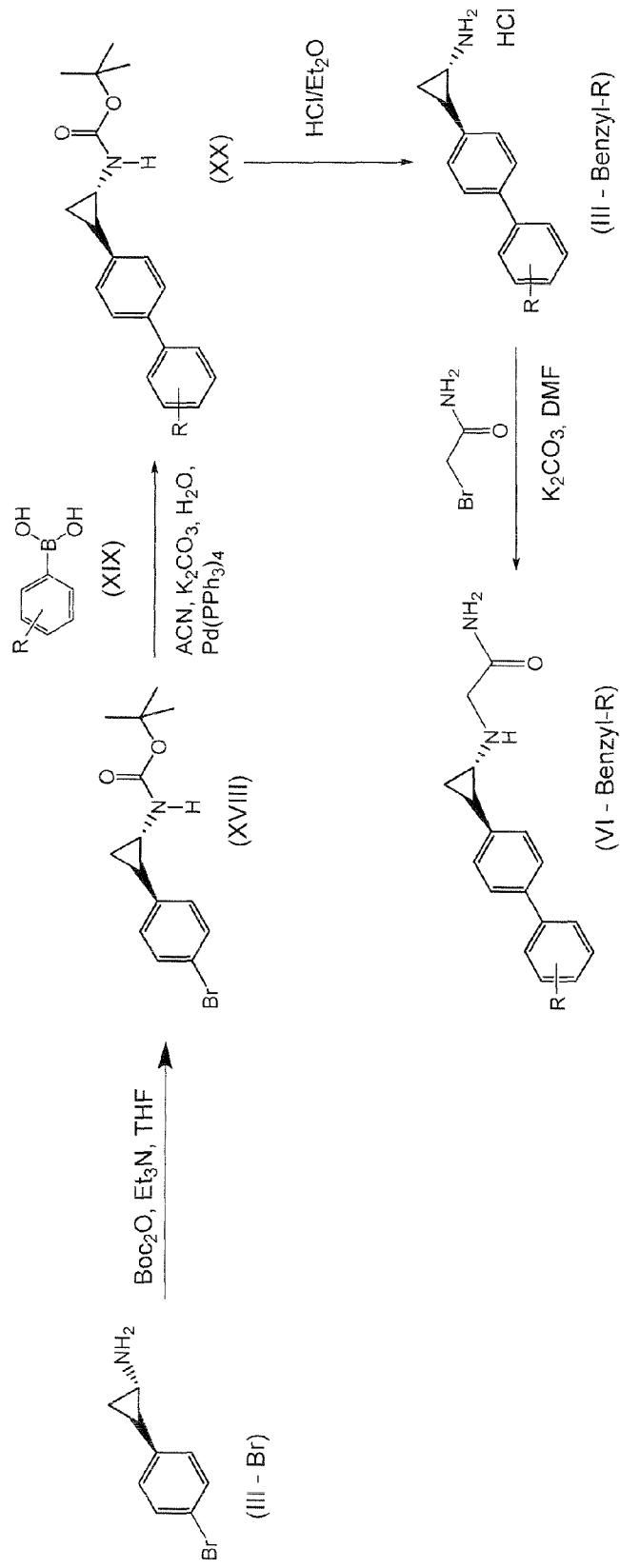
Figure 4:
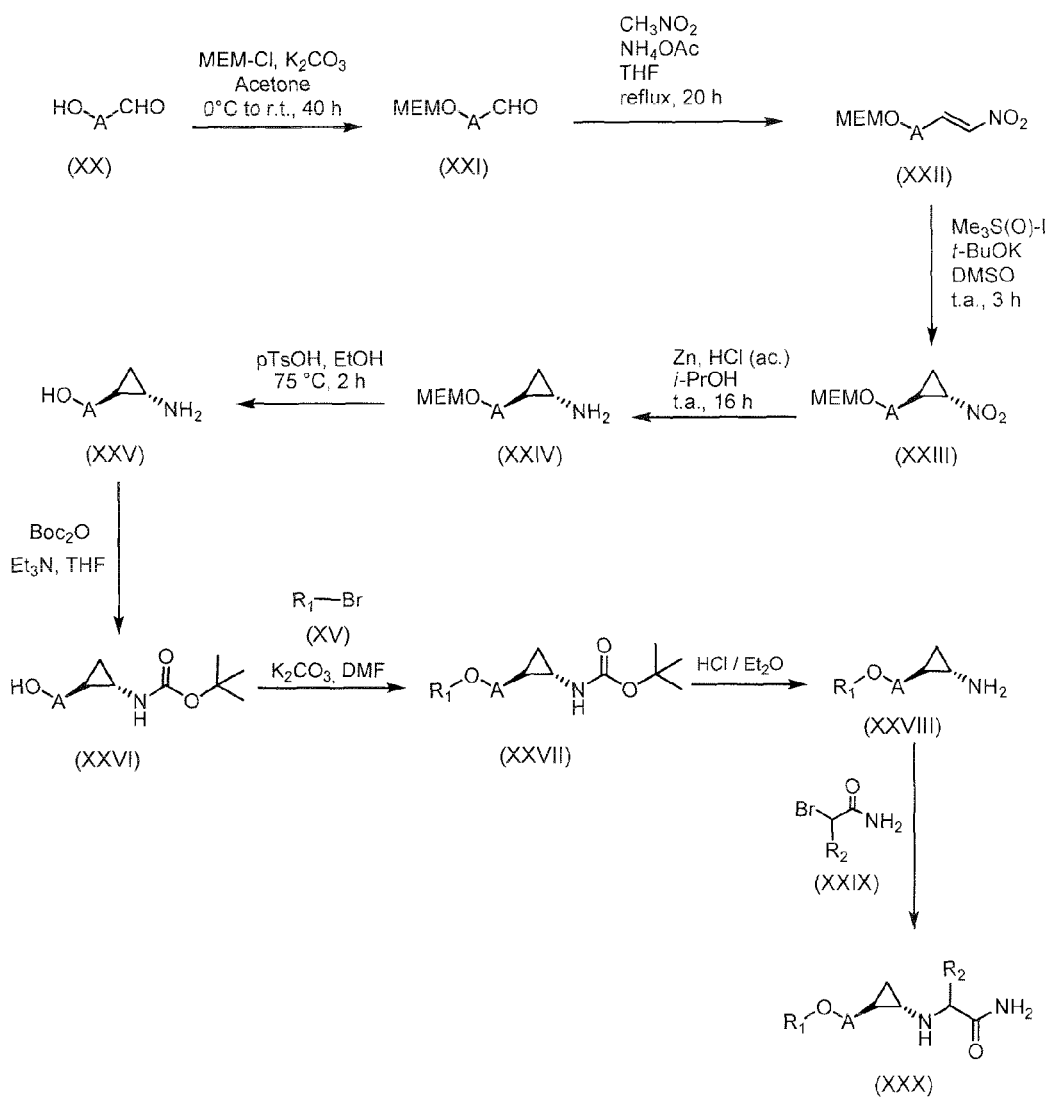
Figure 5:
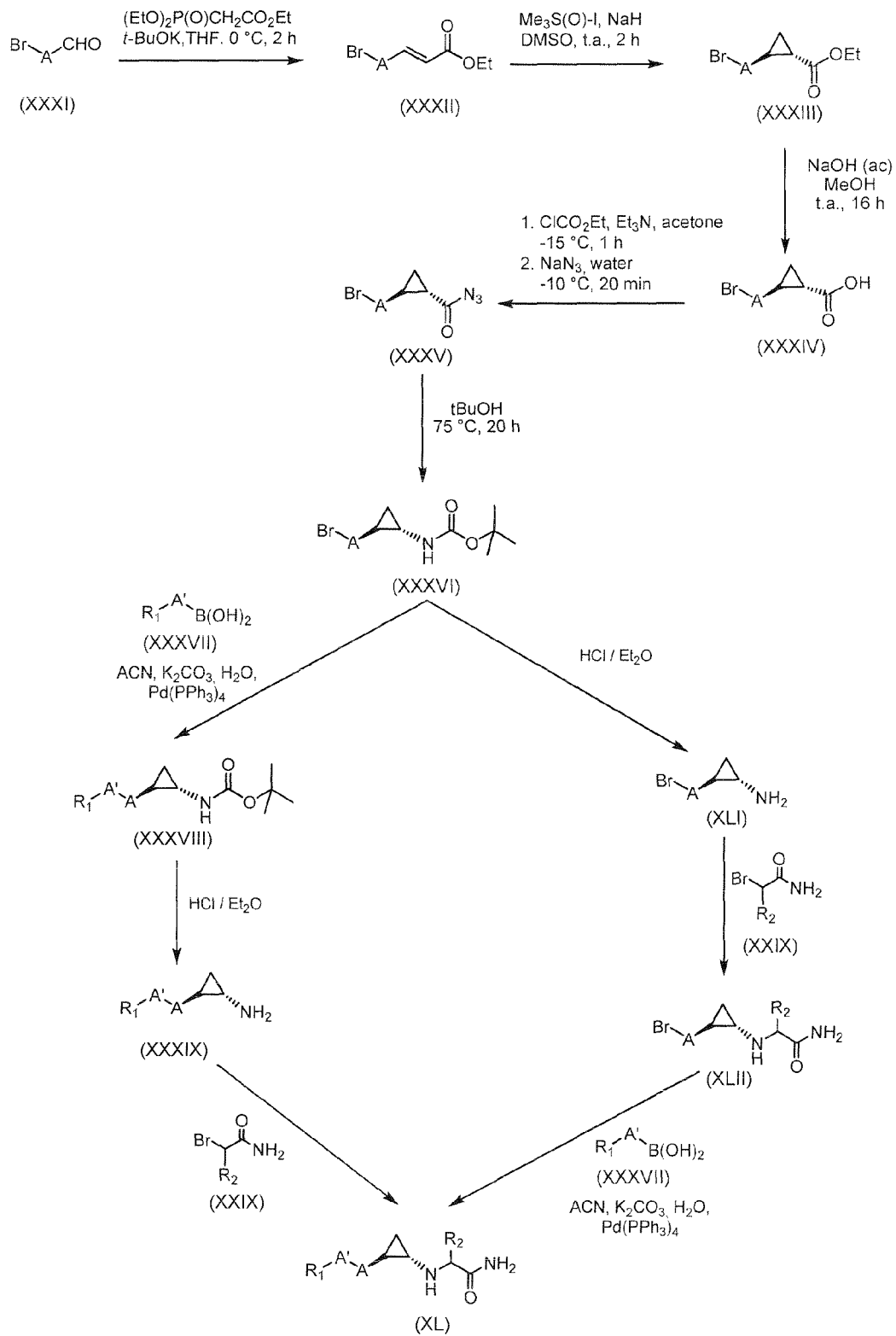

The compounds of the invention described above, in particular the compounds of Formula (I) and the compounds of Formula (II), can be synthesized by the general route described in the Scheme 1 (FIG. 1), Scheme 2 (FIG. 2), Scheme 3 (FIG. 3), Scheme 4 (FIG. 4) and Scheme 5 (FIG. 5).

DETAILED DESCRIPTION OF DRAWINGS

Scheme 1 (see FIG. 1) where CDI (N,N'-carbonyldiimidazole), DCM (dichloromethane), DIPEA (Diisopropylamine), DMSO (Dimethyl sulfoxide), THF (Tetrahydrofurane). Commercially available nitrostyrenes of formula (I) have been subjected to a cyclopropanation reaction using trimethylsulfoxonium iodide and potassium tertbutylate. The nitro group of the resulted nitrocyclopropyl derivatives of formula (II) (including trans ((1S,2R), (1R,2S)) version as well the individual diastereoisomers corresponding to (1S,2R) and (1R,2S) can be used) has been then reduced using zinc in hydrochloric acid to afford the cyclopropylamino derivatives of formula (III). Note that the nitrostyrenes of Formula (I) in the synthetic scheme are different than the compounds of Formula (I) of the invention (that is to say that the compounds of the invention of Formula (I) do not encompass the nitrosyrene starting material described in Scheme 1 as Formula (I**)). These compounds of formula (III) react with methyl 2-bromoacetate in acetonitrile using diisopropylamine as a base to get the methyl 2-((trans)-2-phenylcyclopropylamino) acetate derivatives of formula (IV). Hydrolysis of these compounds with LiOH.H$_2$O using THF-H$_2$O as a solvent and later reaction with t-Butyl Dicarbonate at room temperature leads to 2-(tert-butoxycarbonyl((trans)-2-phenylcyclopropyl)amino)acetic acid derivatives of formula (V). The reaction of the acid first with N,N'-carbonyldiimidazole in dichloromethane and later addition of ammonia leads to the corresponding amide that reacts with hydrochloric acid 2M in diethyl ether using diethyl ether as a solvent resulting in the formation of the corresponding hydrochloride salt of the 2-((trans)-2-phenylcyclopropylamino)acetamide derivatives of formula (VI), which are subject of the present invention as defined above.

Scheme 2 (FIG. 2) wherein CDI (N,N'-carbonyldiimidazole), DCM (dichloromethane), DIPEA (Diisopropylamine), DMF (N,N-Dimethylformamide), DMSO (Dimethyl sulfoxide), THF (Tetrahydrofuran).

The reaction of 4-hydroxybenzaldehyde of formula (VII) with allyl bromide in acetone, using K$_2$CO$_3$ as a base leads to the formation of 4-(allyloxy)benzaldehyde of formula (VIII). This product reacts with ethyl 2-(diethoxyphosphoryl)acetate and potassium tert-butoxide in tetrahydrofurane at 0° C. to get (E)-ethyl 3-(4-(allyloxy)phenyl)acrylate of formula (IX) which is subjected to cyclopropanation reaction using trimethylsulfoxonium iodide and sodium hydride in dimethyl sulfoxide as a solvent leading to (trans)-ethyl 2-(4-(allyloxy) phenyl)cyclopropanecarboxylate of formula (X) (being trans ((1S,2R), (1R,2S)) mixture although the individual diastereoisomers corresponding to (1S,2R) and (1R,2S) can be used).

Hydrolysis to the corresponding (trans)-2-(4-(allyloxy)phenyl)cyclopropanecarboxylic acid of formula (XI) was performed using NaOH 6N in THF-MeOH. The reaction, first with ethyl chloroformate and triethylamine in acetone and later with sodium azide in water leads to the formation of (trans)-2-(4-(allyloxy)phenyl)cyclopropanecarbonyl azide of formula (XII). Reaction with tert-butanol results in the formation of tert-butyl(trans)-2-(4-(allyloxy)phenyl)cyclopropylcarbamate of formula (XIII). Deprotection of the allyl group with tetrakis(triphenylphospine)palladium(0) and lithium borohydride in tetrahydrofuran leads to tert-butyl (trans)-2-(4-hydroxyphenyl)cyclopropylcarbamate of formula (XIV). Alkylation with commercially available alkyl bromides of formula (XV) using sodium iodide, potassium carbonate as a base and N,N-dimethylformamide as a solvent, results in the formation of the corresponding ether derivatives of formula (XVI). Deprotection of the Boc-group using HCl 2M in diethyl ether using diethyl ether as a solvent leads to the formation of the corresponding hydrochloride salts of the derivatives of formula (III) (—O—R). Alkylation with commercially available methyl 2-bromoacetate using potassium carbonate as a base and N,N-dimethylformamide as a solvent results in the formation of the methyl acetate derivatives of formula (IV) (—O—R). First step of hydrolysis to the corresponding acid derivative was performed using LiOH monohydrated in THF-H$_2$O and later reaction with t-Butyl Dicarbonate at room temperature leads to the Boc-protected derivatives of formula (V) (—O—R). Reaction of the acid with N,N'-carbonyldiimidazole in dichloromethane and later addition of ammonia results in the formation of the amide derivatives of formula (XVII). Final Boc-deprotection using HCl 2M in diethyl ether using diethyl ether as a solvent leads to the formation of the corresponding hydrochloride salt of the amide derivatives of formula (VI) (—O—R), which are also subjects of the present invention.

Scheme 3 (FIG. 3) where ACN (acetonitrile), DMF (N,N-Dimethylformamide), THF (tetrahydrofuran).

The reaction of intermediate B, (trans)-2-(4-bromophenyl)cyclopropanamine, of formula (III-Br) (including trans ((1S,2R), (1R,2S)) version as well the individual diastereoisomers corresponding to (1S,2R) and (1R,2S) can be used) with t-Butyl dicarbonate at room temperature using triethylamine as a base and tetrahydrofurane as a solvent leads to tert-butyl (trans)-2-(4-bromophenyl)cyclopropylcarbamate of formula (XVIII). Reaction with commercially available boronic acid derivatives of formula (XIX) using acetonitrile and water as a solvent, potassium carbonate as a base and Tetrakis(triphenylphospine)Paladium (0) as a catalyst leads to the formation of tert-butyl(trans)-2-(biphenyl-4-yl)cyclopropylcarbamate derivatives of formula (XX). Deprotection of the Boc-group using HCl 2M in diethyl ether using diethyl ether as a solvent leads to the formation of the corresponding hydrochloride salt of the (trans)-2-(biphenyl-4-yl)cyclopropanamine derivatives of formula (III) (-Benzyl-R). Alkylation of these compounds with commercially available 2-bromoacetamide using potassium carbonate as a base and N,N-dimethylformamide as a solvent results in the formation of the 2-((trans)-2-(biphenyl-4-yl)cyclopropylamino)acetamide derivatives of formula (VI) (-Benzyl-R), which are also subjects of the present invention.

Scheme 4 (FIG. 4) where DMF (N,N-Dimethylformamide), DMSO (Dimethyl sulfoxide), MEM-Cl (methoxyethoxymethyl chloride), p-TsOH (p-Toluenesulfonic acid), THF (Tetrahydrofuran).

The reaction of commercially available aldehydes of formula (XX) with methoxyethoxymethyl chloride in acetone using potassium carbonate as a base leads to the formation of aldehyde derivatives of formula (XXI). This product reacts with nitromethane and ammonium acetate in tetrahydrofuran to give the nitrovinyl derivative of formula (XXII). Cyclopropanation reaction using trimethylsulfoxonium iodide and sodium hydride in dimethyl sulfoxide as a solvent leads to the formation of (trans)-nitrocyclopropane derivatives of formula (XXIII) (being trans ((1S,2R), (1R,2S)) mixture although the individual diastereoisomers corresponding to (1S,2R) and (1R,2S) can be used). The nitro group has been then reduced using zinc in hydrochloric acid to afford the (trans)-cyclopropylamino derivatives of formula (XXIV). Deprotection using p-toluenesulfonic acid in ethanol leads to the formation of derivatives of formula (XXV). Reaction with t-butyl dicarbonate in tetrahydrofuran using triethylamine as a base leads to tert-butyl(trans)-cyclopropylcarbamate derivatives of formula (XXVI). Alkylation with commercially available alkyl bromide derivatives of formula (XV) using potassium carbonate as a base and N,N-dimethylformamide as a solvent results in the formation of derivatives of formula (XXVII). Boc-deprotection using HCl 2M in diethyl ether using diethyl ether as a solvent leads to the formation of the (trans)-cyclopropylamino derivatives of formula (XVIII). Alkylation of these compounds with 2-bromoacetamide derivatives of formula (XXIX) results in the formation of derivatives of formula (XXX), which are also subjects of the present invention. The skilled artisan recognizes that other bromoacetamide (bromoalkylamides) derivatives, analogs, or homologs can be used in place of those of Formula (XXIX) in the corresponding alkylation reaction to give compounds of the invention having different (L) groups. For example bromopropaneamide (e.g., BrCH$_2$CH$_2$C(=O)NH$_2$) can be used to give compounds of the invention having —CH$_2$CH$_2$— linker attached to the —C(=O)NH$_2$ moiety, or bromobutylamide (e.g., BrCH$_2$CH$_2$CH$_2$C(=O)NH$_2$) or other amides (e.g., BrCH$_2$CH$_2$CH(CH$_3$)C(=O)NH$_2$, BrCH$_2$CH$_2$C(CH$_3$)$_2$C(=O)NH$_2$, BrCH(CH$_3$)C(=O)NH$_2$, and BrC(CH$_3$)$_2$C(=O)NH$_2$)). Such bromoalkylamides can be synthesized by a person of ordinary skill in the art of organic synthesis using standard procedures.

Scheme 5 (FIG. 5) where ACN (acetonitrile), DMSO (Dimethyl sulfoxide), THF (Tetrahydrofuran).

Commercially available aldehydes of formula (XXXI) have been subjected to a Horner-Wadsworth-Emmons reaction using triethyl phosphono acetate and potassium tert-butoxide in tetrahydrofuran at 0° C. to get the ethyl acrylate derivative of formula (XXXII) which is subjected to a cyclopropanation reaction using trimethylsulfoxonium iodide and sodium hydride in dimethyl sulfoxide as a solvent leading to (trans)-ethyl cyclopropanecarboxylate derivatives of formula (XXXIII) (being trans ((1S,2R), (1R,2S)) mixture although the individual diastereoisomers corresponding to (1S,2R) and (1R,2S) can be used). Hydrolysis to the corresponding (trans)-cyclopropanecarboxylic acid derivatives of formula (XXXIV) was performed using NaOH in MeOH. The reaction, first with ethyl chloroformate and triethylamine in acetone and later with sodium azide in water leads to the formation of (trans)-cyclopropanecarbonyl azide derivatives of formula (XXXV). Reaction with tert-butanol results in the formation of tert-butyl (trans)-cyclopropylcarbamate derivatives of formula (XXXVI).

Reaction with commercially available boronic acid derivatives of formula (XXXVII) using acetonitrile and water as a solvent, potassium carbonate as a base and Tetrakis(triphenylphospine)Paladium (0) as a catalyst leads to the formation of tert-butyl(trans)-cyclopropylcarbamate derivatives of formula (XXXVIII). Deprotection of the Boc-group using HCl 2M in diethyl ether using diethyl ether as a solvent leads to the formation of the (trans)-cyclopropanamine derivatives of formula (XXXIX). Alkylation of these compounds with 2-bromoacetamide derivatives of formula (XXIX) (e.g., R2 is a $C_1$ to $C_6$ alkyl) results in the formation of derivatives of formula (XL), which are also subjects of the present invention. The skilled artisan recognizes that other bromoacetamide (bromoalkylamides) derivatives, analogs, or homologs can be used in place of those of Formula (XXIX) in the corresponding alkylation reaction to give compounds of the invention having different (L) groups. For example bromopropaneamide (e.g., $BrCH_2CH_2C(=O)NH_2$) can be used to give compounds of the invention having —$CH_2CH_2$— linker attached to the —$C(=O)NH_2$ moiety, or bromobutylamide (e.g., $BrCH_2CH_2CH_2C(=O)NH_2$) or other amides (e.g., $BrCH_2CH_2CH(CH_3)C(=O)NH_2$, $BrCH_2CH_2C(CH_3)_2C(=O)NH_2$, $BrCH(CH_3)C(=O)NH_2$, and $BrC(CH_3)_2C(=O)NH_2$). Such bromoalkylamides can be synthesized by a person of ordinary skill in the art of organic synthesis using standard procedures.

Alternatively, deprotection of the Boc-group using HCl 2M in diethyl ether using diethyl ether as a solvent leads to the formation of the (trans)-cyclopropanamine derivatives of formula (XLI). Alkylation of these compounds with 2-bromoacetamide derivatives of formula (XXIX) results in the formation of derivatives of formula (XLII). The reaction with commercially available boronic acid derivatives of formula (XXXVII) using acetonitrile and water as a solvent, potassium carbonate as a base and Tetrakis(triphenylphospine) Paladium (0) as a catalyst also leads to the formation of derivatives of formula (XL), which are also subjects of the present invention.

EXAMPLES

The program used to generate the names corresponding to the structures in the Example compounds below was MDL ISIS Draw 2.5 (using the ACD/Name for ISIS Draw add-in) or Chemdraw (ChemBioDraw Ultra version 11.0.1 by CambridgeSoft). This program named the molecules as the (1S, 2R) configuration due to the configuration of the input structure and the "trans" term has been substituted in the place of the (1S,2R) term specified by the program. The structures depicted below for the Example compounds below are shown as having one particular stereochemical configuration around the cyclopropyl carbon atoms of the phenylcyclopropylamine core (1S,2R). All the compounds synthesized in the Examples are mixtures having both configurations (1R,2S) and (1S,2R), that is to say they are "trans" in respect to the cyproyl ring of the cyclopropyl ring system. This is due to the fact the phenylcyclopropylamine starting material used is "trans". It is contemplated that the cis configuration starting material or the individual diastereomers could be used as starting material, all of which are either commercially or synthetically available. Thus, the invention relates to compounds of Formula (I) and those of the examples that have specific stereochemical configurations around the cyclopropyl ring e.g., trans ((1R,2S) and (1S,2R)) and cis (1R,2R) and (1S,2S). A preferred stereochemical configuration around the cyclopropyl ring of phenylcyclopropylamine is trans.

The compounds of the examples can also be synthesized or provided in a salt form. The skilled artisan is aware and capable of making salt forms and/or converting salt forms of the compounds of the invention, e.g., compounds of Formula (I) and those of the Examples. In some cases the compounds of Formula (I) and the Examples can be more stable as salt forms as compared to free base.

In reference to the synthetic schemes described herein the following intermediates (and analogous intermediates or derivatives thereof) can be made using the following procedures.

Intermediate A 1-bromo-4-[(trans)-2-nitrocyclopropyl]benzene

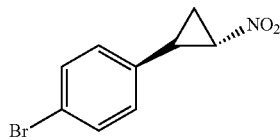

Trimethylsulfoxonium iodide (0.62 g, 2.82 mmol) was added in portions to a solution of t-BuOK (0.32 g, 2.82 mmol) in dry DMSO (5 mL). After 10 min a solution of 1-bromo-4-[(trans)-2-nitrovinyl]benzene (0.53 g, 2.35 mmol) in DMSO (5 mL) was transferred via canula and the mixture was stirred at room temperature for 6 h. The reaction was poured over water (10 mL) and extracted with $Et_2O$ (3×10 mL); the organic layers were washed with brine (2×15 mL), dried over anhydrous $Na_2SO_4$ and filtered. After removal of the solvent, the residual oil was purified by column chromatography on silica gel (5% EtOAc/hexanes) affording 0.15 of 1-bromo-4-[(trans)-2-nitrocyclopropyl]benzene [27% yield].

Intermediate B (trans)-2-(4-bromophenyl)cyclopropanamine

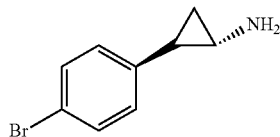

Zn dust (1.97 g, 30 mol) was added in small portions, over a period of 30 min, to a vigorously stirred solution of 1-bromo-4-[(trans)-2-nitrocyclopropyl]benzene (Intermediate A, 0.73 g, 3.0 mmol) in i-PrOH (25 mL) and HCl (11 mL of aqueous solution 2.7 N, 30 mmol). After 17 h the mixture was filtered through a pad of celite, that was washed with 10 mL of methanol. The filtrate was concentrated and 10 mL of water were added, washing with $CH_2Cl_2$ (3×15 mL). The organic layers were dried over anhydrous $Na_2SO_4$ and filtered. After removal of the solvent, the crude product was purified by column chromatography on silica gel (10% MeOH/$CH_2Cl_2$) affording 0.06 g of (trans)-2-(4-bromophenyl)cyclopropanamine [white solid. 10% yield].

1HNMR (CD3OD): 1.45 (m, 2H), 2.61 (m, 1H), 2.86 (m, 1H), 6.98 (d, 2H), 7.11 (d, 2H). MS (M+H): 211.9

Intermediate C

Tert-butyl(trans)-2-(4-bromophenyl)cyclopropylcarbamate

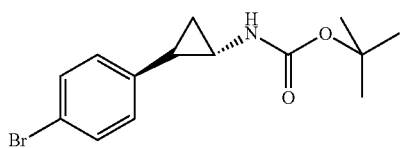

Boc$_2$O (1.65 equiv) was added to a solution of (trans)-2-(4-bromophenyl)cyclopropanamine (Intermediate B; 1 equiv.) and Et$_3$N (1.65 equiv) in THF and stirred for 3 h. After removal of the solvent, the crude residue was dissolved in EtOAc and consecutively washed with water and HCl (10% aqueous solution) and brine. The organic layer was dried over anhydrous Na$_2$SO$_4$ and filtered; after removal of the solvent, the residue was purified by column chromatography on silica gel (10-20% EtOAc/Hexanes), affording tert-butyl (trans)-2-(4-bromophenyl)cyclopropylcarbamate (Yield 85%)

Intermediate D 4-(allyloxy)benzaldehyde

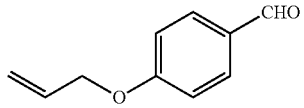

A solution of allyl bromide (5.94 mL, 68.78 mmol) in acetone (20 mL) was added, over a period of 20 min, to a mixture of 4-hydroxybenzaldehyde (8.00 g, 65.50 mmol) and K$_2$CO$_3$ (9.96 g, 72.06 mmol) in acetone (100 mL) cooled at 0° C. The mixture was allowed to reach room temperature and stirred for 60 h. After removal of the solvent, the crude residue was dissolved in EtOAc (100 mL) and washed twice with a mixture of water (100 mL) and NaOH (10% aqueous solution, 10 mL). The organic layer was dried over anhydrous Na$_2$SO$_4$ and filtered. After removal of the solvent, 10.00 g of 4-(allyloxy)benzaldehyde were obtained [Rf=0.5 (10% EtOAc/Hexanes), pale brown oil, 94% yield]

Intermediate E (E)-ethyl 3-(4-(allyloxy)phenyl)acrylate

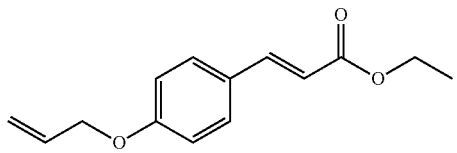 [SMILES: C=CCOc1ccc(/C=C/C(=O)OCC)cc1]

t-BuOK (4.57 g, 40.7 mmol) was added in small portions to a solution of triethyl phosphonoacetate (8.10 mL, 40.7 mmol) and 4-(allyloxy)benzaldehyde (Intermediate D, 6.00 g, 37.0 mmol) in THF (100 mL) cooled at 0° C., leading to the formation of a viscous mixture. After 30 min, water (20 mL) was added and the solvent was removed by rotatory evaporation. The crude residue was dissolved in EtOAc (100 mL) and washed with water (2×100 mL); the organic layer was dried over anhydrous Na$_2$SO$_4$ and filtered. After removal of the solvent, the residue was purified by column chromatography on silica gel (7% EtOAc/Hexanes), affording 7.76 g of (E)-ethyl 3-(4-(allyloxy)phenyl)acrylate [Rf=0.4 (10% EtOAc/Hexanes), colorless oil, 90% yield].

Intermediate F (trans)-ethyl 2-(4-(allyloxy)phenyl)cyclopropanecarboxylate

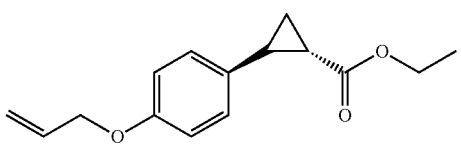

Trimethylsulfoxonium iodide (3.98 g, 18.08 mmol) was added in small portions to a suspension of NaH [0.72 g (60% in mineral oil), 18.08 mmol] in dry DMSO (20 mL). The mixture was stirred until gas evolution ceased and a clear solution was formed (1.5 h). Then, a solution of ethyl(E)-ethyl 3-(4-(allyloxy)phenyl)acrylate (Intermediate E, 4.00 g, 17.22 mmol) in DMSO (10 mL) was trasferred via cannula and the reaction was stirred for additional 1 h. The mixture was poured into brine (150 mL) and extrated with Et$_2$O (100 mL); the organic layer was washed with brine (150 mL), dried over anhydrous Na$_2$SO$_4$ and filtered. Removal of the solvent afforded a yellowish solid, that was purified by column chromatography on silica gel (10% EtOAc/Hexanes), affording 1.96 g of (trans)-ethyl 2-(4-(allyloxy)phenyl)cyclopropanecarboxylate [Rf=0.4 (10% EtOAc/Hexanes), white solid, 46% yield].

Intermediate G (trans)-2-[4-(allyloxy)phenyl]cyclopropanecarboxylic acid

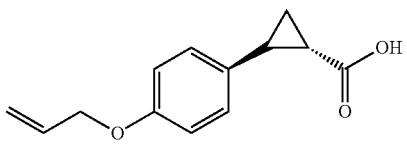

NaOH (6 N aqueous solution, 10 mL) was added to a solution of (trans)-ethyl 2-(4-(allyloxy)phenyl)cyclopropanecarboxylate (Intermediate F, 11.15 g, 45.27 mmol) in methanol (30 mL) and THF (25 mL) and stirred at room temperature for 18 h. After removal of the solvent, the residue was dissolved in CH$_2$Cl$_2$ (200 mL), acidified with HCl (10% aqueous solution, 30 mL), and washed with brine (2×200 mL). The organic layer was dried over anhydrous Na$_2$SO$_4$ and filtered. Removal of the solvent afforded 9.13 of (trans)-2-[4-(allyloxy)phenyl]cyclopropanecarboxylic acid [Rf=0.25 (5% MeOH/CH₂Cl₂), white solid, 92% yield]

Intermediate H (trans)-2-[4-(allyloxy)phenyl]cyclopropanecarbonyl azide

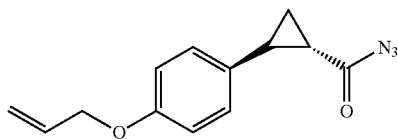

Ethyl chloroformate (2.72 mL, 28.52 mmol) was added to a solution of Et₃N (4.24 mL, 30.42 mmol) and (trans)-2-[4-(allyloxy)phenyl]cyclopropanecarboxylic acid (Intermediate G, 4.15 g, 19.01 mmol) in dry acetone (50 mL) cooled at −10° C., forming a white solid. After 1 h, a solution of NaN₃ (2.23 g, 34.23 mmol) in water (10 mL) was added to the reaction and stirred for additional 30 min. The solvent was removed by rotatory evaporation and the residue was dissolved in CH₂Cl₂ (20 mL); the organic layer was consecutively washed with a mixture of water (200 mL) and HCl (10% aqueous solution, 10 mL) and a mixture of water (200 mL) and NaOH (10% aqueous solution, 10 mL). The organic layer was dried over anhydrous Na₂SO₄ and filtered. After removal of the solvent, the residue was purified by column chromatography on silica gel (10% EtOAc/Hexanes), affording 4.10 g of (trans)-2-[4-(allyloxy)phenyl]cyclopropanecarbonyl azide [Rf=0.75 (20% EtOAc/Hexanes), white solid, 89% yield].

¹H-NMR (CDCl₃, 250 MHz, δ): 7.05-6.96 (m, 2H, ArH); 6.87-6.78 (m, 2H, ArH); 6.12-5.95 (m, 1H, CH); 5.44-5.22 (m, 2H, CH2); 4.54-4.46 (m, 2H, CH2); 2.65-2.53 (m, 1H, CH); 1.88-1.76 (m, 1H, CH); 1.73-1.63 (m, 1H, CH2);1.47-1.36 (m, 1H, CH2).

Intermediate I tert-butyl(trans)-2-[4-(allyloxy)phenyl]cyclopropylcarbamate

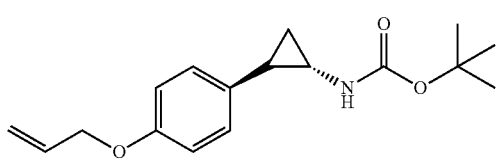

A solution of (trans)-2-[4-(allyloxy)phenyl]cyclopropanecarbonyl azide (Intermediate H, 1.80 g, 7.40 mmol) in t-BuOH (20 mL) was heated at 75° C. for 20 h. After removal of the solvent, the residue was purified by column chromatography on silica gel (5%-15% EtOAc/Hexanes), affording 1.60 g of tert-butyl(trans)-2-[4-(allyloxy)phenyl]cyclopropylcarbamate [Rf=0.5 (20% EtOAc/Hexanes), white solid, 75% yield].

¹H-NMR (CDCl₃, 250 MHz, δ): 7.11-7.02 (m, 2H, ArH); 6.86-6.78 (m, 2H, ArH); 6.14-5.95 (m, 1H, CH); 5.46-5.33 (m, 1H, CH2); 5.32-5.23 (m, 1H, CH2); 4.86 (br s, 1H, NHBoc); 4.54-4.46 (m, 2H, CH2); 2.65 (br s, 1H, CH); 2.04-1.93 (m, 1H, CH); 1.45 (s, 9H, 3×CH3); 1.13-1.03 (m, 2H, CH2).

Intermediate J tert-butyl(trans)-2-(4-hydroxyphenyl)cyclopropylcarbamate

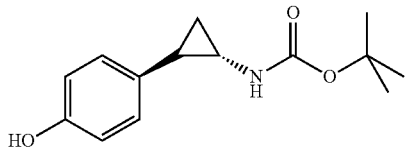

LiBH4 (0.34 g, 15.54 mmol) was added to a solution of Pd(PPh₃)₄ (0.15 g, 0.13 mmol) and tert-butyl(trans)-2-[4-(allyloxy)phenyl]cyclopropylcarbamate (Intermediate I, 0.75 g, 2.59 mmol) in dry THF (20 mL) and stirred at room temperature for 1 h. After removal of the solvent, the residue was dissolved in EtOAc (25 mL), acidified with HCl (10% aqueous solution, 2 mL), and washed with water (25 mL) and brine (25 mL). The organic layer was dried over anhydrous Na₂SO₄ and filtered. After removal of the solvent, the residue was purified by column chromatography on silica gel (10%-20% EtOAc/Hexanes), affording 0.58 g of tert-butyl(trans)-2-(4-hydroxyphenyl)cyclopropylcarbamate [Rf=0.3 (30% EtOAc/Hexanes), pale yellow foam, 90% yield].

¹H-NMR (CDCl₃, 250 MHz, δ): 6.93 (d, J=8.0 Hz, 2H, ArH); 6.69 (d, J=8.0 Hz, 2H, ArH); 6.46 (br s, 1H, OH); 4.90 (br s, 1H, NHBoc); 2.66 (br s, 1H, CH); 1.99-1.94 (m, 1H, CH); 1.46 (s, 9H, 3×CH3); 1.10-1.02 (m, 2H, CH2).

Example 1

2-((trans)-2-(4-(4-cyanobenzyloxy)phenyl)cyclopropylamino)acetamide hydrochloride

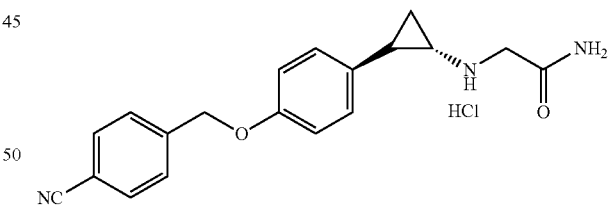

Step 1:
4-(bromomethyl)benzonitrile (0.47 g, 2.40 mmol) was added to a mixture of Intermediate J, tert-butyl(trans)-2-(4-hydroxyphenyl)cyclopropylcarbamate, (0.50 g, 2.00 mmol), K₂CO₃ (0.42 g, 3.00 mmol) and NaI (0.03 g, 0.20 mmol) in acetone (15 mL) and stirred at room temperature for 3 d. After removal of the solvent, the crude residue was dissolved in EtOAc (30 mL) and washed with brine (2×25 mL). The organic layer was dried over anhydrous Na₂SO₄ and filtered. After removal of the solvent, the residue was purified by column chromatography on silica gel (5%-50% EtOAc/Hexanes), affording 0.52 g of tert-butyl(trans)-2-{4-[(4-cyanobenzyl)oxy]phenyl}cyclopropylcarbamate [Rf=0.2 (30% EtOAc/Hexanes), pale yellow solid, 71% yield].

Step 2:

tert-butyl(trans)-2-{4-[(4-cyanobenzyl)oxy]phenyl}cyclopropylcarbamate (0.31 g, 0.85 mmol) was dissolved in a mixture of 1,4-dioxane/$H_2SO_4$ (15 mL, 10:1, v/v) and stirred at room temperature for 45 min. The reaction mixture was poured into water (15 mL), basified by addition of 15 mL of aqueous NaOH (10%) and extracted with EtOAc (2×15 mL); the organic layers were washed with brine (20 mL), dried over anhydrous $Na_2SO_4$ and filtered. After removal of the solvent, the crude residue was purified by column chromatography on silica gel (0%-3% MeOH/$CH_2Cl_2$) to afford 0.19 g of 4-({4-[(trans)-2-aminocyclopropyl]phenoxy}methyl)benzonitrile [Rf=0.2 (5% MeOH/$CH_2Cl_2$), beige solid, 85% yield].

$^1$H-NMR (CD$_3$OD, 250 MHz, δ): 7.73 (d, J=8.3 Hz, 2H, ArH); 7.61 (d, J=8.3 Hz, 2H, ArH); 6.97 (d, J=8.6 Hz, 2H, ArH); 6.87 (d, J=8.6 Hz, 2H, ArH); 5.14 (s, 2H, CH2); 2.42-2.33 (m, 1H, CH); 1.86-1.75 (m, 1H, CH); 0.97-0.83 (m, 2H, CH2).

Step 3:

A solution of methyl bromoacetate (0.08 mL, 0.91 mmol) in $CH_3CN$ (6 mL) was added, over a period of 15 min, to a solution of 4-({4-[(trans)-2-aminocyclopropyl]phenoxy}methyl)benzonitrile (0.22 g, 0.82 mmol) and DIPEA (0.28 mL, 1.64 mmol) in $CH_3CN$ (8 mL) at −10° C. The reaction was allowed to reach room temperature and stirred for 22 h. After removal of the solvent, the crude residue was purified by column chromatography on silica gel (2-5% MeOH/$CH_2Cl_2$) affording 0.12 g of methyl[((trans)-2-{4-[(4-cyanobenzyl)oxy]phenyl}cyclopropyl)amino]acetate [Rf=0.5 (5% MeOH/$CH_2Cl_2$), pale yellow oil, 44% yield].

Step 4:

A solution of LiOH.$H_2O$ (19 mg, 0.44 mmol) in water (2 mL) was added to a solution of methyl[((trans)-2-{4-[(4-cyanobenzyl)oxy]phenyl}cyclopropyl)amino]acetate (123 mg, 0.37 mmol) in THF (5 mL) and stirred at room temperature until completion of the reaction (TLC monitoring, 1 h). Di-tert-butyl dicarbonate (113 mg, 0.52 mmol) was added and the reaction mixture was stirred for additional 2 h. After removal of the solvent, the residue was dissolved in EtOAc (20 mL) and washed with brine (20 mL) and HCl (10% aqueous solution, 5 mL). The organic layer was dried over anhydrous $Na_2SO_4$ and filtered. After removal of the solvent, the crude product was purified by column chromatography on silica gel (5% MeOH/$CH_2Cl_2$) affording 100 mg of [(tert-butoxycarbonyl){(trans)-2-{4-[(4-cyanobenzyl)oxy]phenyl}cyclopropyl}amino]acetic acid [Rf=0.3 (5% MeOH/$CH_2Cl_2$), orange oil, 64% yield].

Step 5:

N,N'-Carbonyldiimidazole (27 mg, 0.17 mmol) was added to a solution of [(tert-butoxycarbonyl){(trans)-2-{4-[(4-cyanobenzyl)oxy]phenyl}cyclopropyl}amino]acetic acid (50 mg, 0.12 mmol) in dry $CH_2Cl_2$ (3 mL) at 0° C. (ice-water bath). The solution was stirred for 40 min at room temperature and cooled again at 0° C.; NH$_3$ (25% aqueous solution, 0.05 mL, 0.60 mmol) was added and the reaction was allowed to reach room temperature and stirred for additional 1.5 h. The mixture was diluted with $CH_2Cl_2$ (20 mL) and washed with brine (10 mL) and HCl (10% aqueous solution, 1 mL). The organic layer was dried over anhydrous $Na_2SO_4$ and filtered. After removal of the solvent, the crude product was purified by column chromatography on silica gel (5% MeOH/$CH_2Cl_2$) affording 38 mg of tert-butyl 2-amino-2-oxoethyl[(trans)-2-{4-[(4-cyanobenzyl)oxy]phenyl}cyclopropyl]carbamate [Rf=0.6 (10% MeOH/$CH_2Cl_2$), colorless oil, 76% yield].

Step 6:

HCl (2 M ethereal solution, 1 mL, 2 mmol) was added to a flask containing tert-butyl 2-amino-2-oxoethyl[(trans)-2-{4-[(4-cyanobenzyl)oxy]phenyl}cyclopropyl]carbamate (36 mg, 0.09 mmol) and the mixture was stirred at room temperature for 24 h. After removal of the solvent, the solid was washed with $Et_2O$ (2×2 mL) and vacuum dried, rendering 29 mg of 2-[((trans)-2-{4-[(4-cyanobenzyl)oxy]phenyl}cyclopropyl)amino]acetamide hydrochloride salt (white solid, 100% yield).

1H-NMR (CD3OD) δ (ppm): 1.31 (q, 1H), 1.44 (m, 1H), 2.47 (m, 1H), 2.89 (m, 1H), 3.98 (s, 2H), 5.18 (s, 2H), 6.96 (d, 2H), 7.13 (d, 2H), 7.62 (d, 2H), 7.76 (d, 2H). MS (M+H): 322.5

The following compounds can be synthesized following the method described for Example 1 using the corresponding commercially available alkyl bromides.

Example 2

2-((trans)-2-(4-(3-cyanobenzyloxy)phenyl)cyclopropylamino)acetamide hydrochloride

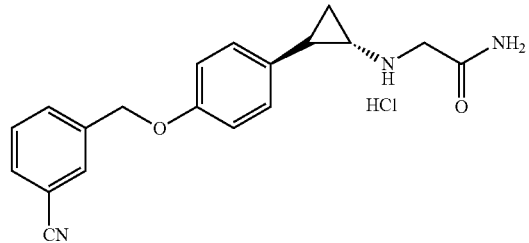

1HNMR (CD3OD) δ (ppm): 1.32 (q, 1H), 1.44 (m, 1H), 2.46 (m, 1H), 2.88 (m, 1H), 3.96 (s, 2H), 5.15 (s, 2H), 6.96 (d, 2H), 7.12 (d, 2H), 7.58 (d, 1H), 7.68 (d, 1H), 7.74 (d, 1H), 7.80 (s, 1H). MS (M+H): 322.5

Example 3

2-((trans)-2-(4-(benzyloxy)phenyl)cyclopropylamino)acetamide

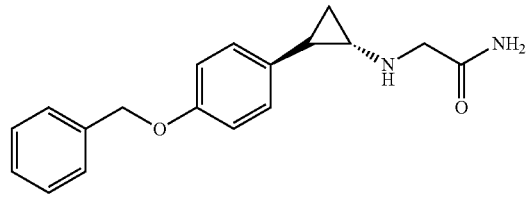

¹H-NMR (CDCl3) δ (ppm): 0.93 (m, 1H), 1.04 (m, 1H), 1.91 (m, 1H), 2.38 (m, 1H), 3.42 (s, 2H), 5.04 (s, 2H), 6.89 (d, 2H), 6.98 (d, 2H), 7.40 (m, 5H). MS (M+H): 297.2

Example 4

2-((trans)-2-(4-(4-fluorobenzyloxy)phenyl)cyclopropylamino)acetamide hydrochloride

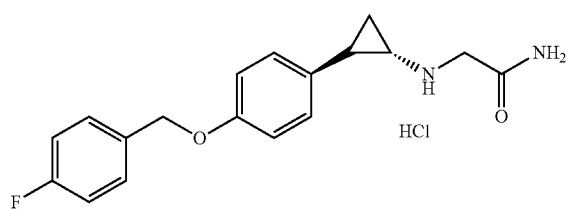

¹H-NMR (DMSO-d6) δ (ppm): 1.18 (q, 1H), 1.44 (quin, 1H), 2.84 (m, 1H), 3.80 (s, 2H), 5.04 (s, 2H), 6.91 (d, 2H), 7.09 (d, 2H), 7.22 (t, 2H), 7.47 (t, 2H), 7.60 (s, 1H), 7.89(s, 1H), 9.42 (br, 1H). MS (M+H): 315.3

Example 5

2-((trans)-2-(4-(3-fluorobenzyloxy)phenyl)cyclopropylamino)acetamide hydrochloride

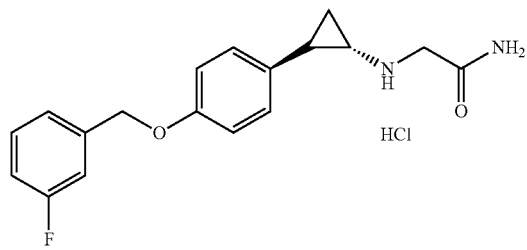

1HNMR (CD3OD) δ (ppm): 0.82 (m, 1H), 1.20 (m, 2H), 1.38 (m, 1H), 2.33 (m, 1H), 2.82 (m, 1H), 3.87 (s, 2H), 4.98 (s, 2H), 6.85 (d, 2H), 6.93 (m, 1H), 7.02 (d, 2H), 7.11 (t, 2H), 7.29 (q, 1H). MS (M+H): 315.3

Example 6

2-((trans)-2-(4-(3-chlorobenzyloxy)phenyl)cyclopropylamino)acetamide hydrochloride

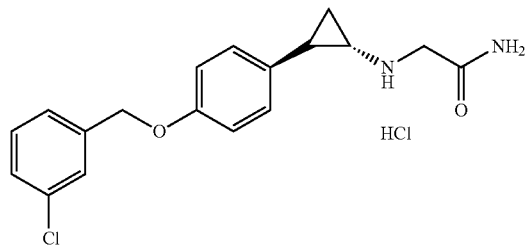

1H-NMR (DMSO-d6) δ (ppm): 1.18 (q, 1H), 1.44 (quin, 1H), 2.84 (m, 1H), 3.84 (s, 2H), 5.11(s, 2H), 6.96 (d, 2H), 7.13 (d, 2H), 7.40 (s, 3H), 7.49 (s, 1H), 7.60 (s, 1H), 7.78 (s, 1H), 9.40 (br, 1H). MS (M+H): 331.2

Example 7

2-((trans)-2-(4-(4-chlorobenzyloxy)phenyl)cyclopropylamino)acetamide hydrochloride

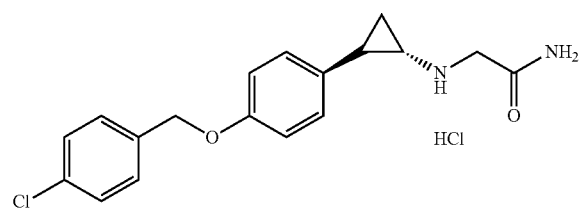

1H-NMR (DMSO-d6) δ (ppm): 1.18 (q, 1H), 1.44 (quin, 1H), 2.84 (m, 1H), 3.84 (s, 2H), 5.11(s, 2H), 6.96 (d, 2H), 7.13 (d, 2H), 7.40 (s, 4H), 7.60 (s, 1H), 7.78 (s, 1H), 9.49 (br, 1H). MS (M+H): 331.2

Example 8

2-((trans)-2-(4-(3-bromobenzyloxy)phenyl)cyclopropylamino)acetamide

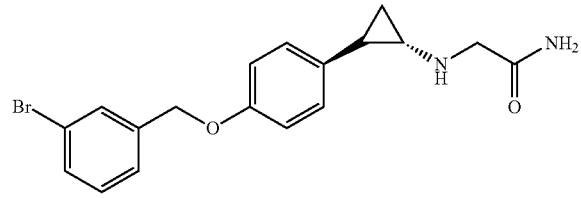

1H-NMR (CDCl3) δ (ppm): 0.96 (q, 1H), 1.04 (quin, 1H), 1.91 (m, 1H), 2.39 (m, 1H), 3.42 (s, 2H), 5.41 (s, 2H), 6.85 (d, 2H), 6.96 (d, 2H), 7.23 (d, 1H), 7.33 (d, 1H), 7.44 (d, 1H), 7.58 (s, 1H). MS (M+H): 375.0//377.0

Example 9

2((trans)-2-(4-(3,5-difluorobenzyloxy)phenyl)cyclopropylamino)acetamide

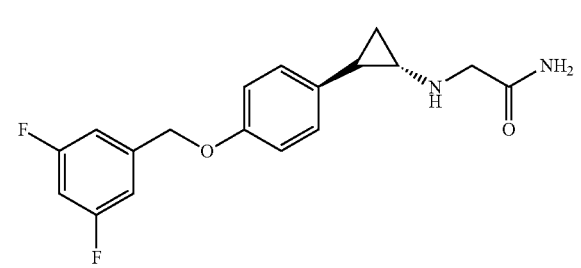

1H-NMR (CDCl3) δ (ppm): 0.95 (q, 1H), 1.04 (quin, 1H), 1.92 (m, 1H), 2.39 (m, 1H), 3.42 (s, 2H), 5.01 (s, 2H), 5.38 (br, 1H), 6.74 (t, 2H), 6.84 (d, 2H), 6.96 (t, 3H). MS (M+H): 333.1

Example 10

2-((trans)-2-(4-phenethoxyphenyl)cyclopropylamino)acetamide

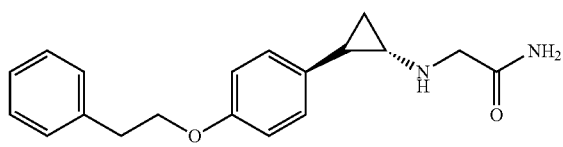

1H-NMR (CDCl3) δ (ppm): 0.94 (q, 1H), 1.03 (quin, 1H), 1.90 (m, 1H), 2.38 (m, 1H), 3.08 (t, 2H), 3.41 (s, 2H), 4.14 (t, 2H), 5.36 (br, 1H), 6.79 (d, 2H), 6.94 (d, 2H), 7.30 (m, 5H). MS (M+H): 311.1

Example 11

2-((trans)-2-(3'-(trifluoromethyl)biphenyl-4-yl)cyclopropylamino)acetamide

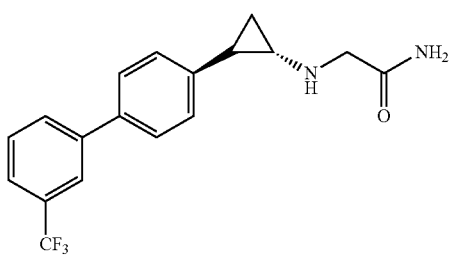

Step 1:
To a solution of tert-butyl(trans)-2-(4-bromophenyl)cyclopropylcarbamate (Intermediate C, 5 g) in diethyl ether (50 mL) HCl in diethyl ether (50 mL) was added at 0° C. and stirred at RT for 16 h. After completion, the solvent was evaporated and the residue was triturated with diethyl ether (2×10 mL) to give (trans)-2-(4-bromophenyl)cyclopropanamine hydrochloride (3 g, 76% yield) as a white solid.
$^1$H-NMR (400 MHz, CDCl$_3$) δ: 1.22 (m, 1H), 1.42 (m, 1H), 2.34 (m, 1H), 2.80 (m, 1H), 7.14 (d, 2H), 7.48 (d, 2H), 8.65-8.43 (brs, 3H).
Step 2:
To a suspension of K$_2$CO$_3$ (3.48 g, 25.4 mmol, 2.1 equiv) in dry DMF (30 mL) a solution of (trans)-2-(4-bromophenyl)cyclopropanamine hydrochloride (3 g, 12.09 mmol, 1 equiv) in dry DMF (6 mL) was added at 0° C. and stirred for 10 min, then 2-bromoacetamide (1.82 g, 13.3 mmol, 1.1 equiv) was added and stirred at RT for 2 h. After completion, the reaction mixture was poured into ice water (50 mL) and extracted with EtOAc (2×50 mL). The combined extracts were washed with water (2×50 mL), brine (50 mL), dried over anhydrous Na$_2$SO$_4$, filtered and evaporated. The crude residue was purified by column chromatography (SiO$_2$) using MeOH:CHCl$_3$ (3:97) to get 2-((trans)-2-(4-bromophenyl)cyclopropylamino)acetamide (1 g, 31% yield) as a white solid.
$^1$HNMR (400 MHz, CDCl$_3$) δ: 0.98 (m, 1H), 1.1 (m, 1H), 1.91 (m, 1H), 2.42 (m, 1H), 3.41 (s, 2H), 5.45 (m, 1H), 6.68 (m, 1H), 6.9 (d, 2H), 7.37 (d, 2H). Mass (M+H): 268.9.

Step 3:
A solution of 2-((trans)-2-(4-bromophenyl)cyclopropylamino)acetamide (100 mg, 0.37 mmol, 1 equiv), 3-trifluoromethyl benzene boronic acid (84 mg, 0.44 mmol 1.2 equiv), K$_2$CO$_3$ (152 mg, 1.11 mmol, 3 equiv) in CH$_3$CN+H$_2$O (4:1) (2 mL) was degassed for 30 min with Argon gas, then Pd(PPh$_3$)$_4$ (0.1 equiv) was added and the reaction mixture was heated at reflux temp. for 2 h. After completion, the reaction mixture was poured into ice water (10 mL), extracted with EtOAc (2×10 mL). The combined extracts were washed with water (10 mL), brine (10 mL), dried over anhydrous Na$_2$SO$_4$, filtered and evaporated. The crude residue was purified by prep HPLC to give 2-((trans)-2-(3'-(trifluoromethyl)biphenyl-4-yl)cyclopropylamino)acetamide (100 mg, 80% yield) as a white solid.
$^1$H-NMR (CDCl3) δ (ppm): 1.07 (q, 1H), 1.15 (quip, 1H), 2.01 (m, 1H), 2.51 (m, 1H), 3.45 (s, 2H), 5.50 (br, 1H), 6.74 (br, 1H), 7.12 (d, 2H), 7.48 (d, 2H), 7.56 (m, 2H), 7.73 (d, 1H), 7.79 (s, 1H). MS (M+H): 335.0.

The following examples have been synthesized using the procedure described for Example 11, employing the corresponding starting materials.

Example 12

2-(2-[1,1';4',1"]Terphenyl-4"-yl-cyclopropylamino)acetamide

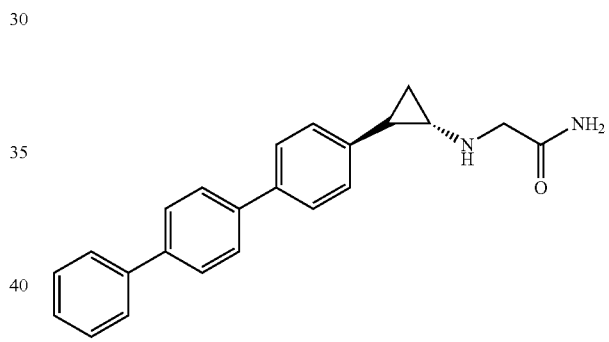

$^1$H-NMR (DMSO-d6) δ (ppm): 0.98 (q, 1H), 1.06 (quin, 1H), 1.90 (m, 1H), 2.35 (m, 1H), 2.85 (br, 1H), 3.15 (s, 2H), 7.03 (s, 1H), 7.14 (d, 2H), 7.28 (s, 1H), 7.38 (t, 1H), 7.48 (t, 2H), 7.58 (d, 2H), 7.70 (d, 2H), 7.73 (s, 4H). MS (M+H): 343.2

The following compounds can be synthesized following the methodology described in Scheme IV.

Example 13

(S)-2-((trans)-2-(4-(benzyloxy)phenyl)cyclopropylamino)propanamide

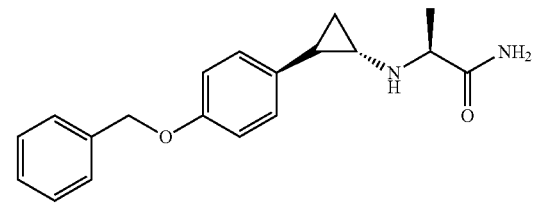

Example 14

(R)-2-((trans)-2-(4-(benzyloxy)phenyl)cyclopropylamino)propanamide

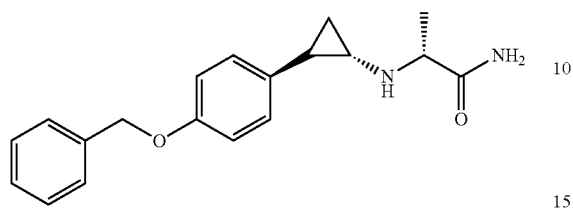

Example 15

(S)-2-((trans)-2-(4-(4-fluorobenzyloxy)phenyl)cyclopropylamino)propanamide

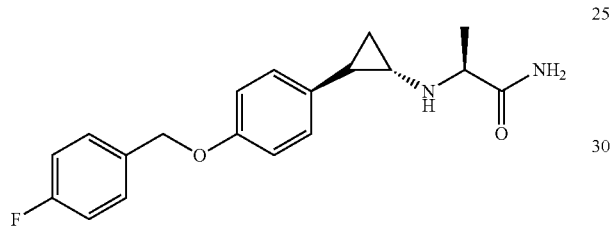

Example 16

(R)-2-((trans)-2-(4-(4-fluorobenzyloxy)phenyl)cyclopropylamino)propanamide

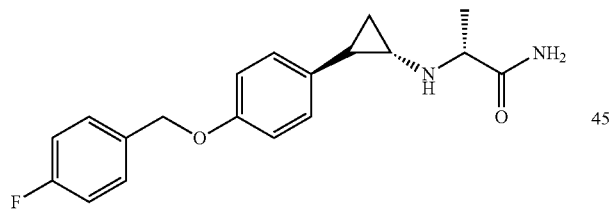

Example 17

(S)-2-((trans)-2-(4-(3-fluorobenzyloxy)phenyl)cyclopropylamino)propanamide

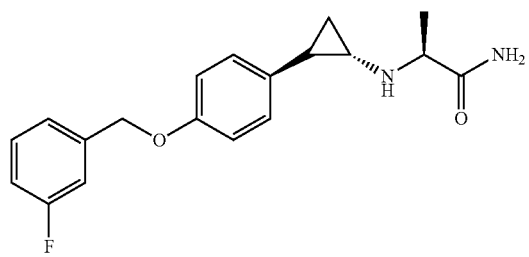

Example 18

(R)-2-((trans)-2-(4-(3-fluorobenzyloxy)phenyl)cyclopropylamino)propanamide

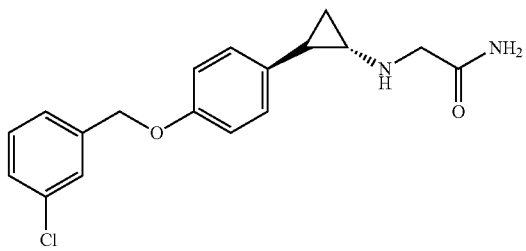

The following compounds can be synthesized following the methodology described in Scheme V.

Example 19

2-((trans)-2-(3'-chlorobiphenyl-4-yl)cyclopropylamino)acetamide

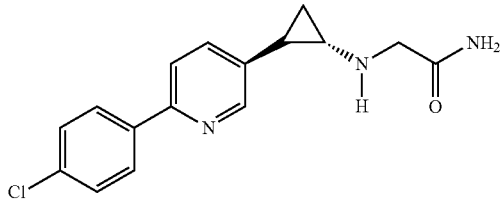

Example 20

2-((trans)-2-(6-(4-chlorophenyl)pyridin-3-yl)cyclopropylamino)acetamide

Example 21

5-((trans)-2-phenylcyclopropylamino)pentanamide hydrochloride

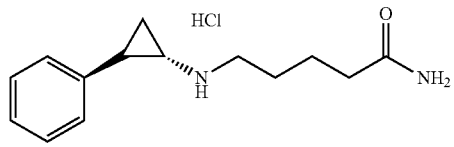

Example 22

4-((trans)-2-phenylcyclopropylamino)butanamide hydrochloride

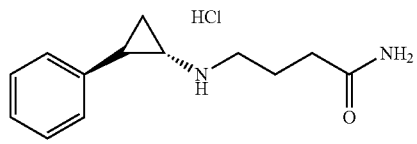

Example 23

3-((trans)-2-(4-(3-bromobenzyloxy)phenyl)cyclopropylamino)propanamide hydrochloride

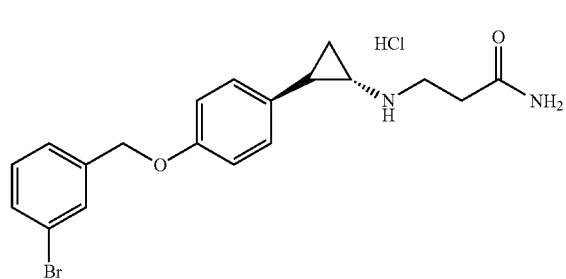

Example 24

5-((trans)-2-(4'-chlorobiphenyl-4-yl)cyclopropylamino)pentanamide hydrochloride

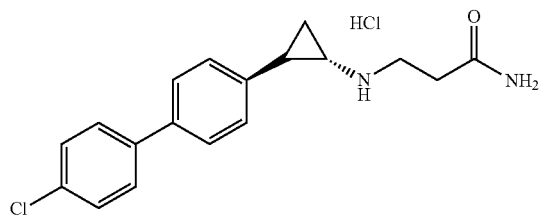

Example 25

5'-((trans)-2-(2-amino-2-oxoethylamino)cyclopropyl)-2'-(benzyloxy)biphenyl-3-carboxamide

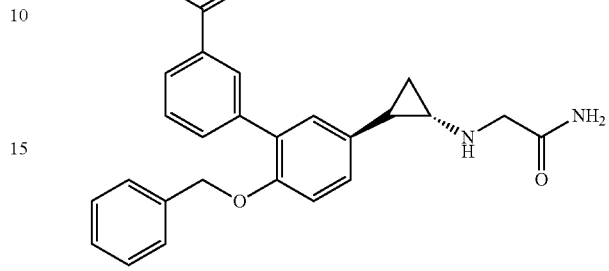

Other compounds similar to those of Examples 1-25, as illustrated below, that can be synthesized using the synthetic protocols or variations thereof as described herein using the appropriate reagents and starting materials, as readily recognized by the skilled artisan include, but are not limited to:

Example 26

3-((trans)-2-(4-(3-fluorobenzyloxy)phenyl)cyclopropylamino)-2,2-dimethylpropanamide

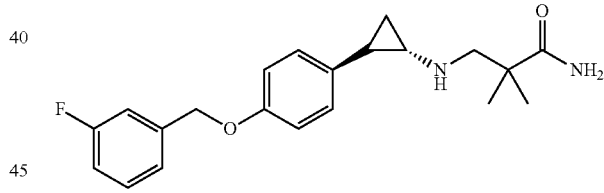

Example 27

4-((trans)-2-(4'-chlorobiphenyl-4-yl)cyclopropylamino)-2-methylbutanamide

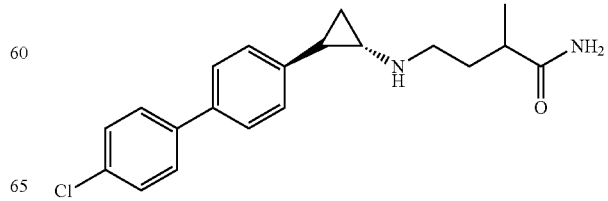

Example 28

5-((trans)-2-(4'-chlorobiphenyl-4-yl)cyclopropy-lamino)-2-methylpentanamide

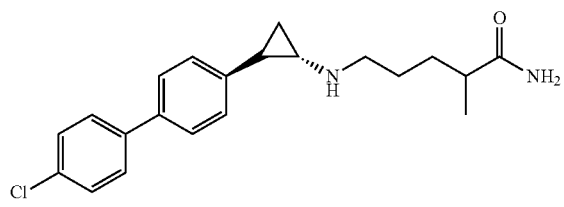

Example 29

3-((trans)-2-(4'-chlorobiphenyl-4-yl)cyclopropy-lamino)propanamide

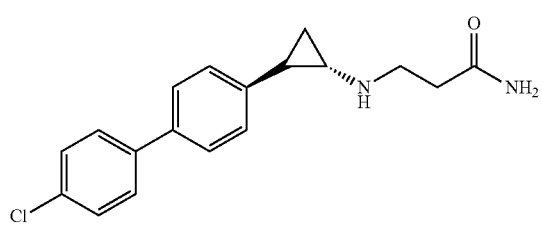

Example 30

4-((trans)-2-(4'-chlorobiphenyl-4-yl)cyclopropy-lamino)butanamide

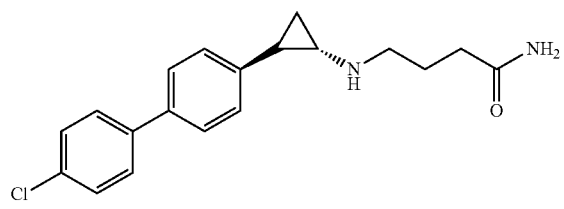

Example 31

4-((trans)-2-(4-(3-bromobenzyloxy)phenyl)cyclopro-pylamino)butanamide

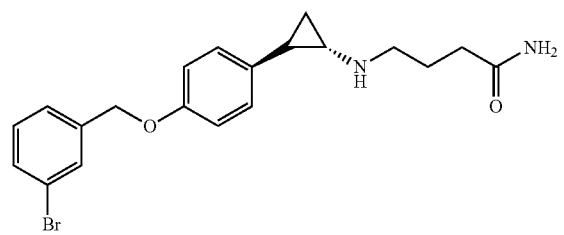

Example 32

5-((trans)-2-(4-(3-bromobenzyloxy)phenyl)cyclopro-pylamino)pentanamide

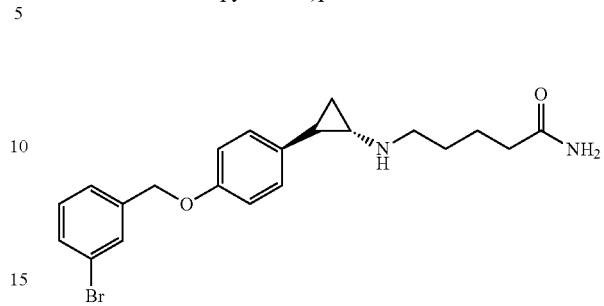

Example 33

5-((trans)-2-(6-(benzyloxy)biphenyl-3-yl)cyclopro-pylamino)pentanamide

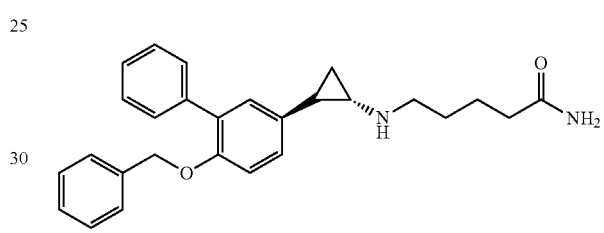

Example 34

4-((trans)-2-(6-(benzyloxy)biphenyl-3-yl)cyclopro-pylamino)butanamide

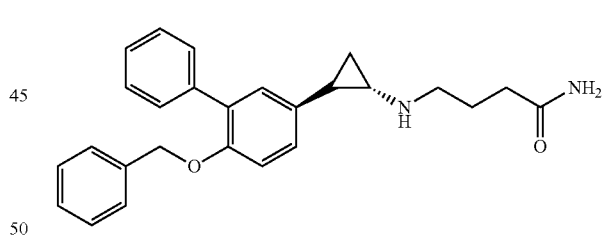

The compounds of the examples can also be synthesized or provided in a salt form. The skilled artisan is aware and capable of making salt forms and/or converting salt forms of the compounds of the invention including those of the Examples. In some cases the compounds of the invention, including those of the Examples can be more stable as salt forms as compared to free base.

Example 35

Biological Assays

The compounds of the invention can be tested for their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD1 was incubated on ice for 15 minutes, in the absence and/or in the presence of various concentrations of inhibitor (e.g., from 0 to 75 µM, depending on the inhibitor strength). Tranylcypromine (Biomol International) was used as a control for inhibition. Within the experiment, each concentration of inhibitor was tested in triplicate. After leaving the enzyme interacting with the inhibitor, 12.5 µM of di-methylated H3-K4 peptide was added to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 30 extra minutes at room temperature in the dark. A 1 µM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki ($IC_{50}$) of each inhibitor was estimated at half of the maximum activity.

The results presented in Table 1 below show the results of the LSD1 inhibition studies for a number of the Example compounds. Parnate (2-trans phenylcyclopropylamine) was found to have a Ki ($IC_{50}$) of from about 15 to 35 micromolar depending on the enzyme preparation. The studies show that the compounds of the invention have unexpectedly potent LSD1 inhibition.

Example 36

Biological Assays—Monoamine Oxidase Assays

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µL. The assay buffer was 100 mM HEPES, pH 7.5. Each experiment was performed in triplicate within the same experiment.

Briefly, a fixed amount of MAO (0.25 µg for MAO-A and 0.5 µg for MAO-B) was incubated on ice for 15 minutes in the reaction buffer, in the absence and/or in the presence of various concentrations of inhibitor (e.g., from 0 to 50 µM, depending on the inhibitor strength). Tranylcypromine (Biomol International) was used as a control for inhibition.

After leaving the enzyme(s) interacting with the inhibitor, 60 to 90 µM of kynuramine was added to each reaction for MAO-B and MAO-A assay respectively, and the reaction was left for 1 hour at 37° C. in the dark. The oxidative deamination of the substrate was stopped by adding 50 µL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki of each inhibitor was measure at Vmax/2.

TABLE 1

Summary of Data from MAO-A, MAO-B, and LSD1 Inhibition Studies

| Example Compound | MAO-A (Ki) | MAO-B (Ki) | LSD1 (Ki) |
|---|---|---|---|
| 1 | III | V | VI |
| 2 | IV | V | VI |
| 3 | III | V | V |
| 4 | II | V | V |
| 5 | III | V | VI |
| 6 | I | V | VI |
| 7 | II | V | V |
| 8 | III | V | VI |
| 9 | III | V | VI |
| 10 | III | V | VI |
| 11 | III | V | V |
| 12 | I | V | V |
| 19 | III | III | V, VI |
| 20 | IV | IV | VI |

The ranges for the Ki ($IC_{50}$) value reported in Table 1 are for MAO-A, MAO-B, and LSD1 are –I=much greater than 40 µM; II=greater than 40 µM; III=between 5 µM and 40 µM; IV between 0.5 µM and 5 µM; V between 0.1 µM and 0.5 µM; VI between 0.01 µM and 0.1 µM. The compounds of Examples were found to have Ki (IC50) values for MAO-A which are greater than the Ki values for LSD1 and MAO-B. The Ki values for MAO-A range from I-III, whereas the MAO-B Ki values are in the IV-V range and the LSD1 Ki values are in the V-VI range. Trans-2-phenylcyclopropylamine (tranylcypromine) was found to have a Ki for MAO-A of about 2 µM and a Ki of about 0.6 µM for MAO-B and from about 15-35 µM for LSD1 in these assays described herein.

The invention therefore provides inhibitors selective for LSD1 and MAO-B as compared to MAO-A. Preferably, LSD1/MAO-B selective inhibitors have Ki values for LSD1 which are at least 2-fold lower than the Ki value for MAO-A. Example of LSD1/MAO-B selective inhibitor are shown in Table 1 which shows Ki values for LSD1 and MAO-B which are about 5 to 10-fold lower than their Ki values for MAO-A.

It is contemplated that some compounds of the invention may be selective LSD1 inhibitors in that they are better inhibitors of LSD1 than both MAO-A and MAO-B. Preferably LSD1 selective inhibitors have Ki values for LSD1 which are at least 2-fold lower than the Ki value for MAO-A and MAO-B. Even more preferably LSD1 selective inhibitors have Ki values for LSD1 which are at least 5-fold lower than the Ki value for MAO-A and MAO-B.

Without being bound by theory, it is the inventor's belief that compounds of the invention that have substitutions in the linker (L) alpha to the —C(=O)NH$_2$ group have improved stability in vivo. Thus, compounds of the invention of Formula (A')$_X$-(A)-(B)—(Z)—(CH$_2$)$_m$CR$_1$R$_2$—C(=O)NH$_2$ wherein R$_1$, R$_2$ or both are C$_1$-C$_6$ alkyl groups are expected to have better in vivo stability and cleared less rapidly.

Thus, the compounds of the invention inhibit two biologically relevant targets, LSD1 and MAO-B. MAO-B inhbitors are clinically used for depression and Parkinson's disease. MAO-B inhibitors have been shown to possess neuroprotective properties. In addition, LSD1 has been shown to be part of a protein complex (REST/CoREST) involved in regulating gene expression in cancer and neurodegeneration. Without being bound by theory, it is the inventor's belief that inhibition of both targets LSD1 and MAO-B will be beneficial for neurodegeneration.

LSD1 is known to regulate global levels of H3K4me2, H3K4me1, and Histone H3K9me2 (Histone-3 Lysine 4 dimethyl, histone-3 lysine 4 monomethyl, and histone-3 lysine 9 dimethyl). Inhibitors of LSD1 have been shown in the literature to increases global levels of H3K4me2 and H3K4me1. Studies in lung cancer, prostate, and kidney cancers have shown that lower global levels of H3K4me2 and/or H3K9me2 are signifigantly associated with poorer prognosis (e.g., survival). See e.g., Seligson et al. (2009) Am. J. Path. 174:1619-28. Seligson et al. (2005) Nature 435:1262-1266. Elsheikh et al. Canc. Res. (2009) 69:3802-3809 showed that low levels of H3K4me2 is associated with poor prognosis in Breast cancer. Barlesi et al. ((2007) J Clin Oncol; 25:4358-4364 showed that in NSCLC, nonadenocarcinoma patienst with high levels of H3K4me2 had a median survival of 147 months wheras adenocarcinoma patients with low H3K9acetylation levels had a median survival of 10 months. Thus, LSD1 and histone lysine methylation levels have been shown to be involved in a number of different cancers.

Previous studies reported in the literature indicated that substitutions on the amine group of phenylcyclopropylamines reduced the ability of the compound to inhibit monoamine oxidases, which have significant structural homology to LSD1. For example, Zirkle et al. ((1962) *J. Med. Chem.* 1265-1284) found that a methyl substituent on the amine group decreased activity slightly whereas substitution with larger alkyl groups and groups bearing ring ring system like aralkyls reduced MAO activity substantially. Furthermore, as a general trend, substitutions on the phenyl ring of phenylcyclopropylamine were shown to be less active compounds. McCafferty et al. found that replacement of the phenyl group of phenylcyclopropylamine with a larger group like napthyl reduced inhibitory activity. The inventors of the instant invention have unexpectedly found that ring bearing substitutions on the phenyl group of the phenylcyclopropyl amine core of Formula (I) produce potent LSD1/MAO-B inhibitors. Furthermore, the inventors found that the acetamide (—CH$_2$(C=O)NH$_2$) moiety gives compounds that inhibit both LSD1 and MAO-B potently. The results of the instant invention show that further modifications to the phenylpropylamine core as described herein can result in potent LSD1/MAO-B inhibitors. The Examples show compounds which selectively inhibit LSD1 and MAO-B compared to MAO-A. It is contemplated that some compounds of the invention inhibit LSD1 selectively e.g., inhibit LSD1 to a greater extent than MAO-A and MAO-B. Thus, the inventors have discovered unexpectedly a new class of aryl- and heteroarylcyclopropylamine (e.g., phenylcyclopropylamine) containing amine oxidase inhibitors with activity against biologically relevant targets in CNS conditions (neurodegeneration), depression, and cancer.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:

1. A compound of Formula (I)

$$(A')_X\text{-(A)-(B)}\text{—(Z)-(L)-C(=O)NH}_2 \quad (I)$$

or a pharmaceutically acceptable salt or solvate thereof, wherein:
  (A) is heteroaryi or aryl;
  each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2 or 3 substituents independently chosen from halo, haloalkyl, aryl, arylalkoxy, alkyl, alkoxy, cyano, sulfonyl, sulfinyl, and carboxamide;
  X is 0, 1, 2, or 3;
  (B) is a cyclopropyl ring, wherein (A) and (Z) are covalently bonded to different carbon atoms of (B);
  (Z) is —NH—; and
  (L) is —(CH$_2$)$_m$CR$_1$R$_2$—, wherein m is 0, 1, 2, 3, 4, 5, or 6, and wherein R$_1$ and R$_2$ are each independently hydrogen or C$_1$-C$_6$ alkyl;
    provided that, if (L) is —CH$_2$— or —CH(CH$_3$)—, then X is not 0.

2. The compound of claim 1 or a pharmaceutically acceptable salt or solvate thereof, wherein (A) is aryl.

3. The compound of claim 1 or a pharmaceutically acceptable salt or solvate thereof, wherein (A) is phenyl.

4. The compound of claim 1 or a pharmaceutically acceptable salt or solvate thereof, wherein (A) is heteroaryl.

5. The compound of claim 1 or a pharmaceutically acceptable salt or solvate thereof, wherein (A) is chosen from pyridyl, pyrimidinyl, and thiophenyl.

6. The compound of claim 1 or a pharmaceutically acceptable salt or solvate thereof, wherein (A) is pyridyl.

7. The compound of claim 1 or a pharmaceutically acceptable salt or solvate thereof, wherein X is 1 or 2.

8. The compound of claim 1 or a pharmaceutically acceptable salt or solvate thereof, wherein X is 1 and (A') is independently chosen from aryl, arylalkoxy, arylalkyl, and aryloxy, wherein said aryl, arylalkoxy, arylalkyl, or aryloxy has 0 or 1 substituent chosen from halo, haloalkyl, and cyano.

9. The compound of claim 1 or a pharmaceutically acceptable salt or solvate thereof, wherein X is 1 and (A') is independently chosen from phenyl, benzyl, and benzyloxy, wherein said phenyl, benzyl, or benzyloxy has 0 or 1 substituent chosen from halo, haloalkyl, and cyano.

10. The compound of claim 1 or a pharmaceutically acceptable salt or solvate thereof, wherein (L) is —CR$_1$R$_2$—, wherein R$_1$ and R$_2$ are each independently hydrogen or C$_1$-C$_6$ alkyl.

11. The compound of claim 1 or a pharmaceutically acceptable salt or solvate thereof, wherein $R_1$ and $R_2$ are each $C_1$-$C_6$ alkyl.

12. The compound of claim 1 or a pharmaceutically acceptable salt or solvate thereof, wherein $R_1$ and $R_2$ are each methyl.

13. The compound of claim 1 or a pharmaceutically acceptable salt or solvate thereof, wherein $R_1$ is methyl and $R_2$ is hydrogen.

14. The compound of claim 1 or a pharmaceutically acceptable salt or solvate thereof, wherein (L) is —$(CH_2)_2C(C_1$-$C_3$alkyl)($C_1$-$C_3$ alkyl)—, —$(CH_2)_3C(C_1$-$C_3$alkyl)($C_1$-$C_3$alkyl)—, —$(CH_2)_3CH(CH_2CH_3)$—, —$(CH_2)_3CH(CH_3)$—, —$(CH_2)_2CH(CH_3)$—, or —$(CH_2)_2CH(CH_2CH_3)$—.

15. The compound of claim 1 or a pharmaceutically acceptable salt or solvate thereof, wherein (A) and (Z) are in the trans orientation with respect to the cyclopropyl ring (B).

16. The compound of claim 1 or a pharmaceutically acceptable salt or solvate thereof, wherein: X is 1; (A) is phenyl; and (A') is covalently bonded to (A) in the para position in respect of the cyclopropyl ring (B).

17. The compound of claim 1, wherein said compound is a compound of Formula (II)

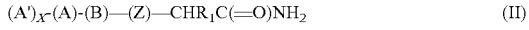

(A')$_X$-(A)-(B)—(Z)—CHR$_1$C(=O)NH$_2$    (II)

or a pharmaceutically acceptable salt or solvate thereof, wherein:

(A) is heteroaryl or aryl;
each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, or 2 substituents independently chosen from halo, haloalkyl, aryl, arylalkoxy, alkyl, alkoxy, cyano, sulfonyl, and sulfinyl;
X is 0, 1, 2, or 3;
(B) is a cyclopropyl ring, wherein (A) and (Z) are covalently bonded to different carbon atoms of (B);
(Z) is —NH—; and
$R_1$ is hydrogen or $C_1$-$C_6$ alkyl;
provided that, if $R_1$ is hydrogen or methyl, then X is not 0.

18. The compound of claim 17 or a pharmaceutically acceptable salt or solvate thereof, wherein (A) is aryl.

19. The compound of claim 17 or a pharmaceutically acceptable salt or solvate thereof, wherein (A) is phenyl.

20. The compound of claim 17 or a pharmaceutically acceptable salt or solvate thereof, wherein X is 1 or 2.

21. The compound of claim 17 or a pharmaceutically acceptable salt or solvate thereof, wherein X is 1 and (A') is chosen from aryl, arylalkoxy, arylalkyl, and aryloxy, wherein said aryl, arylalkoxy, arylalkyl, or aryloxy has 0 or 1 substituent chosen from halo, haloalkyl, and cyano.

22. The compound of claim 17 or a pharmaceutically acceptable salt or solvate thereof, wherein X is 1 and (A') is chosen from phenyl, benzyl, and benzyloxy, wherein said phenyl, benzyl, or benzyloxy has 0 or 1 substituent chosen from halo, haloalkyl, and cyano.

23. The compound of claim 17 or a pharmaceutically acceptable salt or solvate thereof, wherein $R_1$ is $C_1$-$C_6$ alkyl.

24. The compound of claim 23 or a pharmaceutically acceptable salt or solvate thereof, wherein $R_1$ is methyl.

25. The compound of claim 17 or a pharmaceutically acceptable salt or solvate thereof, wherein $R_1$ is hydrogen.

26. The compound of claim 17 or pharmaceutically acceptable salt or solvate thereof, wherein (A) is heteroaryl.

27. The compound of claim 26 or a pharmaceutically acceptable salt or solvate thereof, wherein (A) is a heteroaryl chosen from pyridyl, pyrimidinyl, and thiophenyl.

28. The compound of claim 27 or a pharmaceutically acceptable salt or solvate thereof, wherein (A) is pyridyl.

29. The compound of claim 17 or a pharmaceutically acceptable salt or solvate thereof, wherein (A) and (Z) are in the trans orientation with respect to the cyclopropyl ring (B).

30. The compound of claim 17 or a pharmaceutically acceptable salt or solvate thereof, wherein: X is 1; (A) is phenyl; and (A') is covalently bonded to (A) in the para position in respect of the cyclopropyl ring (B).

31. The compound of claim 17 or a pharmaceutically acceptable salt or solvate thereof, wherein:
(A) is phenyl;
each (A'), if present, is independently chosen from aryl, arylalkoxy, arylalkyl, heterocyclyl, and aryloxy, wherein each (A') is substituted with 0, 1, or 2 substituents independently chosen from halo, haloalkyl, alkyl, alkoxy, cyano, sulfonyl, and sulfinyl; and
$R_1$ is hydrogen.

32. The compound of claim 1, wherein said compound is chosen from
2-((trans)-2-(4-(4-cyanobenzyloxy)phenyl)cyclopropylamino)acetamide,
2-((trans)-2-(4-(3-cyanobenzyloxy)phenyl)cyclopropylamino)acetamide,
2-((trans)-2-(4-(benzyloxy)phenyl)cyclopropylamino)acetamide,
2-((trans)-2-(4-(4(benzyloxy)phenyl)cyclopropylamino)acetamide,
2-((trans)-2-(4-(3-fluorobenzyloxy)phenyl)cyclopropylamino)acetamide,
2-((trans)-2-(4-(3-chlorobenzyloxy)phenyl)cyclopropylamino)acetamide,
2-((trans)-2-(4-(4-chlorobenzyloxy)phenyl)cyclopropylamino)acetamide,
2-((trans)-2-(4-(3-brornobenzyloxy)phenyl)cyclopropylamino)acetamide,
2-((trans)-2-(4-(3,5-difluorobenzyloxy)phenyl)cyclopropylamino)acetamide,
2-((trans)-2-(4-phenethoxyphenyl)cyclopropylarnino)acetamide,
2-((trans)-2-(3'-(trifluoromethyl)biphenyl-4-yl)cyclopropylamino)acetamide,
2-((trans)-2-(3'-chlorobiphenyl-4-yl)cyclopropylamino)acetamide,
2-((trans)-2-(6-(4-chlorophenyl)pyridin-3-yl)cyclopropylamino)acetamide,
(R)-2-((trans)-2-(4-(3-fluorobenzyloxy)phenyl)cyclopropylamino)propanamide,
(S)-2-((trans)-2-(4-(4-fluorobenzyloxy)phenAcyclopropylamino)propanamide,
(R)-2-((trans)-2-(4-(4-fluorobenzyloxy)phenyi)cyclopropylamino)propanamide,
(S)-2-((trans)-2-(4-(4-fluorobenzyloxy)phenyl)cyclopropylamino)propanamide,
(R)-2-((trans)-2-(4-(benzyloxy)phenyl)cyclopropylamino)propanamide,
(S)-2-((trans)-2-(4-(benzyloxy)phenyl)cyclopropylamino)propanamide,
2-(2-[1,1';4', 1"]Terphenyl-4"-yl-cyclopropylamino)acetamide,
5'-((trans)-2-(2-amino-2-oxoethylamino)cyclopropyl)-2'-(benzyloxy)biphenyl-3-carboxamide,
5-((trans)-2-(4'-chlorobiphenyl-4-yl)cyclopropylamino)pentanamide, 3-((trans)-2-(4-(3-bromobenzyloxy)phenyl)cyclopropylamino)propanamide,
4-((trans)-2-phenylcyclopropylamino)butanamide,
5-((trans)-2-phenylcyclopropylamino)pentanamide,
5-((trans)-2-(4'-chlorobiphenyl-4-yl)cyclopropylamino)-2-methylpentanamide,
4((trans)-2-(4'-chlorobiphenyl-4-yl)cyclopropylamino)-2-methylbutanamide,
3-((trans)-2-(4-(3-fluorobenzyloxy)phenyl)cyclopropylamino)-2,2-dimethylpropanamide,
3-((trans)-2-(4'-chlorobiphenyl-4-yl)cyclopropylamino)propanamide,
4-((trans)-2-(4'-chlorobiphenyl-4-yl)cyclopropylamino)butanamide,
4-((trans)-2-(4-(3-bromobenzyloxy)phenyl)cyclopropylamino)butanamide,
5-((trans)-2-(4-(3-bromobenzyloxy)phenyl)cyclopropylamino)pentanamide,
5-((trans)-2-(6-(benzyloxy)biphenyl-3-yl)cyclopropylamino)pentanamide, and
4-((trans)-2-(6-(benzyloxy)biphenyl-3-yl)cyclopropylamino)butanamide,
or a pharmaceutically acceptable salt or solvate thereof.

33. A pharmaceutical composition comprising the compound of claim 1 or a pharmaceutically acceptable salt or solvate thereof, and a pharmaceutically acceptable carrier.

* * * * *